(12) United States Patent
Lam et al.

(10) Patent No.: US 10,494,401 B2
(45) Date of Patent: *Dec. 3, 2019

(54) LLP2A-BISPHOSPHONATE CONJUGATES FOR OSTEOPOROSIS TREATMENT

(71) Applicant: The Regents of the University of California, Oakland, CA (US)

(72) Inventors: Kit S. Lam, Davis, CA (US); Ruiwu Liu, Sacramento, CA (US); Wei Yao, El Dorado Hills, CA (US); Nancy Lane, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,380

(22) Filed: Dec. 21, 2016

(65) Prior Publication Data

US 2017/0174722 A1    Jun. 22, 2017

Related U.S. Application Data

(63) Continuation of application No. 14/806,398, filed on Jul. 22, 2015, now Pat. No. 9,561,256, which is a continuation of application No. 13/820,362, filed as application No. PCT/US2012/021909 on Jan. 19, 2012, now Pat. No. 9,119,884, which is a continuation-in-part of application No. PCT/US2011/050381, filed on Sep. 2, 2011.

(60) Provisional application No. 61/379,643, filed on Sep. 2, 2010.

(51) Int. Cl.

| | | |
|---|---|---|
| *A61K 38/00* | (2006.01) |
| *A61P 19/08* | (2006.01) |
| *A61P 19/02* | (2006.01) |
| *A61P 19/10* | (2006.01) |
| *A61K 38/10* | (2006.01) |
| *A61K 38/16* | (2006.01) |
| *A61K 38/08* | (2019.01) |
| *A61K 38/06* | (2006.01) |
| *A61K 38/07* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 5/097* | (2006.01) |
| *A61K 31/663* | (2006.01) |
| *C07K 7/06* | (2006.01) |
| *A61K 31/66* | (2006.01) |
| *C07F 9/02* | (2006.01) |
| *A61K 31/00* | (2006.01) |
| *A61K 31/661* | (2006.01) |
| *C07K 5/09* | (2006.01) |
| *C07K 5/103* | (2006.01) |
| *C07K 5/107* | (2006.01) |
| *C07K 5/11* | (2006.01) |
| *A61K 35/28* | (2015.01) |
| *A61K 47/54* | (2017.01) |
| *A61K 47/64* | (2017.01) |

(52) U.S. Cl.
CPC ............ *C07K 5/0821* (2013.01); *A61K 31/00* (2013.01); *A61K 31/66* (2013.01); *A61K 31/661* (2013.01); *A61K 31/663* (2013.01); *A61K 35/28* (2013.01); *A61K 38/06* (2013.01); *A61K 38/08* (2013.01); *A61K 38/10* (2013.01); *A61K 47/548* (2017.08); *A61K 47/64* (2017.08); *C07F 9/02* (2013.01); *C07K 5/0817* (2013.01); *C07K 5/101* (2013.01); *C07K 5/1016* (2013.01); *C07K 5/1019* (2013.01); *C07K 7/06* (2013.01); *A61K 38/00* (2013.01)

(58) Field of Classification Search
None
See application file for complete search history.

(56) References Cited

U.S. PATENT DOCUMENTS

| | | |
|---|---|---|
| 6,008,207 A | 12/1999 | Brenner et al. |
| 6,248,713 B1 | 6/2001 | Lin et al. |
| 7,576,175 B2 | 8/2009 | Lam et al. |
| 9,119,884 B2 | 9/2015 | Lam et al. |

(Continued)

FOREIGN PATENT DOCUMENTS

| | | |
|---|---|---|
| WO | 97/03094 A1 | 1/1997 |
| WO | 98/42656 A1 | 10/1998 |

(Continued)

OTHER PUBLICATIONS

Morrison, M.S., "Physical Therapist's Guide to Osteopenia (Low Bone Mass)", available online at https://www.moveforwardpt.com/SymptomsConditionsDetail.aspx?cid=3077efa9-4453-498d-91fa-5f9f350663ac, 7 pages (accessed on Jul. 5, 2019) (Year: 2019).*

(Continued)

*Primary Examiner* — James H Alstrum-Acevedo
*Assistant Examiner* — Thea D' Ambrosio
(74) *Attorney, Agent, or Firm* — Kilpatrick Townsend & Stockton LLP

(57) ABSTRACT

The present invention provides compounds and pharmaceutical compositions of a peptidomimetic ligand, e.g. LLP2A, conjugated with a bisphosphonate drug, e.g. Alendronate. The compounds and pharmaceutical compositions of the present invention are useful in the treatment of osteoporosis and for the promotion of bone growth due to their specificity for the $\alpha_4\beta_1$ integrin on mesenchymal stem cells and for the surface of bone.

19 Claims, 25 Drawing Sheets

Specification includes a Sequence Listing.

(56) References Cited

U.S. PATENT DOCUMENTS

| | | |
|---|---|---|
| 9,561,256 B2 | 2/2017 | Lam et al. |
| 2002/0128301 A1 | 9/2002 | Zhou et al. |
| 2005/0256040 A1 | 11/2005 | Bredesen et al. |
| 2006/0019900 A1 | 1/2006 | Lam et al. |
| 2006/0165799 A1 | 7/2006 | Kim et al. |
| 2010/0021379 A1 | 1/2010 | Lam et al. |
| 2010/0047258 A1 | 2/2010 | Wang et al. |
| 2016/0243250 A1* | 8/2016 | Lane ............... A61K 31/663 |

FOREIGN PATENT DOCUMENTS

| | | |
|---|---|---|
| WO | 01/44258 A1 | 6/2001 |
| WO | 01/58871 A1 | 8/2001 |
| WO | 08/031016 A2 | 3/2008 |

OTHER PUBLICATIONS

Aina et al., "Therapeutic Cancer Targeting Peptides. Biopolymers," Peptide Science, 66:184-199, (2002).
Barnes et al., "Recent developments in the encoding and deconvolution of combinatorial libraries," Curr. Opin. Chem. Biol. 4:346-350 (2000).
Chait et al., "Protein ladder sequencing," Science 262:89-92 (1993).
Carpenter et al., J. Comb. Chem., 2006, 8, 907-914.
Chen et al., Biochemistry, 1998, 37:8743-8753.
Chen et al., "One bead-one compound combinatorial peptide library: different types of screening," Methods Enzymol. 267:211-219 (1996).
Coiffier et al., "Rituximab (Anti-CD20 Monoclonal Antibody) for the Treatment of Patients With Relapsing or Refractory Aggressive Lymphoma: A Multicenter Phase II Study," Blood, 92(6):1927-1932 (1998).
Czarnik, "Encoding methods for combinatorial chemistry," Curr Opin. Chem. Biol. 1: 60-66 (1997).
Damiano et al., "Integrin-mediated drug resistance in multiple myeloma," Leuk. Lymphoma. 38: 71-81 (2000).
Diels et al., "Reduction in New Metastases in Breast Cancer with Adjuvant Clondronate Treatment," New Engl. J. Med. 339:357-363 (1998).
De La Fuente et al., "Fibronectin interaction with 4β1 integrin prevents apoptosis in B cell chronic lymphocytic leukemia: correlation with Bcl-2 and Bax," Leukemia 13:266-274 (1999).
Denardo et al., "111-In-LLP2A-DOTA Polyethlene Glycol-Targeting alpha4betal Integrin: Comparative Pharmacokinetics for Imaging and Therapy of Lymphoid Malignancies," J. Nucl. Med., 2009, vol. 50, pp. 625-634.
Foon et al., "Are Solid Tumor Anti-Idiotype Vaccines Ready for Prime Time?" Clin. Cancer Res. 7:1112-1115 (2001).
Green, "Antitumore Effects of Bisphosphonates," Cancer (Suppl. 3) 97:840-847 (2003).
Hemler, "VLA proteins in the integrin family: structures, functions, and their role on leukocytes," Ann. Rev. Immunol., 8:365 (1990).
Holzmann et al., "4 integrins and tumor metastasis," Curr. Top. Microbiol. Immunol., 231:125-141 (1998).
Hood et al., "Role of integrins in. cell invasion and migration," Nat. Rev. Cancer, 2:91-100 (2002).
Hynes, "Integrins: bidirectional, allosteric signaling machines," Cell, 110:673-687 (2002).
Hynes, "Integrins: versatility, modulation and signaling in cell adhesion," Cell, 69:11-25 (1992).
Jin et al., "Integrins: roles in cancer development and as treatment targets," Brit. J. Cancer, 90:561-565 (2004).
Kenyon et al., An alpha4betal integrin antagonist decreases airway inflammation in ovalbumin-exposed mice, Eur J. European Journal of Pharmacology, Jan. 2009, vol. 603(1-3), pp. 138-46.
Klominek et al., "Differential motile response of human malignant mesothelioma cells to fibronectin, laminin and collagen type IV: The role of 1 integrins," Int. J. Cancer, 72:1034-1044 (1997).
Kumar et al., "Bone homing of mesenchymal stem cells by ectoic α4 integrin expression," The FASEB Journal, 2007, vol. 21, pp. 3917-3927.
Kwekkeboom et al., "Peptide Receptor Imaging and Therapy," J. Nucl. Med. 41:1704-1713 (2000).
Lam et al., "The "One-Bead-One-Compound" Combinatorial Library Method," Chem. Rev. 97(2):411-448 (1997).
Lam et al., "A new type of synthetic peptide library for identifying ligand-binding activity," Nature, 354:82-84 (1991).
Lin et al., J. Med. Chem., 1999, 42:920-934.
Lin et al., "Very late antigen 4 (VLA4) antagonists as anti-inflammatory agents ," Curr Opin. Chem. Biol. 2(4):453-457 (1998).
Liu et al., "A novel peptide-based encoding system for 'one-bead one-compound' and small molecule combinatorial libraries," J. Am. Chem. Soc. ,124:7678-7680 (2002).
Lowman et al., "Baceriophage display and discovery of peptide leads for drug development," Annu. Rev. Biophys. Biomol. Struct., 26:401-424 (1997).
Marco et al., "Alpha 4 integrin increases anoikis of human osteosarcoma cells," J. Cell. Biochem. 88, 1038-1047 (2003).
Okarvi, "Peptide-based radiopharmaceuticals: Future tools for diagnostic imaging of cancers and other diseases," Med. Res. Rev. 24(3):357-359 (2004).
Park et al., Letters Pept. Sci., 8:171-178, 2002.
Pasqualini et al., "Organ targeting in vivo using phage display peptide libraries," Nature 380:364-366 (1996).
Peng, Li et al., "Combinatorial chemistry indentifies high-affinity peptidomimetics against α4β1 integrin for in vivo tumor imaging," Nature Chemical Biology, Jul. 2006, vol. 2, No. 7, pp. 381-389.
Peng et al., In vivo optical imaging of human lymphoma xenograft using a library-derived peptidomimetic against alpha4betical integrin, Moleuclar Cancer Therapeutics, Feb. 2008, vol. 7(2), pp. 432-7.
Shimaoka et al., "Conformational Regulation Of Integrin Structure And Function," Annu. Rev. Biophys. Biomol. Struct. 31:485-516 (2002).
Song et al., "A novel and rapid encoding method based on mass spectrometry for "one-bead-one-compound" small molecule combinatorial libraries," J. Am. Chem. Soc. 125(20):6180-6188 (2003).
Till et al., "The chemokine receptor CCR7 and 4 integrin are important for migration of chronic lymphocytic leukemia cells into lymph nodes," Blood 99(8):2977 (2002).
Vincent et al., "Integrin function in chronic lymphocytic leukemia," Blood 87(11):4780-4788(1996).
Wang et al., "Encoding method for OBOC small molecule libraries using a biphasic approach for ladder-synthesis of coding tags," J. Am. Chem. Soc. 126:5740-5749 (2004).
Youngquist et al., "Generation and screening of combinatorial peptide libraries designed for rapid sequencing by mass-spectrometry," J. Am. Chem. Soc. 117, 3900-3906 (1995).
Yusuf-Makagiansar et al., "Inhibition of LFA-1/ICAM-1 and VLA-4/VCAM-1 as a therapeutic approach to inflammation and autoimmune diseases," Med. Res. Reviews, 22:146-167 (2002).
International Search Report, dated Oct. 24, 2012, PCT application No. PCT/US2012/021909, 9 pages.
Extended European Search Report, dated Feb. 25, 2015, EP Application No. 12826522.0-1451, 4 pages.

* cited by examiner

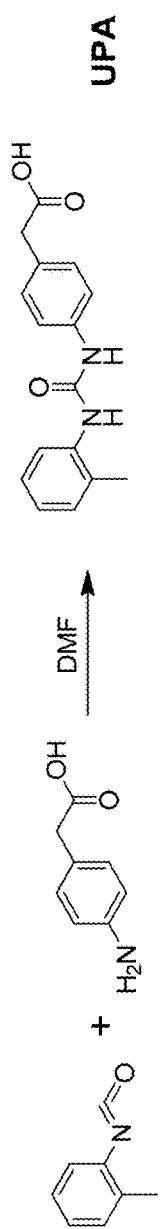
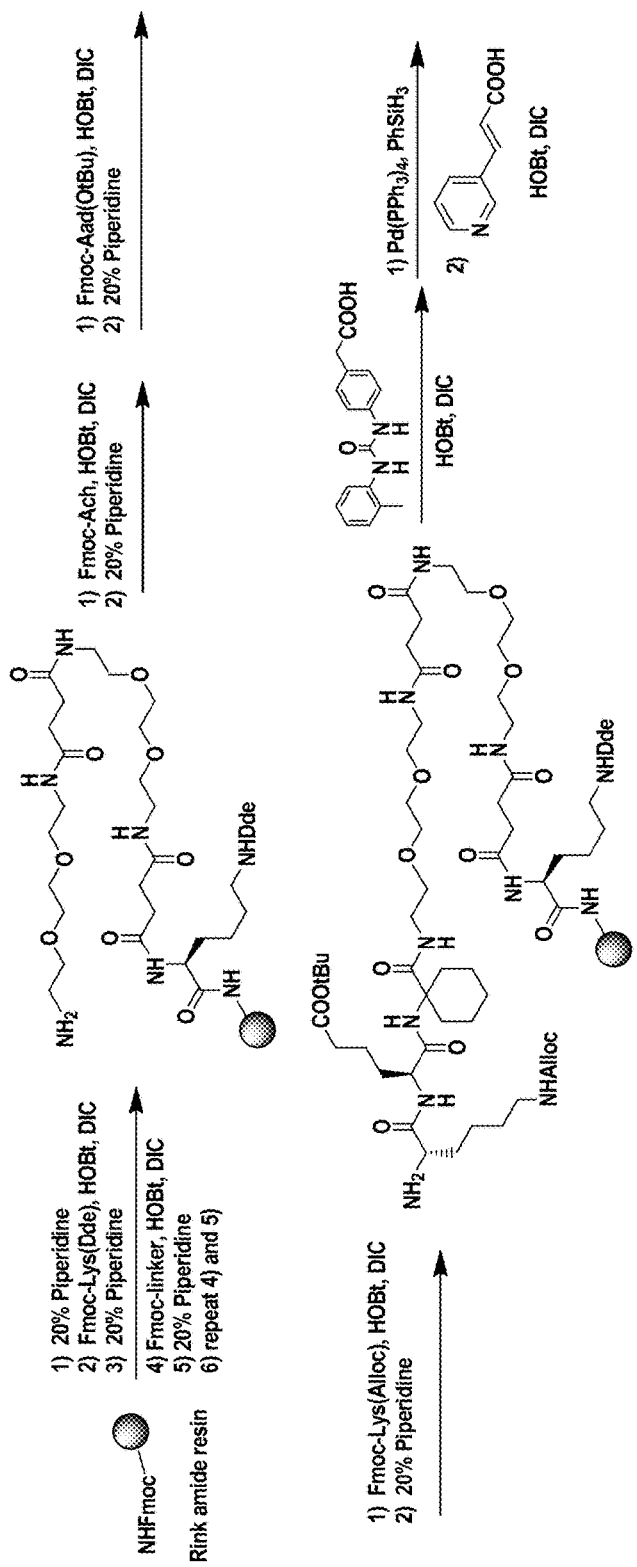
FIG. 10A
FIG. 10B

LLP2A-BISPHOSPHONATE CONJUGATES FOR OSTEOPOROSIS TREATMENT

CROSS-REFERENCES TO RELATED APPLICATIONS

This application is a continuation of U.S. patent application Ser. No. 14/806,398, filed Jul. 22, 2015, which is a continuation of U.S. patent application Ser. No. 13/820,362, filed Oct. 28, 2013, issued as U.S. Pat. No. 9,119,884, which is a National Stage entry under 35 U.S.C. § 371 of International Application No. PCT/US2012/021909, filed Jan. 19, 2012, which is a continuation-in-part of International Application No. PCT/US2011/050381, filed Sep. 2, 2011, which claims priority to U.S. Provisional Application No. 61/379,643, filed Sep. 2, 2010, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. AR057515 awarded by the National Institutes of Health. The Government has certain rights in this invention.

BACKGROUND OF THE INVENTION

Osteoporosis is a disease of increased bone fragility that results from estrogen deficiency and aging. It is a major public health problem with nearly 50% of Caucasian women and 25% of Caucasian men at risk for an osteoporotic fracture in their lifetimes (Publication from National Osteoporosis Foundation). Accordingly, osteoporosis represents a significant health concern.

A decrease in the number of mesenchymal stem cells (MSCs) in the bone marrow with aging leads to reduced osteogenesis and may be the most important factor responsible for reduced bone formation and increase bone fragility (Heersche, J. N., C. G. Bellows, and Y. Ishida, *J Prosthet Dent*, 1998, 79(1): p. 14-6.; Ettinger, M. P., *Arch Intern Med*, 2003. 163(18): p. 2237-46). Currently, nearly all of the treatments for osteoporosis reduce bone loss by decreasing osteoclastic bone resorption and thereby preventing the further breakdown of bone. Importantly, this class of drugs does not restore the lost bone structure. Therapeutic modalities that target bone formation by either increasing the number and or the activity of osteoblasts may be a more attractive approach that will enhance bone formation and promote bone regeneration. Although bone regeneration by induction of osteogenesis from MSCs is a rational strategy to treat osteoporosis, systemic infusions of MSCs in vivo has failed to promote an osteogenic response in bone due to the inability of MSCs to migrate to the bone surface which is a major clinical problem for MSC transplantation (Gao, J., et al., *Cells Tissues Organs*, 2001. 169(1): p. 12-20; Meyerrose, T. E., et al., *Stem Cells*, 2007, 25(1): p. 220-7). In addition, engraftment of the MSCs requires donor ablation using chemotherapy and/or radiation which may result in concomitant damage to endogenous mesenchymal cells (Bacigalupo, A., *Best Pract Res Clin Haematol*, 2004, 17(3): p. 387-99).

Cell adhesion is a process by which cells associate with each other, migrate towards a specific target, or localize within the extracellular matrix. Cell adhesion constitutes one of the fundamental mechanisms underlying numerous biological phenomena. Investigations into the molecular basis for cell adhesion have revealed that various cell surface macromolecules, collectively known as cell adhesion molecules or receptors, mediate cell-cell and cell-matrix interactions. For example, members of the integrin family of cell surface receptors mediate cell-cell and cell-matrix interactions and regulate cell motility, migration, survival, and proliferation (Hynes, *Cell*, 69: 11-25 (1992); Hynes, *Cell*, 1110:673-687 (2002)). Integrins are non-covalent heterodimeric complexes consisting of two subunits, $\alpha$ and $\beta$. There are at least 18 different $\alpha$ subunits and at least 8 different $\beta$ subunits.

Mesenchymal stem cells within the bone marrow have a multi-lineage potential and represent a mixture of precursors for mesenchymal-derived cell types including osteoblasts, chondrocytes and adipocytes (Owen, M. et al., *Ciba Found Symp*, 1988, 136: p. 42-60; Bruder, S. P., et al., *J Cell Biochem*, 1994, 56(3): p. 283-94; Prockop, D. J., *Science*, 1997, 276(5309): p. 71-4). Bone cells at all maturation stages rely heavily on cell-matrix and cell-cell interactions (Mukherjee, S., et al., *J Clin Invest*, 2008, 118(2): p. 491-504; Grzesik, W. J. and P. G. Robey, *J Bone Miner Res*, 1994, 9(4): p. 487-96; Vukicevic, S., et al., *Cell*, 1990, 63(2): p. 437-45; Mbalaviele, G., et al., *J Bone Miner Res*, 2006, 21(12): p. 1821-7). Bone marrow is the site where the committed osteoblast progenitors reside, and the osteogenic differentiation is the default pathway for MSC lineage commitment (Halleux, C., et al., *J Musculoskelet Neuronal Interact*, 2001, 2(1): p. 71-6; Muraglia, A., et al., *J Cell Sci*, 2000, 113 (Pt 7): p. 1161-6). Mobilization of the osteoblastic progenitors to the bone surface is a critical step for the osteoblasts to mature and form mineralized tissue (Adams, G. B., et al., *Nature*, 2006, 439(7076): p. 599-603; Chen, X. D., et al., *J Bone Miner Res*, 2007, 22(12): p. 1943-56). Once the osteoblastic progenitors are "directed" to the bone surface, they synthesize a range of proteins including osteocalcin, osteopontin, bone sialoprotein, osteonectin, collagen-I and fibronectin that will further enhance the adhesion and maturation of osteoblasts (Gronthos, S., et al., *Periodontol 2000*, 2006, 41: p. 188-95; Gronthos, S., et al., *Bone*, 2001, 28(2): p. 174-81; Gronthos, S., et al., *J Bone Miner Res*, 1997, 12(8): p. 1189-97). These interactions are largely mediated by transmembrane integrin receptors that primarily utilize an arginine-glycine-aspartate (RGD) sequence to identify and bind to specific ligands. MSCs express integrins $\alpha 1, 2, 3, 4, 6, 11$, CD51 (integrin $\alpha V$), and CD29 (integrins $\beta 1$) (Brooke, G., et al., *Stem Cells Dev*, 2008). Integrins $\alpha_1\beta_1$, $\alpha_2\beta_1$, $\alpha_v\beta_1$, $\alpha_v\beta_5$, $\alpha_5\beta_1$ and $\alpha_4\beta_1$ are reported to be expressed in the osteoblastic cells (Grzesik, W. J. and Robey, P. G., *J Bone Miner Res*, 1994, 9(4): p. 487-96; Gronthos, S., et al., *Bone*, 2001, 28(2): p. 174-81; Gronthos, S., et al., *J Bone Miner Res*, 1997. 12(8): p. 1189-97; Cowles, E. A., L. L. Brailey, and G. A. Gronowicz, *J Biomed Mater Res*, 2000, 52(4): p. 725-37). Overexpression of $\alpha_4$ Integrin on MSCs has been reported to increase homing of the MSCs to bone (Mukherjee, S., et al., *J Clin Invest*, 2008, 118(2): p. 491-504).

Bisphosphonates are widely used for the treatment of osteoporosis. This class of drugs is also used as a "vehicle" for delivering bone-targeted drugs to osseous tissue as prodrugs based on their biphosphonic moiety. Bisphosphonates have been used to deliver sustained release diclofenac, a non-steroidal anti-inflammatory drug to bone in rats (Hirabayashi, H., et al., *J Control Release*, 2001, 70(1-2): p. 183-91). The bisphosphonate dose needed for this drug-delivery purpose is usually 10-100 fold lower than the doses needed for the treatments of osteoporosis, hypocalcaemia, Paget's disease or metastatic bone cancer.

It is well-understood that bone formation is beneficial for the treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc.

Increasing bone mineralization to treat conditions characterized at least in part by increased bone resorption, such as osteopenia, bone fractures, osteoporosis, arthritis, tumor metastases, Paget's disease and other metabolic bone disorders, using cathepsin K inhibitors and TGF-beta binding proteins, etc., are well-known as shown by U.S. Publication No. 2004/0235728 to Selwyn Aubrey Stoch, published Nov. 25, 2004, and Mary E. Brunkow et al., U.S. Pat. No. 6,489,445 and U.S. Publication No. 2004/0009535, published Jan. 15, 2004. In the Brunkow '445 patent and '535 publication, the TGF-beta binding proteins include Sost polypeptide (full length and short peptide) antibodies that interfere with the interaction between the TGF-beta binding protein sclerostin and a TGF-beta superfamily member, and in particular a bone morphogenic protein. In the Brunkow '445 patent a novel family of human TGF-beta binding proteins and nucleic acids encoding them are recited. The protein binds to at least human bone morphogenic protein-5 and human bone morphogenic protein-6. The aforementioned diseases are due to a systemic loss of bone mineral and thus the administration of the antibody therapeutic is for the systemic (whole body) increase in bone mineral density.

U.S. Publication No. 2006/0165799, published Jul. 27, 2006, teaches a bone-filling composition for stimulating bone-formation and bone-consolidation comprising biocompatible calcium sulfate and viscous biopolymers. The composition is intended to be administered into the missing part of injured bone without diffusing to surrounding organs.

U.S. Publication No. 2005/025604, published Nov. 17, 2005, shows induction of bone formation by mechanically inducing an increase in osteoblast activity and elevating systemic blood concentration of a bone anabolic agent, including optionally elevating systemic blood concentration of an antiresorptive agent.

U.S. Pat. No. 7,576,175, issued Aug. 18, 2009, shows $\alpha_4\beta_1$ integrin ligands that display high binding affinity, specificity, and stability. The ligands comprise a peptide having n independently selected amino acids, wherein at least one amino acid is an unnatural amino acid or a D-amino acid, and wherein n is an integer of from 3 to 20.

U.S. Publication No. 2010/0021379, published Jan. 28, 2010, shows antibody conjugates comprising a targeting agent covalently attached to an antibody or fragment thereof. The targeting agent includes a ligand comprising a peptide or peptidomimetic specific for an integrin receptor such as the $\alpha_4\beta_1$ integrin.

What is needed in the art is new compositions and methods for treating osteoporosis and promoting bone growth. Surprisingly, the present invention meets these and other needs.

BRIEF SUMMARY OF THE INVENTION

In a first embodiment, the present invention provides a compound of Formula I:

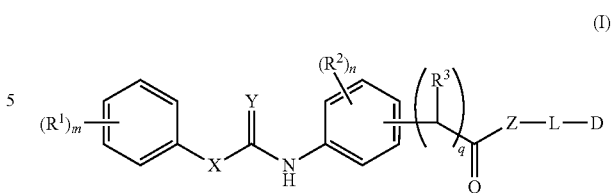

wherein Formula I each $R^1$ and $R^2$ is independently selected from H, halogen, $C_{1-6}$ alkyl, $C_{1-6}$ alkoxy, and $C_{1-6}$ haloalkyl. $R^3$ is selected from H, $C_{1-6}$ alkyl and $C_{3-8}$ cycloalkyl. X is selected from O, S and NH. Y is selected from O and NH. Alternatively, $R^1$ or $R^2$ is combined with Y and the atoms to which they are attached to form a 5-membered heteroaryl ring. Z is a peptide having 3-20 independently selected amino acids, wherein at least one amino acid is selected from an unnatural amino acid and a D-amino acid. L is a linker. D is a bisphosphonate drug. Subscripts m, n and q are each independently from 0 to 2. Also included are salts and isomers of the compounds of Formula I.

In a second embodiment, the present invention provides a pharmaceutical composition including a compound of the present invention and a pharmaceutically acceptable excipient.

In a third embodiment, the present invention provides a method of treating osteoporosis, including administering to a subject in need thereof, a therapeutically effective amount of a compound of the present invention.

In a fourth embodiment, the present invention provides a method of promoting bone growth, including administering to a subject in need thereof, a therapeutically effective amount of a compound of the present invention.

BRIEF DESCRIPTION OF THE DRAWINGS

FIG. 2A: Bone turnover markers measured from the serum. FIG. 2B: Representative histological sections from the lumber vertebral trabecular bone from PBS, MSC, MSC+LLP2A or MSC+LLP2A-Ale-treated groups. Alizarin red was given at 20 mg/kg at baseline and calcein (10 mg/kg) was given subcutaneously 7 days and 2 days before the mice were sacrificed. FIG. 2C: Surface-based bone histomorphometry performed at the $5^{th}$ lumbar vertebral bodies three weeks after the injection and MSC transplantation. ObS/BS, osteoblast surface; MAR, mineral apposition rate; BFR/BS, bone surface-based bone formation rate. *, $p<0.05$ versus PBS; **, $p<0.01$ versus PBS. Data are represented as Mean±SD.

FIG. 3A: Representative cross-sections of the mid-femur from PBS, MSC, MSC+LLP2A, and MSC+LLP2A-Ale-treated groups are shown. Alizarin red was given at 20 mg/kg at baseline (prior to the injection of the study compound) and calcein (10 mg/kg) was given subcutaneously 7 days and 2 days before the mice were sacrificed. FIG. 3B: Surface-based bone histomorphometry, performed at the endocortical surface (Ec) and the periosteal surface (Ps) three weeks after the injections of either MSCs or LLP2A-Ale, is shown. * and ** are as defined above for FIG. 2A-C.

FIG. 4A-B: Representative 3-dimensional thickness maps from microCT scanning of the cancellous bone from the distal femur metaphysic are shown at baseline (A) and after 4 weeks (B). The width of the trabeculae is color coded, the blue-green color represents thin trabeculae and yellow-red color represents thick trabeculae. Representative 3-dimensional thickness maps from each group are shown in the lower panel. FIG. 4C: Percentage changes from baseline (left panel), maximum load (center panel), and maximum stress (right panel) with the different treatments are shown. BV/TV refers to cancellous bone volume/total tissue volume fraction; Tb.Th refers to trabecular thickness. Maximum load and stress were measured at the $6^{th}$ lumbar vertebral body. * and ** are as defined above for FIG. 2A-C.

FIG. 5A: Bone turnover markers measured from the serum for Runx2 and Bglap1 are shown. FIG. 5B: Bone turnover markers measured from the serum for P1NP, osteocalcin, and CTX-1 are shown. FIG. 5C: Surface-based bone histomorphometry, performed on the right distal femurs, is shown. ObS/BS, MAR, BFR/BS, *, and ** are as defined above for FIG. 2A-C.

FIG. 6A: Representative cross-sections of the mid-femur from mice injected with either PBS, LLP2A, Ale, or LLP2A-Ale (10 ng or 250 ng/mouse) are shown. Alizarin red was given at 20 mg/kg at baseline (prior to the injection of the study compound) and calcein (10 mg/kg) was given subcutaneously 7 days and 2 days before the mice were sacrificed. FIG. 6B: Surface-based bone histomorphometry, performed at the endocortical surface (Ec) and the periosteal surface (Ps) four weeks after the injections, is shown. * and ** are as defined above for FIG. 2A-C.

FIG. 10A-C show the synthetic approach of LLP2A-Ale. FIG. 10A: Synthesis of 4-[(N'-2-methylphenyl)ureido]phenylacetic acid (UPA). FIG. 10B: Solid phase synthesis of LLP2A-Lys(D-Cys). FIG. 10C: Preparation of LLP2A-Ale through conjugating LLP2A-Lys(D-Cys) with Ale-Mal.

DETAILED DESCRIPTION OF THE INVENTION

I. General

Figure 1:
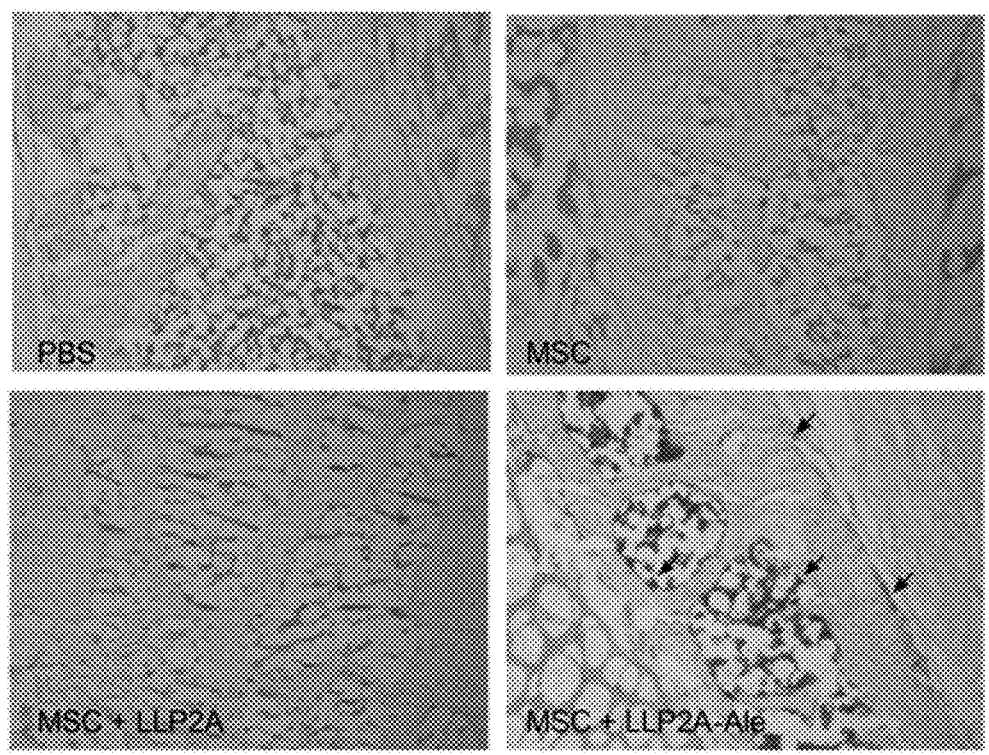
FIG. 1 shows beta-glucuronidase distribution in bone 24-hours following huMSCs transplantation in NOD/SCID/MSPVII mice. Three-month-old MSPVII mice received a single intravenous injection of either of PBS, huMSC ($5 \times 10^5$), huMSC+LLP2A, or huMSC+LLP2A-Ale. The mice were sacrificed 24 hours later. Following sacrifice, lumbar vertebral bodies were harvested and frozen in Optimal Cutting Temperature embedding media. The sections were stained using naphthol-AS-BI-β-Dglucuronide (GUSB) as a substrate. Human MSCs, as showed by GUSB+ red stains (black arrows) were seen accumulated in bone marrow, adjacent to both trabecular and periosteal bone surfaces in huMSCs+LLP2A-Ale group.

The present invention provides compounds and pharmaceutical compositions of a peptidomimetic ligand, e.g. LLP2A, conjugated with a bisphosphonate, e.g. Alendronate. The compounds and pharmaceutical compositions of the present invention are useful for the treatment of osteoporosis, the treatment of low bone mass, the treatment of patient populations characterized by fractured or injured bone, and for the promotion of bone growth due to their specificity for the $\alpha_4\beta_1$ integrin on mesenchymal stem cells and for the surface of bone.

II. Definitions

The abbreviations used herein have their conventional meaning within the chemical and biological arts.

As used herein, the terms "Ale" or "Alen", refer to Alendronate.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the terms "halo" or "halogen," by themselves or as part of another substituent, mean, unless otherwise stated, a fluorine, chlorine, bromine, or iodine atom.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

As used herein, the term "haloalkyl" refers to alkyl as defined above where some or all of the hydrogen atoms are substituted with halogen atoms. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

As used herein, the term "alkoxy" refers to alkyl with the inclusion of an oxygen atom, for example, methoxy, ethoxy, etc.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is phenyl or phenyl mono- or disubstituted by alkyl, heteroalkyl, or halogen.

As used herein, the term "heteroaryl" refers to a monocyclic or fused bicyclic or tricyclic aromatic ring assembly containing 5 to 16 ring atoms, where from 1 to 4 of the ring atoms are a heteroatom. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is oxazolyl, imidazolyl, pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, indazolyl, or any of the radicals substituted, especially mono- or di-substituted.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_{3-8}$cycloalkyl includes cyclopropyl, cyclobutyl, cyclopentyl, cyclohexyl, and up to cyclooctyl.

As used herein, each of the above terms (e.g., "alkyl," "aryl" and "heteroaryl") are meant to include both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR(SO$_2$)R', —CN and —NO$_2$ in a number ranging from zero to (2m'+1), where m' is the total number of carbon atoms in such radical. R', R", R'" and R"" are each independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 10 amino acids in length.

As used herein, the term "amino acid" refers to naturally occurring, unnatural, and synthetic amino acids, as well as amino acid analogs and amino acid mimetics that function in a manner similar to the naturally occurring amino acids.

As used herein, the terms "naturally-occurring amino acids" refer to those amino acids which are encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

As used herein, the terms "unnatural amino acids" include, without limitation, amino acid analogs, amino acid mimetics, synthetic amino acids, N-substituted glycines, and N-methyl amino acids in either the L- or D-configuration that function in a manner similar to the naturally-occurring amino acids. Unnatural amino acids" are not encoded by the genetic code and can, but do not necessarily have the same basic structure as a naturally occurring amino acid.

As used herein, the terms "amino acid analogs" refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

As used herein, the terms "amino acid mimetics" refer to chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

As used herein, the terms "N-substituted glycines" refer to unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs.

Amino acids can be characterized by at least one of several properties. For example, amino acids can be positively charged, negatively charged, hydrophilic, or hydrophobic.

As used herein, the terms "positively charged amino acid" refer to those amino acids having a basic or positively charged side chain at pH values below the pKa, and include, but are not limited to, Lys, Arg, HoArg, Agp, Agb, Dab, Dap and Orn and stereoisomers thereof. Basic amino acids can generally be referred to by the symbol "$X^+$".

As used herein, the terms "negatively charged amino acid" refer to those amino acids having an acidic or negatively charged side chain at pH values above the pKa, and include, but are not limited to, Asp, Glu, Aad, Bec and stereoisomers thereof. Acidic amino acids can generally be referred to by the symbol "$X^-$". One of skill in the art will appreciate that other basic and acidic amino acids are known in the art.

As used herein, the terms "neutrally charged amino acids" refer to those amino acids having a neutrally charged side chain at pH values equal to the pKa.

As used herein, the terms "hydrophilic amino acid" refer to those amino acids having a polar and uncharged side chain and include, but are not limited to, Asn, Ser, Thr, and Gln.

As used herein, the terms "hydrophobic amino acids" refer to those amino acids having a hydrophobic side chain and include, but are not limited to, Val, Leu, Ile, Met, and Phe. Preferably, the hydrophobic amino acid is selected from proline, a proline analog, and a stereoisomer thereof. Preferably, the proline analog is hydroxyproline.

As used herein, the terms "D-amino acids" refer to the D stereoisomer of an amino acid. The letters D and L are conventionally used in the art to refer to the stereoisomers of an amino acid. D-amino acids are those amino acids that could be synthesized from the dextrorotary isomer of glyceraldehyde, i.e. D-glyceraldehyde. Similarly, L-amino acids are those amino acids that could be synthesized from the levorotary isomer of glyceraldehyde, i.e. L-glyceraldehyde.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid. Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic amino acids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

As used herein, the term "linker" refers to a moiety that possesses one or more different reactive functional groups that allows for covalent attachment of moieties such as a peptide to a chelating agent. Preferably, the linking moiety possesses two different reactive functional groups, i.e., a heterobifunctional linker. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached.

Linkers useful in the present invention includes those possessing one or more different reactive functional groups that allow for covalent attachment of moieties such as a peptide to a chelating agent. The linking moiety possesses two or more different reactive functional groups. In some cases multivalent linkers can be used. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker. Some suitable linkers include, but are not limited to, β-alanine, 2,2'-ethylenedioxy bis(ethylamine) monosuccinamide (Ebes) and bis(Ebes)-Lys. Other suitable linkers include those with biotin. Additional linkers can be found in *Bioconjugate Techniques*, Greg T. Hermanson, Academic Press, 2d ed., 2008 (incorporated by reference in its entirety herein).

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic carboxylic acids (acetic acid, propionic acid, glutamic acid, citric acid and the like), organic sulfonic acids (methanesulfonic acid), salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention include salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

As used herein, the term "hydrate" refers to a compound that is complexed to at least one water molecule. The compounds of the present invention can be complexed with from 1 to 10 water molecules.

As used herein, the terms "pharmaceutically acceptable excipient" and "pharmaceutically acceptable carrier" refer to a substance that aids the administration of an active agent to and absorption by a subject. "Pharmaceutically acceptable excipient" refers to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the term "osteoporosis" refers to a disease of increased bone fragility that results from estrogen deficiency and aging.

As used herein, the term "isomers" refers to compounds with the same chemical formula but which are structurally distinguishable.

As used herein, the term "tautomer," refers to one of two or more structural isomers which exist in equilibrium and which are readily converted from one isomeric form to another.

As used herein, the terms "patient" or "subject" refers to a living organism suffering from or prone to a condition that can be treated by administration of a pharmaceutical composition as provided herein. Non-limiting examples include humans, other mammals and other non-mammalian animals.

As used herein, the term "therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

As used herein, the terms "treat", "treating" and "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being.

As used herein, the terms "disorder" or "condition" refer to a state of being or health status of a patient or subject capable of being treated with the glucocorticoid receptor modulators of the present invention.

As used herein, the terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

In some embodiments, the present invention provides a compound of Formula I:

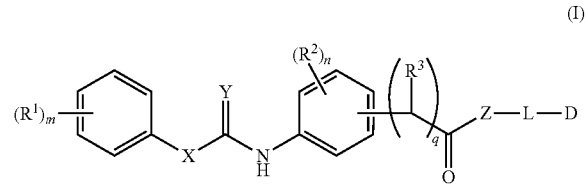

(I)

wherein Formula I each $R^1$ and $R^2$ is independently selected from H, halogen, $C_{1-6}$ alkyl, $C_{1-6}$ alkoxy, and $C_{1-6}$ haloalkyl. $R^3$ is selected from H, $C_{1-6}$ alkyl and $C_{3-8}$ cycloalkyl. X is selected from O, S and NH. Y is selected from O and NH. Alternatively, $R^1$ or $R^2$ is combined with Y and the atoms to which they are attached to form a 5-membered heteroaryl ring. Z is a peptide having 3-20 independently selected amino acids, wherein at least one amino acid is selected from an unnatural amino acid and a D-amino acid. L is a linker. D is a bisphosphonate drug. Subscripts m, n and q are each independently from 0 to 2. Also included are the salts and isomers of the compounds of formula I.

$C_{3-8}$ cycloalkyl groups useful with the present invention include, but are not limited to, cyclopropane, cyclobutane, cyclopentane, cyclohexane, cycloheptane, and cyclooctane. Preferably, $C_{3-8}$ cycloalkyl groups include cyclohexane. 5-membered heteroaryl groups useful with the present invention, include, but are not limited to imidazole, oxazole, isoxazole, thiazole, and isothiazole.

Amino acids useful with the present invention include, without limitation, naturally occurring amino acids; D-amino acids; unnatural amino acids which include, without limitation, amino acid analogs, amino acid mimetics, N-substituted glycines, N-methyl amino acids, phenylalanine analogs, and derivatives of lysine (Lys), ornithine (Orn) and α, γ-diaminobutyric acid (Dbu) in either the L- or D-configuration; hydrophilic amino acids, hydrophobic amino acids; and negatively charged amino acids.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof.

Stereoisomers of a naturally-occurring α-amino acids include, without limitation, D- and L-amino acids. D-amino acids suitable for use in the present invention include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. In some other embodiments, the D-amino acid is selected from a D-α-amino acid, a D-β-amino acid, a D-γ-amino acid, and a combination thereof. In yet another embodiment, the D-α-amino acid is selected from a stereoisomer of a naturally-occurring α-amino acid, an unnatural D-α-amino acid, and a combination thereof.

Unnatural amino acids include, without limitation, amino acid analogs, amino acid mimetics, N-substituted glycines, N-methyl amino acids, phenylalanine analogs, and derivatives of lysine (Lys), ornithine (Orn) and α, γ-diaminobutyric acid (Dbu) in either the L- or D-configuration that function in a manner similar to the naturally-occurring amino acids. Unnatural amino acids are not encoded by the genetic code, and can, but do not necessarily, have the same basic structure or function as a naturally occurring amino acid.

Unnatural amino acids useful with the present invention include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid, thioproline, aminophenylalanine, hydroxytyrosine, and aminotyrosine.

In some other embodiments, the unnatural amino acid is selected from 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine Tyr(3, 5-di NO$_2$), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline ((βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo[3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, a lysine derivative, a ornithine (Orn) derivative, an α, γ-diaminobutyric acid Dbu derivative, stereoisomers thereof, and combinations thereof (see, Liu and Lam, *Anal. Biochem.*, 295:9-16 (2001)). As such, the unnatural α-amino acids are present either as unnatural L-α-amino acids, unnatural D-α-amino acids, or combinations thereof.

In some embodiments, the unnatural amino acids is selected from compounds of Table 1:

TABLE 1

Unnatural amino acids useful with the present invention.

Fmoc-Aad(OtBu)—OH

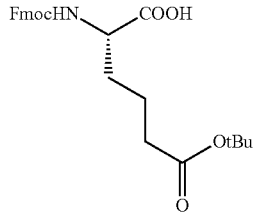

Fmoc-Bec(OtBu)—OH

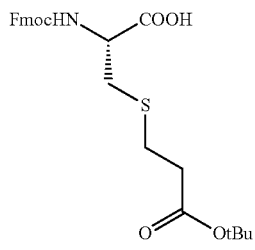

Fmoc-Bmc(OtBu)—OH

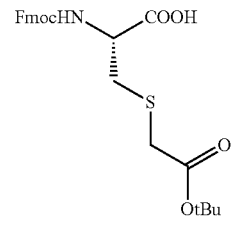

Fmoc-Ach-OH

Suitable amino acid analogs include, without limitation, homoserine, norleucine, methionine sulfoxide, methionine methyl sulfonium.

Suitable amino acid mimetics include, without limitation, β-amino acids and γ-amino acids. Suitable R groups for β- or γ-amino acids include, but are not limited to, side-chains present in naturally-occurring amino acids and unnatural amino acids.

N-substituted glycines suitable for use in the present invention include, without limitation, N-(2-aminoethyl)glycine, N-β-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., *Drug Dev. Res.*, 35:20-32 (1995)). As such, peptoids containing at least one unnatural α-amino acid, D-amino acid, or a combination thereof are within the scope of the present invention.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe(4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Suitable phenylalanine analogs useful with the present invention include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-di Cl)), 3,4-dichlorophenylalanine (Phe(3,4-di Cl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F5)), 3,4,5-trifluorophenylalanine (Phe(F3)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and α, γ-diaminobutyric acid (Dbu) useful with the present invention include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. Derivatives of Orn and Dbu are similar to the lysine derivatives with corresponding carboxylic acid attached to the side chain of Orn and Dbu, respectively.

Suitable hydrophilic amino acids useful with the present invention include, without limitation, Val, Leu, Ile, Met, and Phe and stereoisomers thereof.

Suitable hydrophobic amino acids useful with the present invention include, without limitation, the compounds of Table 2:

TABLE 2

Hydrophobic amino acids useful in the present invention.

| No. | $X_{AA}$ | Structure |
|---|---|---|
| 1 | Ile | H$_2$N–COOH |

TABLE 2-continued

Hydrophobic amino acids useful in the present invention.

| No. | $X_{AA}$ | Structure |
|---|---|---|
| 2 | Ala | H₂N-CH(CH₃)-COOH |
| 3 | Abu | H₂N-CH(CH₂CH₃)-COOH |
| 4 | Leu | H₂N-CH(CH₂CH(CH₃)₂)-COOH |
| 5 | Pra | H₂N-CH(CH₂C≡CH)-COOH |
| 6 | Chg | H₂N-CH(cyclohexyl)-COOH |
| 7 | Nva | H₂N-CH(CH₂CH₂CH₃)-COOH |
| 8 | Phg | H₂N-CH(phenyl)-COOH |
| 9 | Cha | H₂N-CH(CH₂-cyclohexyl)-COOH |
| 10 | Ach | H₂N-C(cyclohexyl)-COOH |
| 11 | Ppca | 5-phenylpyrrolidine-2-carboxylic acid |
| 12 | Ana | H₂N-CH(2-naphthyl)-COOH |
| 13 | Bpa | H₂N-CH(CH₂-C₆H₄-C(O)-C₆H₅)-COOH |
| 14 | Val | H₂N-CH(CH(CH₃)₂)-COOH |
| 15 | Acpc | 1-aminocyclopropane-1-carboxylic acid |
| 16 | Thi | H₂N-CH(CH₂-2-thienyl)-COOH |
| 17 | Nle | H₂N-CH(CH₂CH₂CH₂CH₃)-COOH |
| 18 | D-Nal-2 | H₂N-CH(CH₂-2-naphthyl)-COOH |
| 19 | Aic | 2-aminoindane-2-carboxylic acid |
| 20 | D-Phe | H₂N-CH(CH₂-phenyl)-COOH |

TABLE 2-continued

Hydrophobic amino acids useful in the present invention.

| No. | $X_{AA}$ | Structure |
|---|---|---|
| 21 | HoPhe | H₂N-CH(CH₂-C₆H₅)-COOH |
| 22 | Tyr | H₂N-CH(CH₂-C₆H₄-OH)-COOH |
| 23 | Tyr(Me) | H₂N-CH(CH₂-C₆H₄-OMe)-COOH |
| 24 | Phe(3-Cl) | H₂N-CH(CH₂-C₆H₄-Cl)-COOH |
| 25 | Tyr(diI) | H₂N-CH(CH₂-C₆H₂(I)₂-OH)-COOH |
| 26 | Phe(4-Me) | H₂N-CH(CH₂-C₆H₄-Me)-COOH |

In some other embodiments, the hydrophobic amino acid is selected from compounds of Table 3:

TABLE 3

Hydrophobic amino acids useful in the present invention.

| No. | $X_{AA}$ | Structure |
|---|---|---|
| 1 | Nle | H₂N-CH(CH₂CH₂CH₂CH₃)-COOH |
| 2 | Leu | H₂N-CH(CH₂CH(CH₃)₂)-COOH |
| 3 | Pra | H₂N-CH(CH₂-C≡CH)-COOH |
| 4 | HLe | H₂N-CH(CH₂CH₂CH(CH₃)₂)-COOH |
| 5 | Cpa | H₂N-CH(CH₂-cyclopropyl)-COOH |
| 6 | Cha | H₂N-CH(CH₂-cyclohexyl)-COOH |

In some other embodiments, the hydrophobic amino acid is independently selected from leucine (Leu), a leucine analog, phenylalanine (Phe), a phenylalanine analog, proline (Pro), a proline analog, valine (Val), isoleucine (Ile), glycine (Gly), alanine (Ala), Met, norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ana), 3,5-dinitrotyrosine (Tyr(3,5-di NO₂)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO₂)), 1-amino-1-cyclohexane carboxylic acid (Ach), 2-aminoindane-2-carboxylic acid (Aic), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), and a stereoisomer thereof. Preferably, the proline analog is hydroxyproline.

Suitable negatively charged amino acids useful with the present invention include, without limitation, aspartic acid, glutamic acid, α-aminohexanedioic acid, α-aminooctanedioic acid, homoaspartic acid, γ-carboxy-glutamic acid, 4-carboxyphenylalanine, and a stereoisomer thereof. In other embodiments, the negatively charged amino acid is selected from Aad, Bec and Bmc.

Bisphosphonate drugs useful with the present invention include any suitable bisphosphonate compound. Exemplary bisphosphonate drugs include, but are not limited to, Etidronate (Didronel), Clodronate (Bonefos, Loron), Tiludronate (Skelid), Pamidronate (APD, Aredia), Neridronate, Olpadronate, Alendronate (Fosamax), Ibandronate (Boniva), Risedronate (Actonel) and Zoledronate (Zometa). Additional bisphosphonates are described below in greater detail. One of skill in the art will appreciate that other bisphosphonates are useful in the present invention.

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, lithium salts, and potassium salts; alkaline earth metal salts such as calcium salts, and magnesium salts; aluminum salts; and ammonium salts, such as ammonium, trimethyl-ammonium, diethylammonium, and tris-(hydroxymethyl)-methyl-ammonium salts. Other salts with organic bases include salts with diethylamine, diethanolamine, meglumine, and N,N'-dibenzylethylenediamine.

Linkers useful in the present invention includes those possessing one or more different reactive functional groups that allow for covalent attachment of moieties such as a peptides, monomers, and polymers. The linking moiety possesses two or more different reactive functional groups. In some cases multivalent linkers can be used and multiple peptides of the present invention and/or multiple active agents can be linked via the linker. Suitable linkers include, without limitation, those available from Pierce Biotechnology, Inc. (Rockford, Ill.). One skilled in the art understands that any reactive functional group can be present on the linker, as long as it is compatible with a functional group on the moiety that is to be covalently attached. Some suitable linkers include, but are not limited to, β-alanine, 2,2'-ethylenedioxy bis(ethylamine) monosuccinamide (Ebes), bis(Ebes)-Lys, and polyethylene glycol. Other suitable linkers include those with biotin. Additional linkers can be found in *Bioconjugate Techniques*, Greg T. Hermanson, Academic Press, 2d ed., 2008 (incorporated by reference in its entirety herein).

A person of ordinary skill in the art will recognize that other linkers are possible with the compounds of the present invention. Many such linkers can be found in, or prepared by the techniques recited in, "Bioconjugate Techniques" by Greg T Hermanson, Academic Press, San Diego, 1996, which is hereby incorporated by reference. Furthermore, a person of ordinary skill in the art will recognize that other linkers can be prepared based on Click Chemistry synthetic techniques as described in Kolb, H. C., Finn, M. G., Sharpless, K. B., Angew. Chem. Int'l. Ed. 40 (11): 2004-2021 (2001), which is hereby incorporated by reference. Linkers useful with the present invention include those based on the EBES and PEG moiety. The linker can include either 0 to 6 EBES or PEG groups. EBES and PEG groups can be conjugated by the techniques referenced above.

Acid addition salts, such as mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In some embodiments, the portion of the compound bonded to Z of Formula I has a formula selected from:

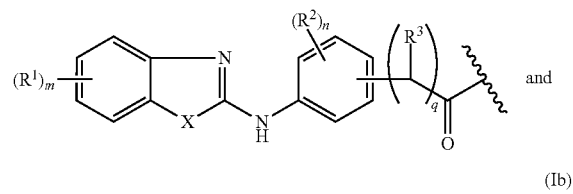

(Ia)

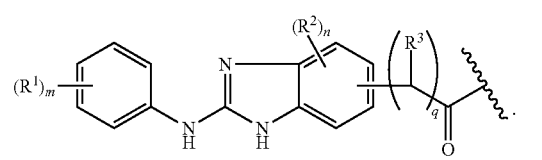

(Ib)

In some other embodiments, the portion of the compound of Formula I bonded to Z has a formula selected from:

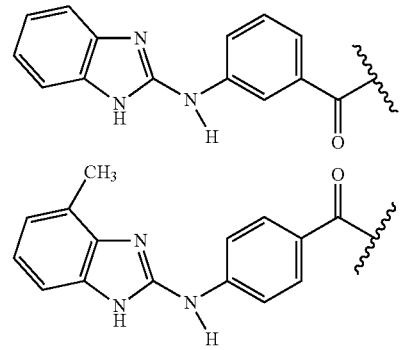

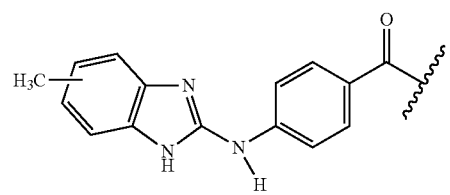

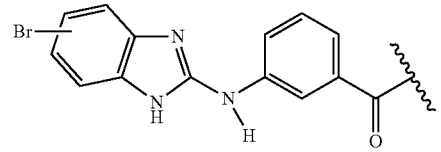

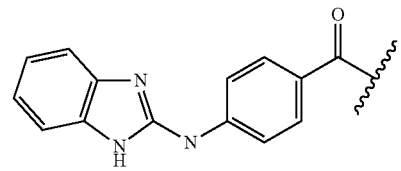

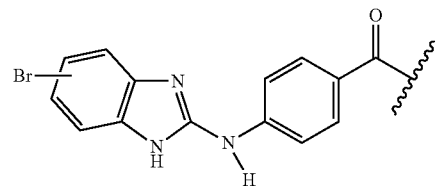

-continued
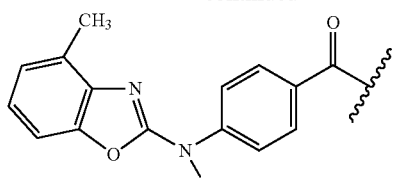
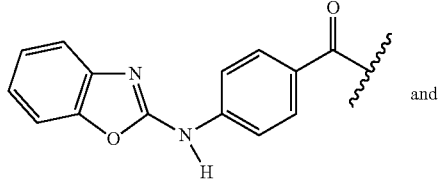
and
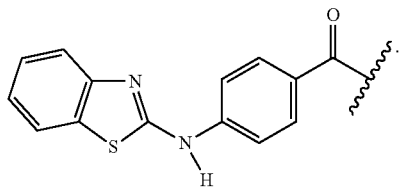
.
In some embodiments, the portion of the compound of Formula I bonded to Z has a formula selected from:
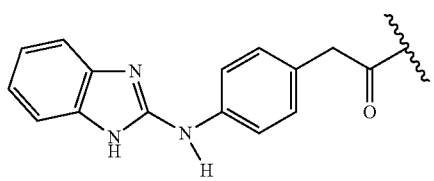
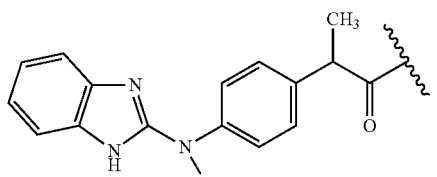
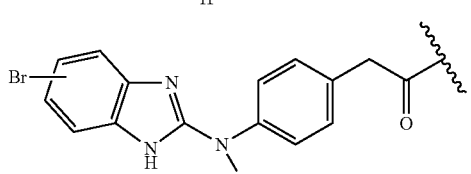
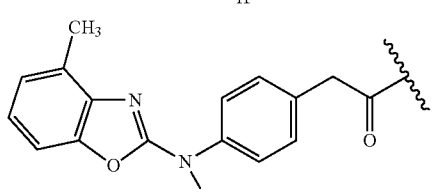
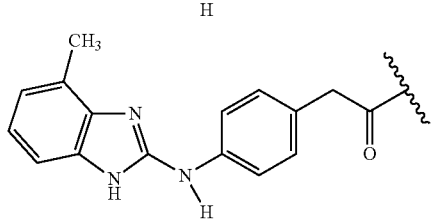
-continued
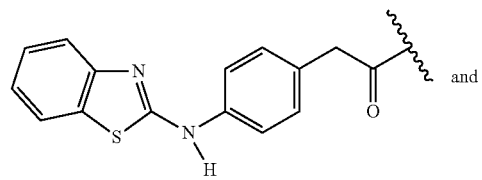
and
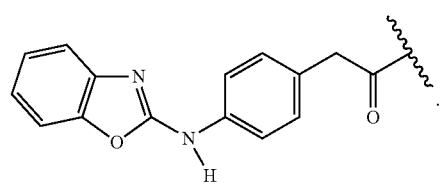
.
In some other embodiments, the portion of the compound of Formula I bonded to Z has a formula selected from:
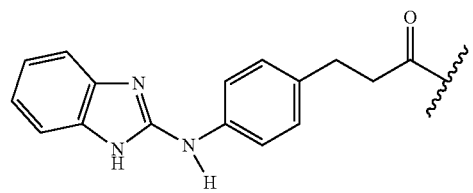
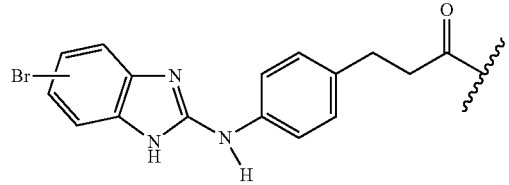
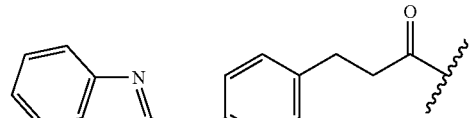
and
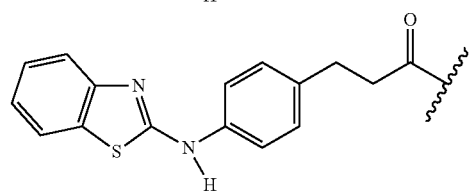
.
In some embodiments, the portion of the compound of Formula I bonded to Z has a formula selected from:
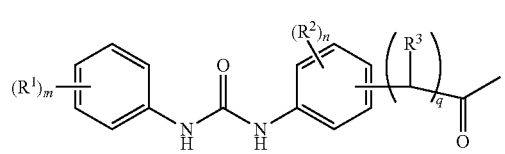
(Ic)

-continued and

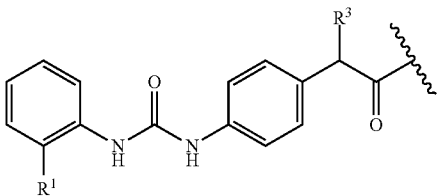

In some other embodiments, the portion of the compound of Formula I bonded to Z has the formula:

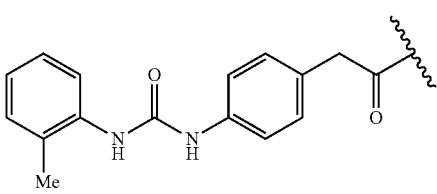

In some embodiments, peptide Z has the following structure:

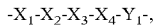

wherein $X_1$ can be a hydrophobic amino acid or derivatives of lysine, ornithine (Orn) and α,γ-diaminobutyric acid (Dbu); $X_2$ can be a negatively charged amino acid; $X_3$ can be a hydrophobic amino acid; $X_4$ can be a naturally-occurring amino acid, an unnatural amino acid, or a D-amino acid; $Y_1$ can be a peptide fragment having m independently selected amino acids; and m is an integer of from 0 to 20. In another embodiment, m is an integer of from 0 to 15, preferably of from 0 to 10, more preferably of from 0 to 5, and still more preferably of from 0 to 3. In another embodiment, $Y_1$ has a carboxyl-terminal group selected from the group consisting of an amide group and a carboxylic acid group.

In some other embodiments, peptide Z has the following structure:

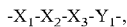

wherein $X_1$, $X_2$, $X_3$ and $Y_1$ are as defined above.

In other embodiments, peptide Z of Formula I has the formula:

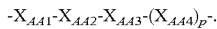

$X_{AA1}$ is selected from a hydrophobic amino acid and derivatives of lysine, homolysine (Hly), ornithine (Orn) and α,γ-diaminobutyric acid (Dbu). $X_{AA2}$ is a negatively charged amino acid. $X_{AA3}$ is a hydrophobic amino acid. $X_{AA4}$ is selected from a naturally-occurring amino acid, an unnatural amino acid, and a D-amino acid. Subscript p is 0 or 1. Suitable hydrophobic amino acids, derivatives of lysine, homolysine (Hly), ornithine (Orn) and α,γ-diaminobutyric acid (Dbu), negatively charged amino acids, naturally-occurring amino acids, unnatural amino acids, and D-amino acids useful with the present invention are described above.

In other embodiments, $X_{AA1}$ can be Leu, a leucine analog, Lys38, or a stereoisomer thereof. In another embodiment, $X_{AA2}$ can be Asp, Glu, Aad, or a stereoisomer thereof. In a preferred embodiment, $X_{AA2}$ is Aad. In yet another embodiment, $X_{AA3}$ can be Leu, a Leu analog, Phe, a Phe analog, Val, Ile, Ala, Nva, Acpc, Chg, Aib, Abu, Aic, NaI-2, Ana, or a stereoisomer thereof. In still yet another embodiment, $X_{AA4}$ can be a hydrophobic amino acid, a negatively charged amino acid, or a stereoisomer thereof. Preferably, the hydrophobic amino acid can be Pro, a Pro analog, or a stereoisomer thereof. Preferably, the Pro analog is Hyp.

In another embodiment, peptide Z can be -Nle-Aad-Chg-D-Tyr, -Leu-Aad-Chg-D-Gln-D-Tyr, -Cpa-Asp-Phg-D-Glu-D-Ser, -Leu-Aad-Val-Hyp (SEQ ID NO:1), -Nle-Aad-Val-D-Thr-Hyp-D-Asn, -Cha-Aad-Nle-D-Gln-D-Asn, -Cpa-Glu-Val-D-Asp-D-Ala, -Hle-Aad-Phe-Chg (SEQ ID NO:2), -Nle-Asp-Pra-Gly-Hyp (SEQ ID NO:3), -Lys38-Aad-Leu-D-Pro, -Cha-Asp-Val-D-Glu-D-Gln, -Cpa-Aad-Ile-D-Asp, -Hle-Aad-Aib-D-3-Pal, -Lys38-Glu-Acpc-Nle-D-Asp-D-Gln, -Nle-Asp-Val-Ach-D-Ala, -Leu-Aad-Ala-Hyp, -Cpa-Asp-Nva-D-Glu, -Leu-Aad-Nva-Hyp-D-Glu, -Hle-Asp-Ile-D-Asp-HoSer-D-Asn, -Cpa-Aad-Aib-D-Thi, -Cpa-Aad-Acpc-Hyp (SEQ ID NO:4), -Cpa-Aad-Val-D-Tyr-D-Asp, -Nle-Asp-Ala-Aad-Aic (SEQ ID NO:5), -Cha-Asp-HoPhe-Hyp-D-3-Pal-Nle-Ach, -Nle-Aad-Chg-Hyp-Aad (SEQ ID NO:6), -Nle-Aad-Chg-Hyp-D-Val-D-Asp-D-Asp, -Cpa-Aad-Chg-Pro-Aad-Phe(3-Cl)-Aad (SEQ ID NO:7), -Cpa-Aad-Chg-Acpc-D-Asp-D-Glu, -Nle-Aad-Chg-Hyp-D-Glu-Ach, -Hle-Aad-Val-Hyp-Chg (SEQ ID NO:8), -Nle-Glu-Phg-Acp-Aad (SEQ ID NO:9), -Nle-Aad-Val-D-Glu, -Lys38-Aad-Acpc-D-Asp, -Lys38-Aad-Acpc-D-Asn-D-Asn, -Lys38-Aad-D-Phe-D-3-Pal, -Nle-Aad-Cha-D-Gln, -Hle-Aad-Ile-D-Asp-Nle, -Lys38-Aad-Aic-D-Glu-D-Tyr, -Cpa-Aad-Nle-D-Pro, -Lys-Aad-Chg-D-Glu, -Cpa-Aad-Chg-D-Ser-Gly, -Cpa-Aad-Nle-Aad (SEQ ID NO:10), -Cpa-Aad-Acpc-Aad (SEQ ID NO:11), -Leu-Aad-Acpc-Aad (SEQ ID NO:12), -Nle-Aad-Nle-Chg-D-Glu, -HoPhe-Aad-D-Nal-2-D-Glu, -Lys38-Aad-D-Phe-4-Pal-D-Asn, -Lys38-Aad-D-Phe-D-Asp, -Lys38-Aad-D-Phe-D-Ser-Nva, or -Lys38-Aad-D-Phe-D-Val.

In some other embodiments, peptide Z can be -HoPhe-Asp-Phg-Pro-Gly-D-Tyr-Aad, -Hle-Asp-Ile-Pro-Chg (SEQ ID NO:13), -Cpa-Asp-Ile-Hyp-D-Thr-D-Asn-Nva, -Cha-Asp-Pra-Pro-D-Pro-Gly-D-Ser, -Cha-Asp-Leu-Hyp-HoCit-HoCit (SEQ ID NO:14), -Lys12-Aad-Nva-Hyp-Hyp (SEQ ID NO:15), -Hle-Asp-Val-Pro-D-3-Pal-Nva-Ana, -Cpa-Asp-Abu-Acp-Nva-D-Asp, -Cha-Asp-Tyr-Pro-D-His, -Leu-Aad-Abu-Ppca-Ach-D-Tyr, -Leu-Asp-Nva-Hyp-Gly-D-Phe-Nva, -Nle-Asp-Ile-Pro-Aib-D-HoPhe-Tyr(Me), -Cpa-Glu-Tyr-Pro-Chg-Aad-D-Glu, -Hle-Asp-Nva-Pro-D-Glu, -Nle-Asp-Ile-Hyp-Hyp (SEQ ID NO:16), -Ile-Aad-Ile-Ppca-D-Ile, -HoPhe-Asp-Ala-Pro-Aib-D-Ala, -Hle-Glu-Abu-Hyp-HoCit-HoCit (SEQ ID NO:17), -Leu-Asp-Leu-Ppca-HoCit-D-Thr-D-Pro, -HoPhe-Asp-Nva-Ppca-D-Ala, -Nle-Asp-Val-Pro-HoCit-Gly (SEQ ID NO:18), -Cpa-Aad-Abu-Pro-D-Ala-D-Tyr-D-Phe(4-Me), -Nle-Glu-Ala-D-Thi, -Cha-Asp-Nle-D-Gln, -Hle-Aad-Ile-D-Asp-D-Phe, -Leu-Asp-D-Phe-Aic, -Cpa-Asp-Leu-D-Thi, -HoPhe-Asp-Abu-D-Asn, -Cha-Aad-Val-Ana-Ahch (SEQ ID NO:19), -Hle-Asp-Acpc-D-Ala, -Leu-Aad-Ana-D-Pro, -Lys38-Asp-Phe(3-Cl)-D-Pro, -Lys 12-Asp-Nle-Hyp-D-Glu, -Lys38-Aad-D-Nal-2-D-Thr-D-Bpa, -Cpa-Asp-Ala-D-Thi, or -HoPhe-Asp-Ala-Hyp (SEQ ID NO:20).

In some embodiments, $X_{AA1}$ of peptide Z of Formula I is lysine-A38 (Lys38), $X_{AA2}$ of peptide Z of Formula I is α-aminohexanedioic acid (Aad), $X_{AA3}$ of peptide Z of Formula I is a D-amino acid, and subscript p is 0. In some other embodiments, peptide Z of Formula I is selected from -Lys38-Aad-D-Phe, -Lys38-Aad-Ach, -Lys38-Aad-D-NaI-2, -Lys38-Aad-Ile, -Lys38-Aad-Val, and -Lys38-Aad-Leu. In other embodiments, the present invention provides compounds of Formula I, wherein peptide Z is -Lys38-Aad-Ach.

In some embodiments, the linker L of Formula I includes at least one of N-(8-amino-3,6-dioxa-octyl)succinamic acid (EBES) and polyethylene glycol (PEG).

In some other embodiments, the linker L of Formula I is selected from:
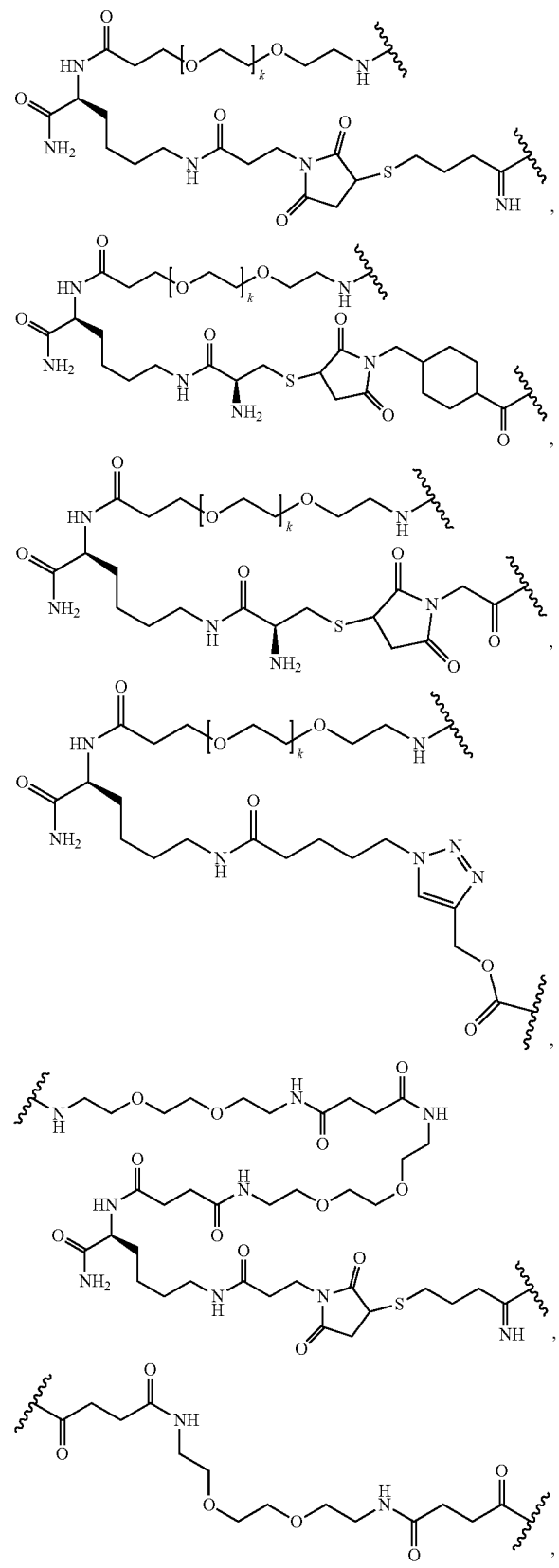
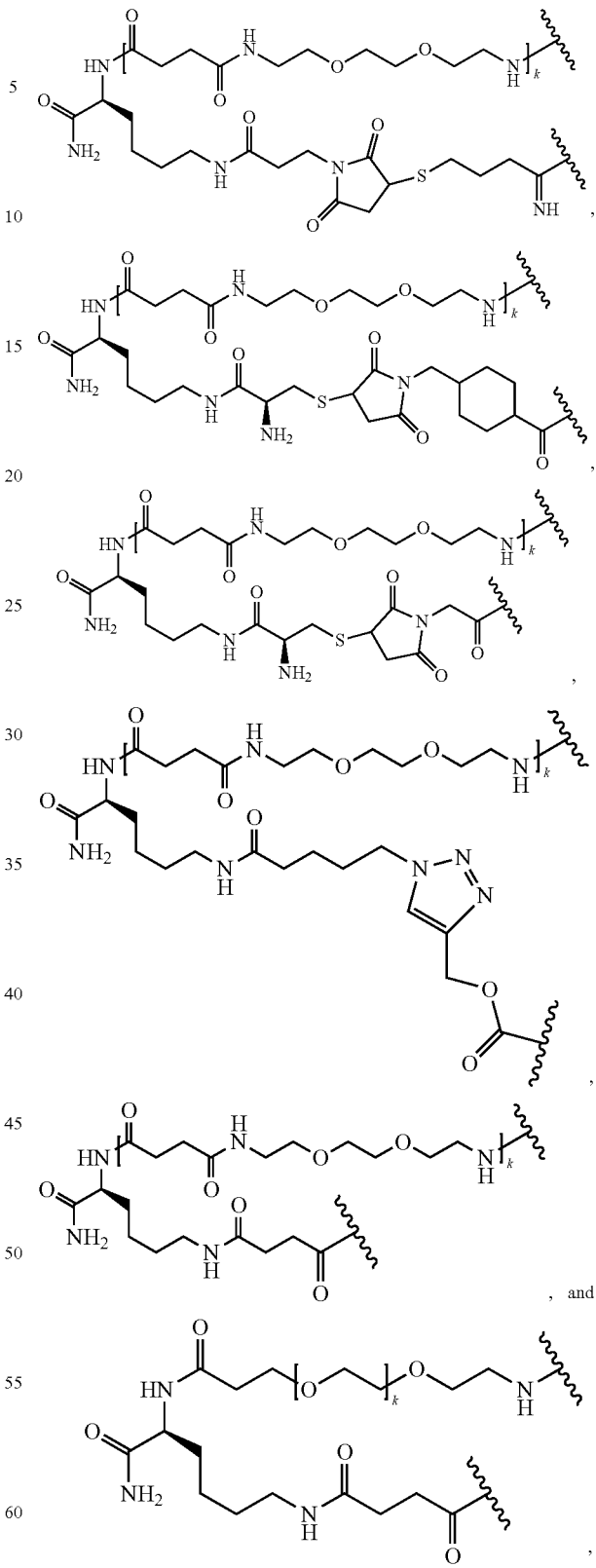
wherein k is from 0 to 6.
In some embodiments, the portion of the compound of Formula I bonded to D of Formula I has the formula:

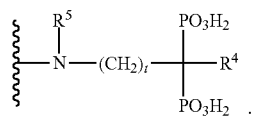
$R^4$ is selected from H, OH and halogen, $R^5$ is selected from H and $C_{1-6}$ alkyl, and subscript t is from 1 to 6.
In some other embodiments, the portion of the compound of Formula I bonded to D has the formula selected from:
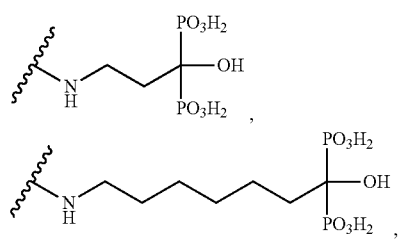
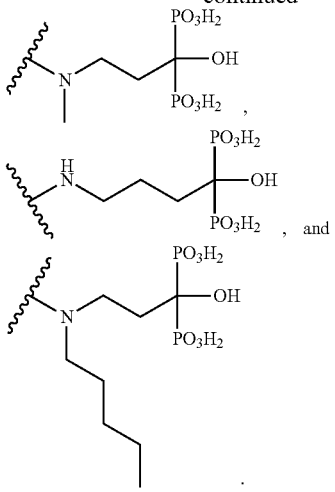
In some embodiments, the compounds of Formula I are selected from:
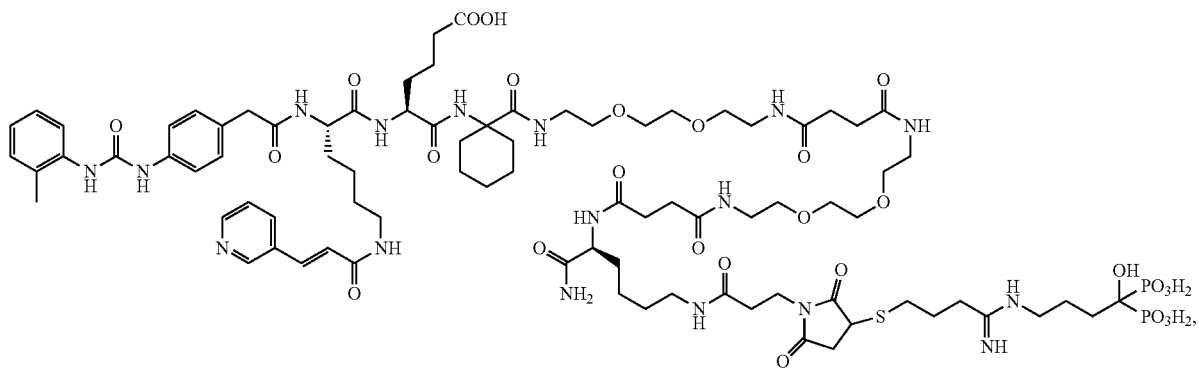
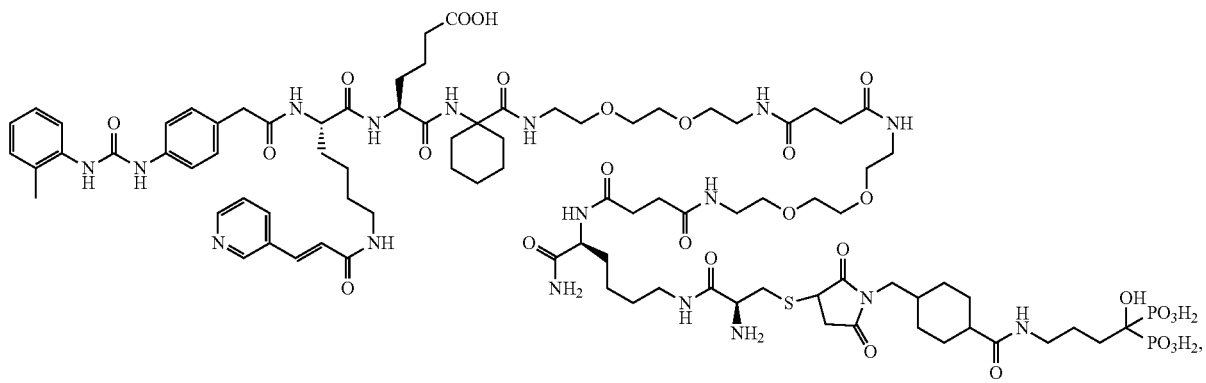

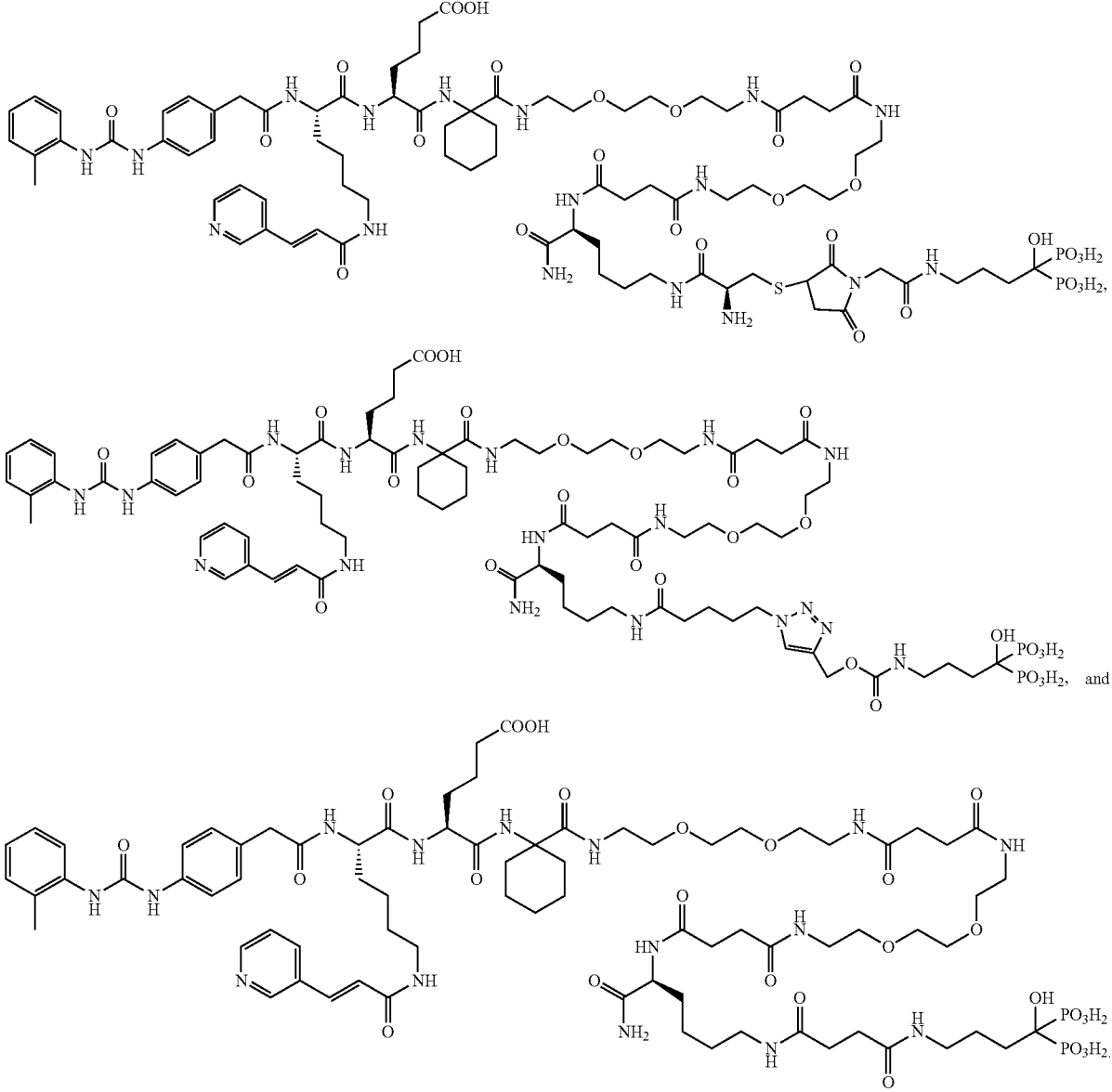

In some embodiments, the salts, hydrates, solvates, prodrug forms, isomers, and metabolites of compounds of Formula I are provided.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see Comprehensive Organic Transformations by Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention.

One-bead one-compound (OBOC) combinatorial library methods were used to identify bisaryl urea peptidomimetics, such as LLP2A, as highly potent and selective ligands for the activated form of $\alpha_4\beta_1$ integrin (Peng, L., et al., Nat Chem Biol, 2006, 2(7): p. 381-9). Additionally, LLP2A, when appropriately radioconjugated (DOTA/$^{64}$Cu or $^{90}$Y), was shown to exhibit potential as a diagnostic or therapeutic agent (DeNardo et al., J Nucl Med, 2009, 50: p 625-34).

The "one-bead one-compound" (OBOC) combinatorial library method was first reported in 1991 (Lam et al., Nature, 1991, 354:p. 82-4). In essence, when a "split-mix" synthesis method (Lam et al., id; Houghten et al., Nature, 1991, 354:p. 84-6; Furka et al., Int. J. Peptide Protein Res., 1991, 37:p. 487-93) is used to generate a combinatorial library, each bead expresses only one chemical entity (Lam et al., id; Lam et al., Chem. Rev., 1997, 97:p. 411-48). Random libraries of millions of beads can then be screened in parallel for a specific acceptor molecule (e.g., receptor, antibody, enzyme, virus, whole cell, etc.). Positive beads are physically isolated for structural determination by microsequencing using automatic Edman degradation (Lam et al., Nature, 1991, 354:p. 82-4).

The one-bead-one compound (OBOC) combinatorial library method synthesizes millions of compounds such that each bead displays only one compound. Through the OBOC combinatorial library methods, LLP2A was identified as a ligand that specifically binds to the integrin $\alpha_4\beta_1$ (IC$_{50}$=2 pM). LLP2A, when conjugated a to near-infrared fluorescent dye, can be used to image $\alpha_4\beta_1$-expressing cells with high sensitivity and specificity and to guide a therapeutic compound to the $\alpha_4\beta_1$-expressing lymphomas (Peng, L., et al., Nat Chem Biol, 2006, 2(7): p. 381-9). The ligand is known to direct compounds to the $\alpha_4\beta_1$-expressing lymphomas (Peng, L., et al., Nat Chem Biol, 2006, 2(7): p. 381-9; Peng, L., et al., Mol Cancer Ther, 2008, 7(2):p. 432-7 Aina, O. H., et al., Mol Pharm, 2007. 4(5): p. 631-51; Aina, O. H., et al., Mol Cancer Ther, 2005. 4(5): p. 806-13.).

The compounds described herein can be used in combination with one another, with other active agents known to be useful in treating osteoporosis or promoting bone growth, or with adjunctive agents that may not be effective alone, but may contribute to the efficacy of the active agent. In some embodiments, co-administration of the compounds herein with other agents includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, active agents can be formulated separately. In another embodiment, the active and/or adjunctive agents may be linked or conjugated to one another.

Figure 12:
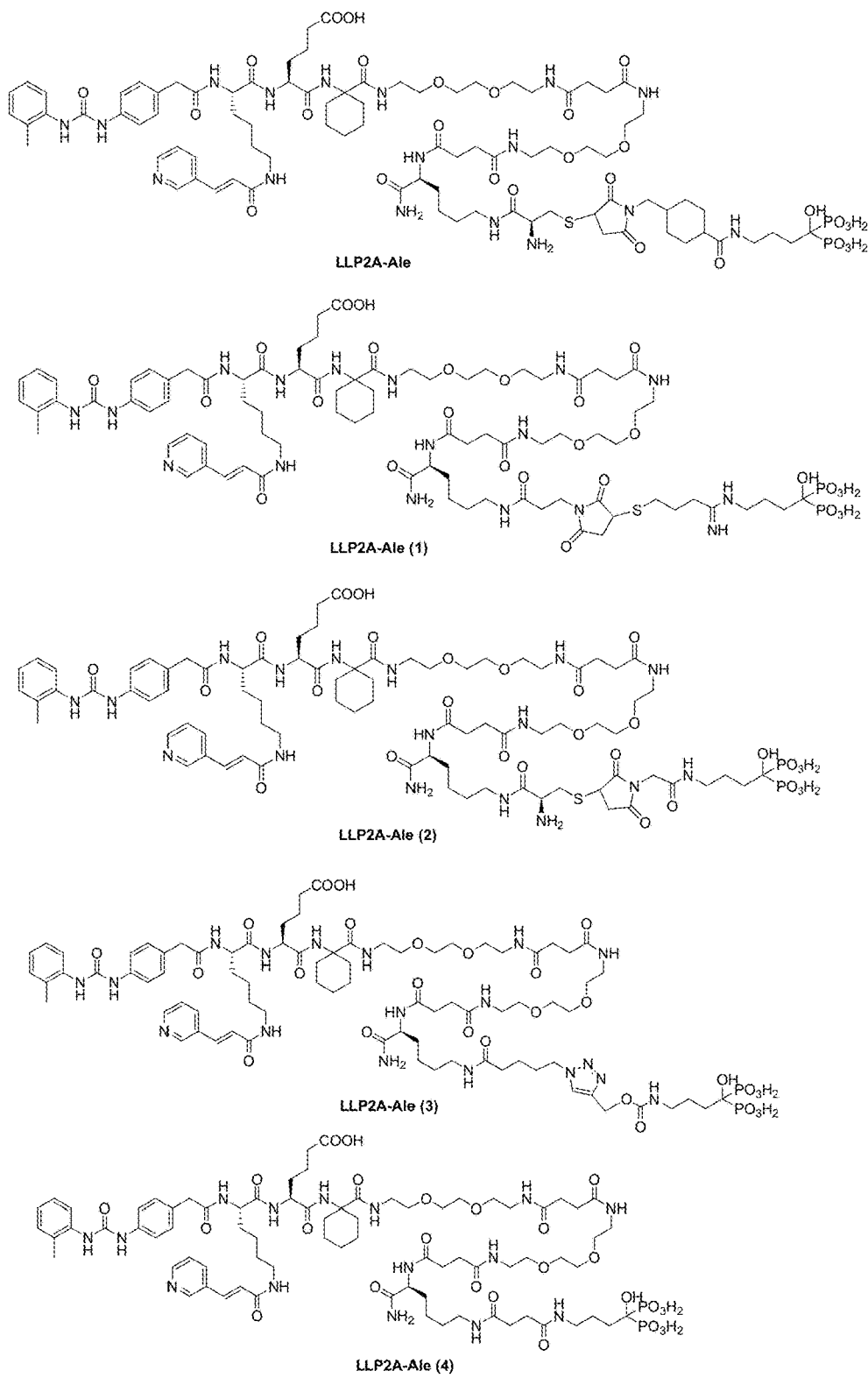
FIG. 12 shows exemplary compounds of the present invention.
Figure 13A:
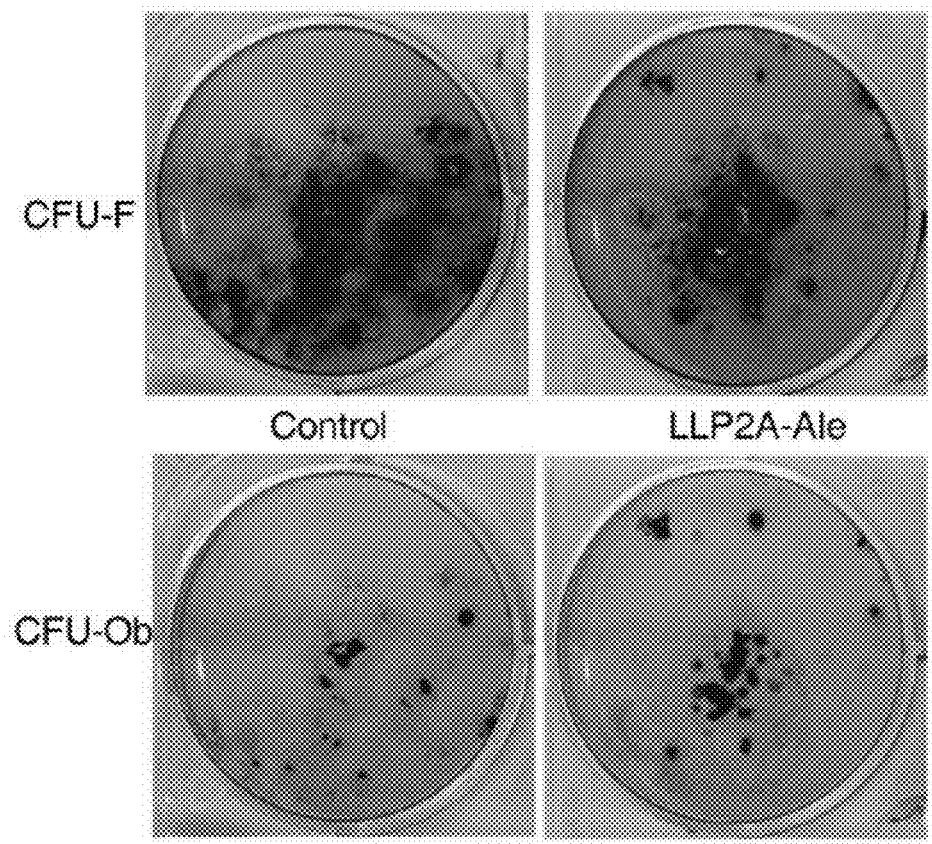
FIG. 13A-B show LLP2A-Ale increases MSC osteoblast maturation, function and migration without affecting their chondrogenic or adipogenic potentials.
Figure 13B:
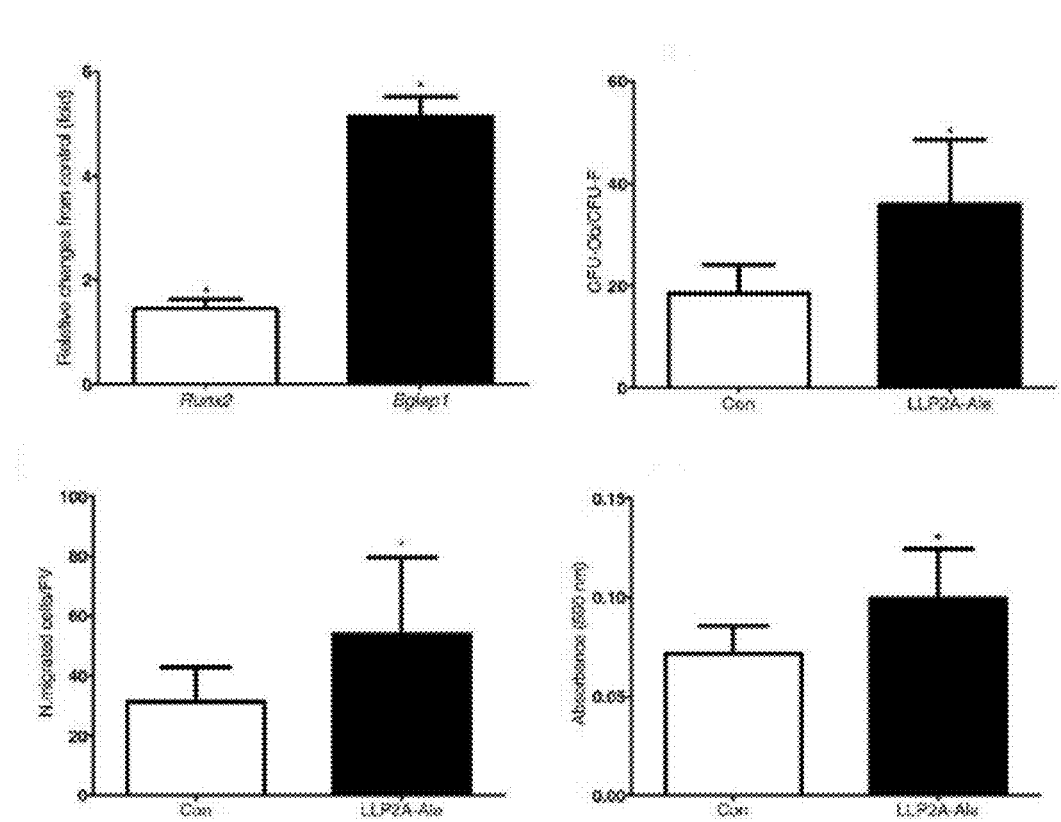
Figure 14A:
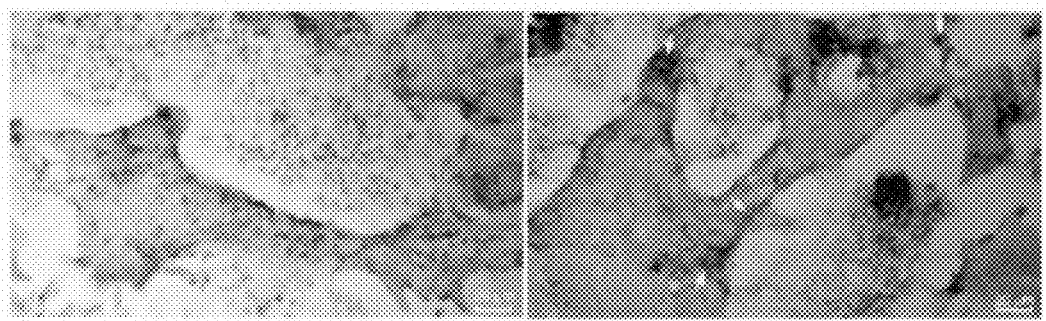
FIG. 14A-C show retention of the transplanted huMSCs in bone 3-weeks following co-injection in mice with LLP2A-Ale and huMSCs (FIG. 14A), and increased osteoblasts and osteocytes at cortical (FIG. 14B) and trabecular (FIG. 14C) bong regions in lumbar vertebral bodies (LVB) 3 weeks following co-injection in mice with LLP2A-Ale and GFP-labeled huMSCs.
Figure 14B:
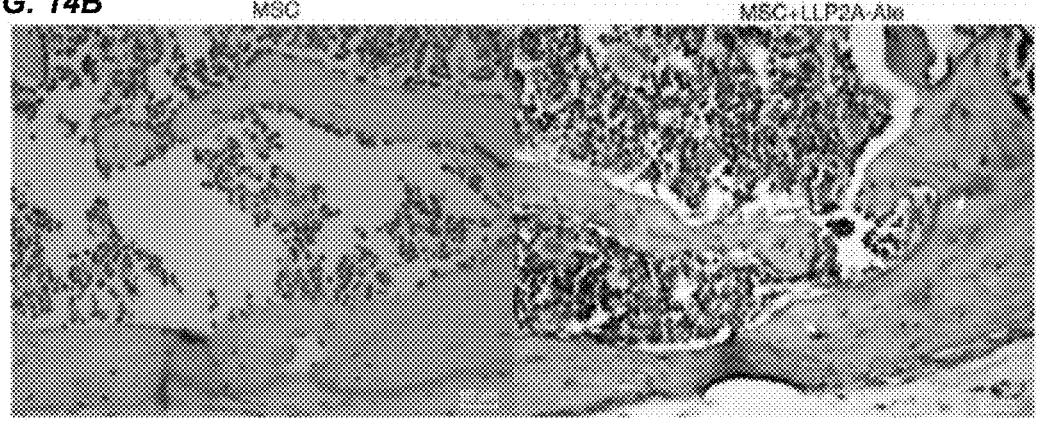
Figure 14C:
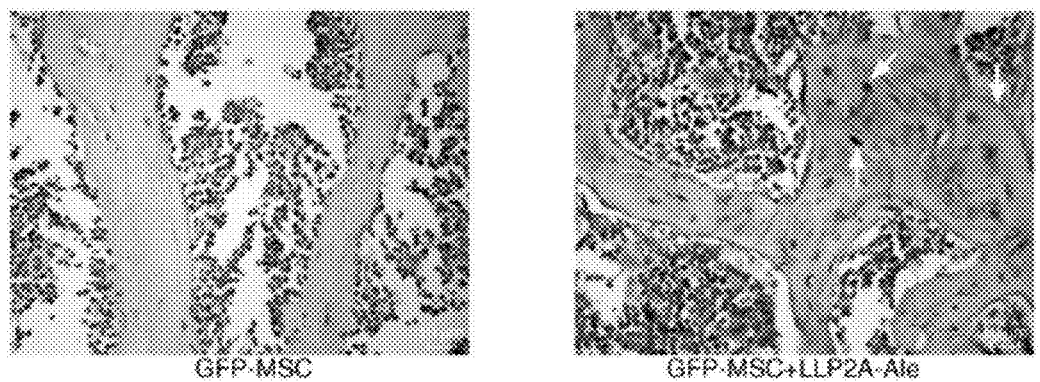
Figure 15:
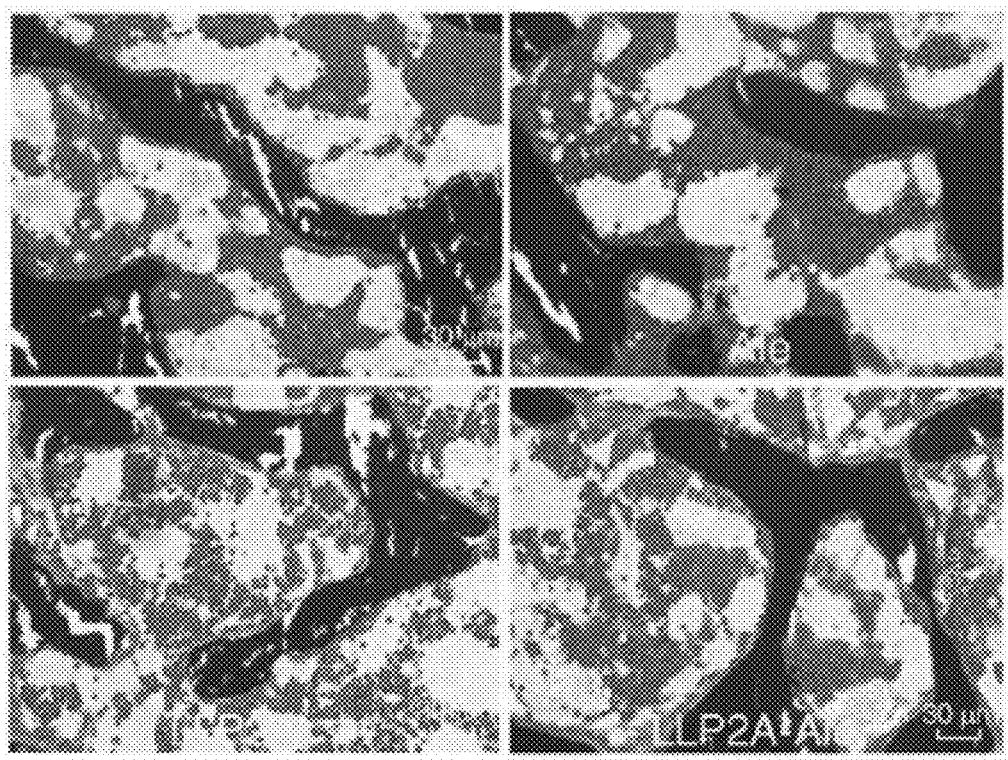
FIG. 15 shows LLP2A-Ale treatment increased osteoblast surface and formed bridges between adjacent trabeculae in immunocompetent mice (129SvJ).
Figure 16A:
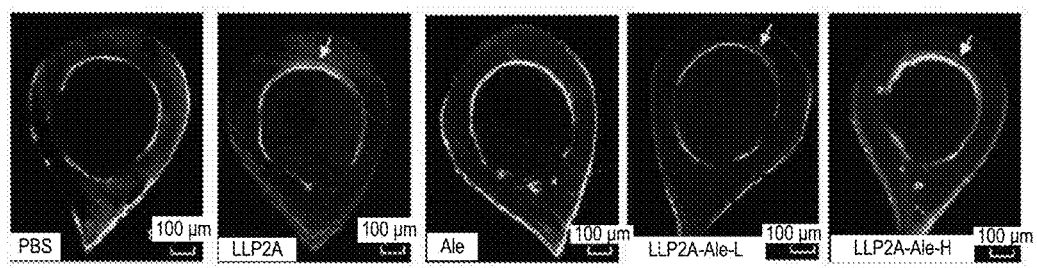
FIG. 16A-B show bone formation rates on the endocortical surfaces of the tibial shafts were increased in groups that had LLP2A component (P<0.05) in immunocompetent mice (129 SvJ).
Figure 16B:
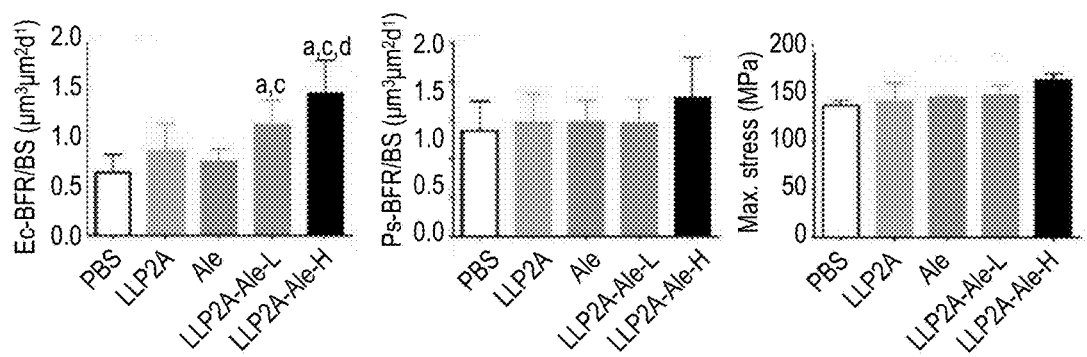
Figure 17:
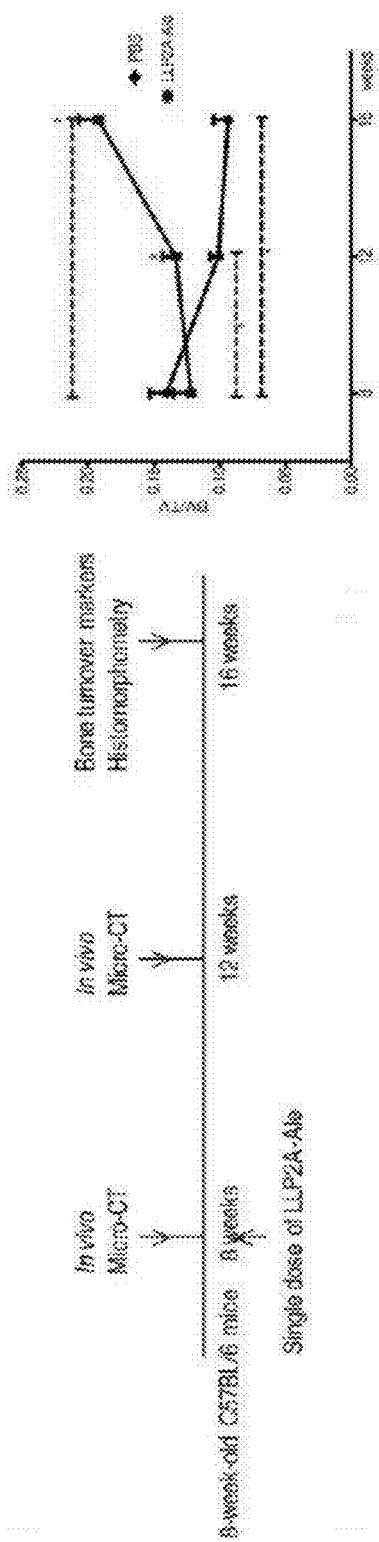
FIG. 17 shows LLP2A-Ale prevents age-related trabecular bone after peak bone acquisition in C57BL/6 mice.
Figure 18A:
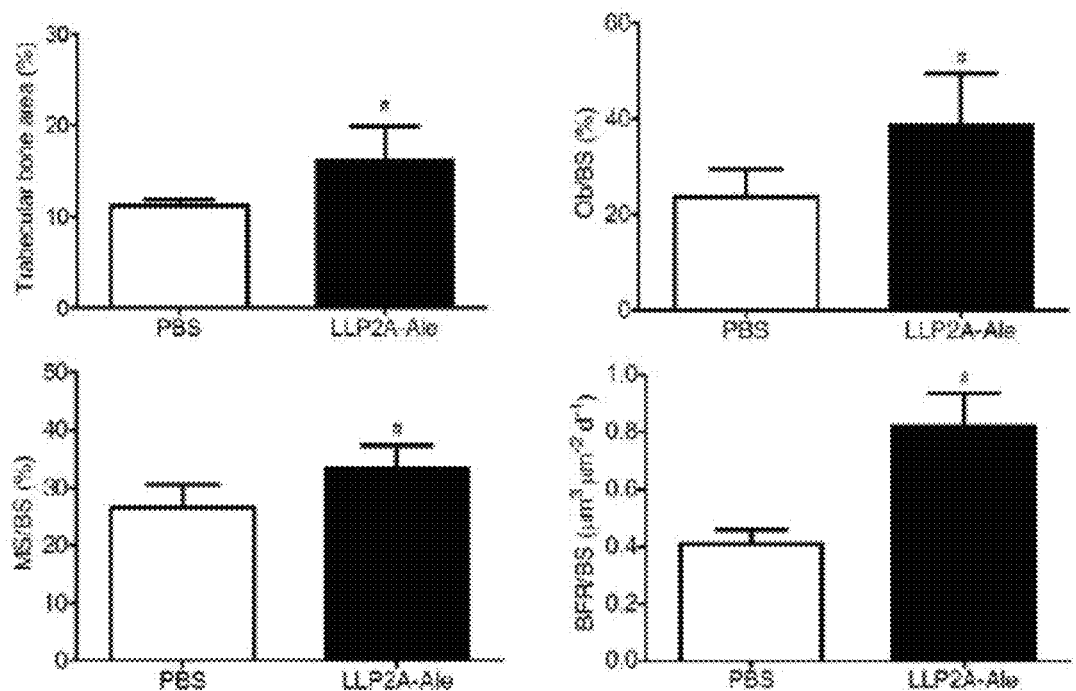
FIG. 18A-B show LLP2A-Ale increases bone formation parameters at the trabecular DF (P<0.05) in C57BL/6 mice.
Figure 18B:
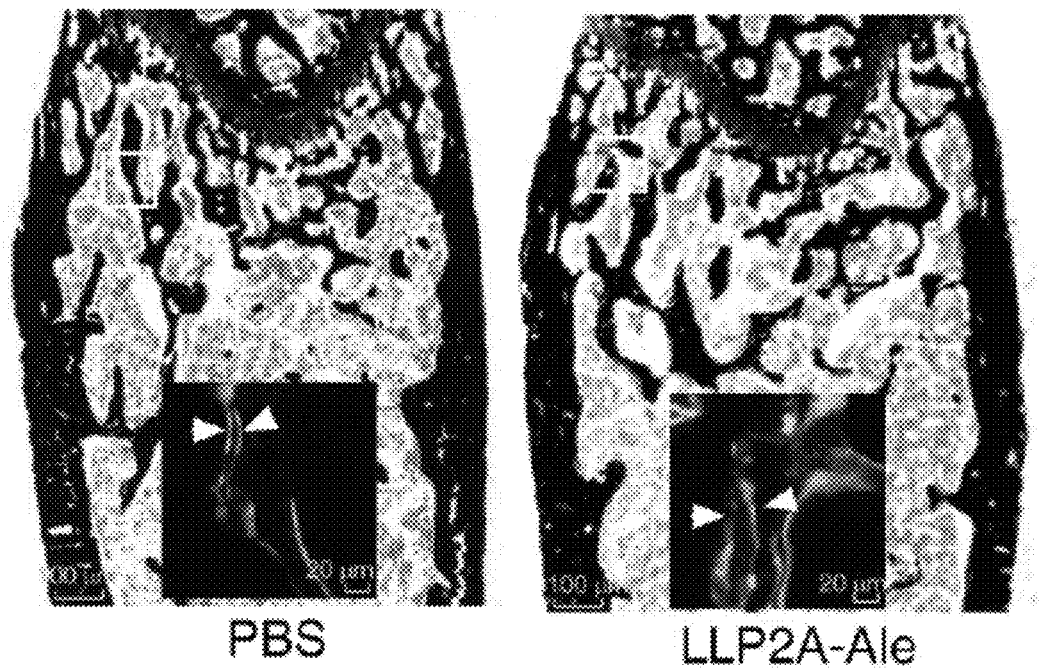
Figure 19A:
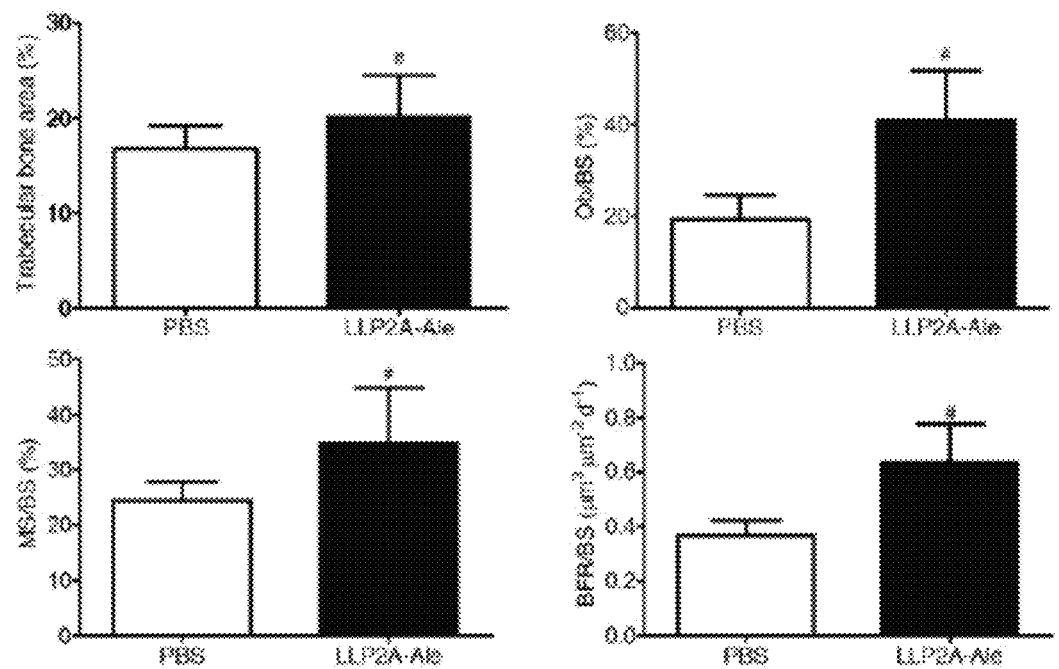
FIG. 19A-B show LLP2A-Ale increases bone formation parameters at the trabecular bone surfaces in the lumbar vertebral bodies (LVB) in C57BL/6 mice.
Figure 19B:
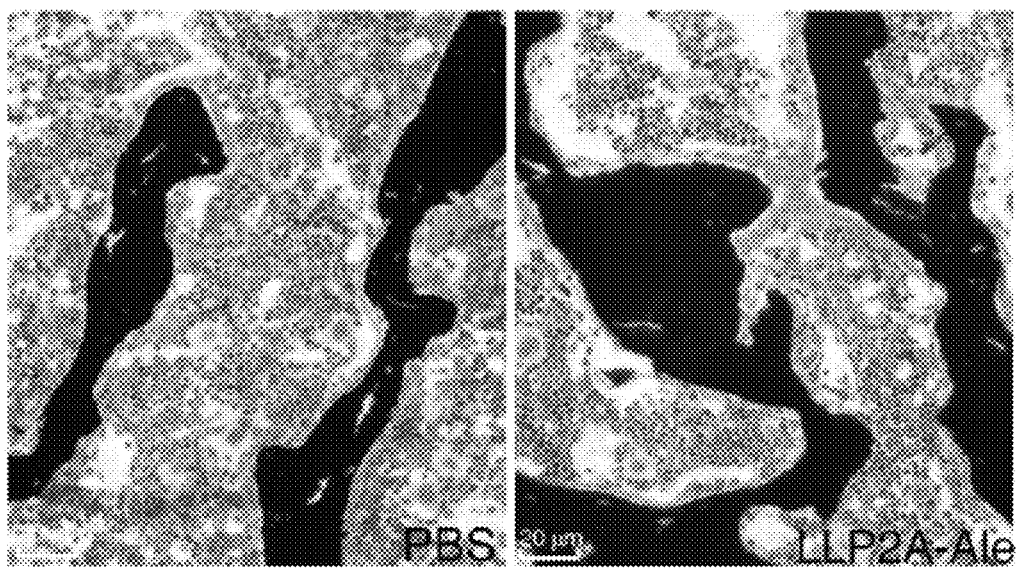

Exemplary compounds of the present invention are shown in FIG. 12.

IV. Pharmaceutical Compositions

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethyl-cellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

V. Administration

Administration of the ligands of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone.

The compositions containing a ligand or a combination of ligands of the present invention may be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a ligand or a combination of ligands. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, REMINGTON'S PHARMACEUTICAL SCIENCES, 18TH ED., Mack Publishing Co., Easton, Pa. (1990)). The composition to be administered contains a quantity of the ligand or combination of ligands in a pharmaceutically effective amount for relief of a condition being treated (e.g. osteoporosis) when administered in accordance with the teachings of this invention. In addition, pharmaceutically acceptable salts of the ligands of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4$^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the ligands or combination of ligands, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The ligands can also be formulated into a suppository disposed, for example, in a polyethylene glycol (PEG) carrier.

Liquid compositions can be prepared by dissolving or dispersing a ligand or a combination of ligands and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The ligands of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the ligand to the appropriate site or sites. However, one of ordinary skill in the art understands that the dose administered will vary depending on a number of factors, including, but not limited to, the particular ligand or set of ligands to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the ligands of the present invention permits a wider margin of safety for dosage concentrations and for repeated dosing.

Individuals to be treated using methods of the present invention can be any mammal. For example, local increase in bone can be used for fracture healing, fusion (arthrodesis), orthopedic reconstruction, and periodontal repair. Systemic increase in bone would be for treatment of low bone mass, i.e. osteoporosis. Such individuals include a dog, cat, horse, cow, or goat, particularly a commercially important animal or a domesticated animal, more particularly a human.

In other embodiments, the present invention provides a method of promoting systemic bone growth. Systemic bone growth refers to the growth of bone throughout the subject, and can effect all the bones in the subject's body. A subject in need of systemic bone growth can suffer from a variety of ailments and disease states. In some embodiments, the subject suffers from a low bone mass phenotype disease. Low bone mass can be determined by a variety of methods known to one of skill in the art. For example, low bone mass can be characterized by a T-score less than about −1. Low bone mass phenotype diseases can include osteoporosis, osteopenia, and osteoporosis-pseudoglioma syndrome (OPPG). In some other embodiments, the low bone mass phenotype disease can be osteopenia or osteoporosis-pseudoglioma syndrome (OPPG).

Following administration of the compounds of the present invention, systemic bone growth can be determined by a variety of methods, such as improvements in bone density. Bone density can be measured by a variety of different methods, including the T-score and Z-score. The T-score is the number of standard deviations above or below the mean for a healthy 30 year old adult of the same sex as the patient. Low bone mass is characterized by a T-score of −1 to −2.15. Osteoporosis is characterized by a T-score less than −2.15. The Z-score is the number of standard deviations above or below the mean for the patient's age and sex. Improvement in the T-score or Z-score indicate bone growth. Bone density can be measured in a variety of places of the skeleton, such the spine or the hip. One of skill in the art will appreciate that other methods of determining bone density are useful in the present invention.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Methods of Treating

In some embodiments, the present invention provides a method of treating osteoporosis, wherein the method includes administering to a subject in need thereof, a therapeutically effective amount of a compound of Formula I.

The present invention also provides methods of treating diseases characterized by secondary induced osteoporosis (low bone mass) including, but not limited to, osteomalacia, polyostotic fibrous dysplasia, Paget's disease, rheumatoid arthritis, zero gravity, osteoarthritis, prolonged inactivity or immobility, osteomyelitis, celiac disease, Crohn's disease, ulcerative colitis, inflammatory bowel disease, gastrectomy, secondary induced osteoporosis, amennorhea, Cushing's disease, Cushing's syndrome, diabetes mellitus, diabetes, eating disorders, hyperparathyroidism, hyperthyroidism, hyperprolactinemia, Kleinefelter syndrome, thyroid disease, Turner syndrome, steroid induced osteoporosis, seizure or depression induced osteoporosis, immobility, arthritis, cancer induced secondary osteoporosis, gonadotropin-releasing hormone agonists induced low bone mass, thyroid medication induced low bone mass, dilantin (phenytoin), depakote induced low bone mass, chemotherapy induced low bone mass, immunosuppressant induced low bone mass, blood thinning agents induced low bone mass, Grave's disease, juvenile rheumatoid arthritis, malabsorption syndromes, anorexia nervosa, kidney disease, anticonvulsant treatment (e.g., for epilepsy), corticosteroid treatment (e.g., for rheumatoid arthritis, asthma), Immunosuppressive treatment (e.g., for cancer), inadequate nutrition (especially calcium, vitamin D), excessive exercise leading to amenorrhea (absence of periods), smoking, and alcohol abuse, pregnancy-associated osteoporosis, copper deficiency, dibasic aminoaciduria type 2, Werner's syndrome, Hajdu-Cheney syndrome, hyperostosis corticalis deformans juvenilis, methylmalonic aciduria type 2, cystathionine beta-synthase deficiency, exemestane, hyperimmunoglobulin E (IgE) syndrome, Haemochromatosis, Singleton-Merten syndrome, beta thalassaemia (homozygous), reflex sympathetic osteodystrophy, sarcoidosis, Winchester syndrome, Hallermann-Streiff syndrome (HSS), cyproterone, glycerol kinase deficiency, Bonnet-Dechaume-Blanc syndrome, prednisolone, heparin, geroderma osteodysplastica, Torg osteolysis syndrome, orchidectomy, Fabry's disease, pseudoprogeria syndrome, Wolcott-Rallison syndrome, ankylosing spondylitis, myeloma, systemic infantile hyalinosis, Albright's hereditary osteodystrophy, autoimmune lymphoproliferative syndrome, Brown-Sequard syndrome, Diamond-Blackfan anemia, galactorrhoea-hyperprolactinaemia, gonadal dysgenesis, kidney conditions, Menkes disease, menopause, neuritis, ovarian insufficiency due to FSH resistance, familial ovarian insufficiency, premature aging, primary biliary cirrhosis, prolactinoma, familial prolactinoma, renal osteodystrophy, ulcerative colitis, underweight, Werner syndrome, bone tumor, bone cancer, brittle bone disease, osteogenesis imperfecta congenita, and osteogenesis imperfecta tarda. Other conditions include a bone injury, such as a fracture or weakened bone, or bone injured due to radiation treatment. One of skill in the art will appreciate that other types of conditions, diseases and treatments lead to osteoporosis.

The present invention also provides methods of treating patient populations characterized by injured bone, such as fractured bone or bone injured due to radiation, as well as children for whom osteoporosies medications are contraindicated.

In some embodiments, the present invention provides a method of promoting bone growth by administering to a subject in need thereof a therapeutically effective amount of a compound of the present invention.

Bone growth can be measured in a variety of ways known to one of skill in the art. Methods of measuring bone growth include, but are not limited to, Uct (micro CT), Dual X-ray absorption (Bone density), ultrasound, QCT, SPA, DPA, DXR, SEXA, QUS, X-ray, using the human eye during surgically manipulation, Alizarin red S, serum osteocalcin, serum alkaline phosphatase, Serum bone Gla-protein (BGP), bone mineral content, serum calcium, serum phosphorus, tantalum markers, and serum IGF-1.

Many indicators of bone growth can be used to measure bone growth, including bone density. In some embodiments, bone growth can be demonstrated by an increase of 0.1% in bone density. In other embodiments, bone growth can be demonstrated by an increase of 0.2, 0.3, 0.4, 0.5, 0.6, 0.7, 0.8, 0.9, 1.0, 5, 10, 20, 30, 40, 50, 60, 70, 80, 90, 100, 200, 300, 400, 500, 600, 700, 800, 900 or 1000% or greater, in bone density.

One of skill in the art appreciates that bone growth be local, systemic or both.

In some other embodiments, the method of the present invention promotes bone growth by administering the compound of the present invention, such as a compound of formula I. Administration of a compound of the present invention can promote local bone growth and/or systemic bone growth. In some embodiments, the administration of a compound of the present invention promotes systemic bone growth. Bone growth can be achieved by increasing bone mineral content, increasing bone density and/or growth of new bone. In other embodiments, local application of the compound of the present invention and a drug achieves systemic bone growth.

In some other embodiments, the present invention provides a method of treating low bone mass by administering to a subject in need thereof a therapeutically effective amount of a compound of the present invention.

VII. Examples

Example 1: Synthesis of LLP2A-Alendronate (LLP2A-Ale)

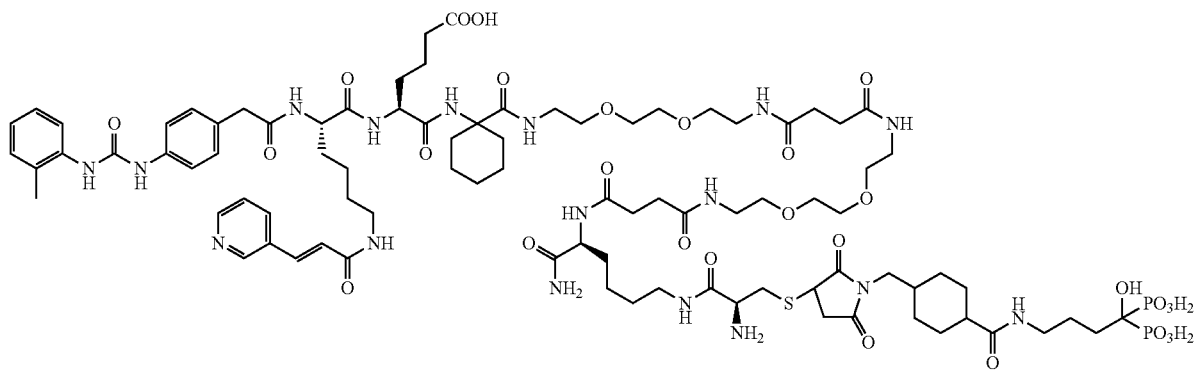

LLP2A-Ale

LLP2A-Alendronate (LLP2A-Ale) is made by conjugate addition of the sulfhydryl group of LLP2A-Lys(D-Cys) to Alendronate-maleimide (Ale-Mal), the latter being prepared in situ from alendronate and sulfosuccinimidyl-4-(N-maleimidomethyl)cyclohexane-1-carboxylate (sulfo-SMCC). LLP2A-Lys(D-Cys) is prepared by solid phase synthesis from several commercially available starting materials and one characterized intermediate, 4-[(N'-2-methylphenyl)ureido]phenylacetic acid (UPA), which was also prepared from commercially available starting materials.

Synthesis of 4-[(N'-2-methylphenyl)ureido]phenylacetic acid (UPA)

4-[(N'-2-methylphenyl)ureido]phenylacetic acid (UPA) was synthesized as outlined in FIG. 10A, Synthesis of UPA. In brief, UPA was synthesized by adding o-Tolyl isocyanate (19.646 mL, 158.47 mmol) dropwise to a suspension of 4-aminophenylacetic acid (23.8 g, 156.9 mmol) in N,N-dimethylformamide (DMF) (62 mL) with stirring. The mixture gradually became clear and was allowed to stir for 2 hours. The resulting solution was poured into ethyl acetate (700 mL) with stirring. The off-white precipitate was filtered and washed with ethyl acetate (3×100 mL) and acetonitrile (ACN) (3×100 mL), respectively. The solid was dried in vacuo. Weight (off-white powder): 36.7 g (82.3% crude yield). Orbitrap high resolution Electrospray Ionization Mass Spectrometry (ESI-MS) $[M+H]^+$: 285.1197 (calculated: 285.1239), $[M+Na]^+$: 307.1010 (calculated: 307.1059), $[M+K]^+$: 323.0746 (calculated: 323.0798).

Solid Phase Synthesis of LLP2A-Lys(D-Cys)

Figure 10B:
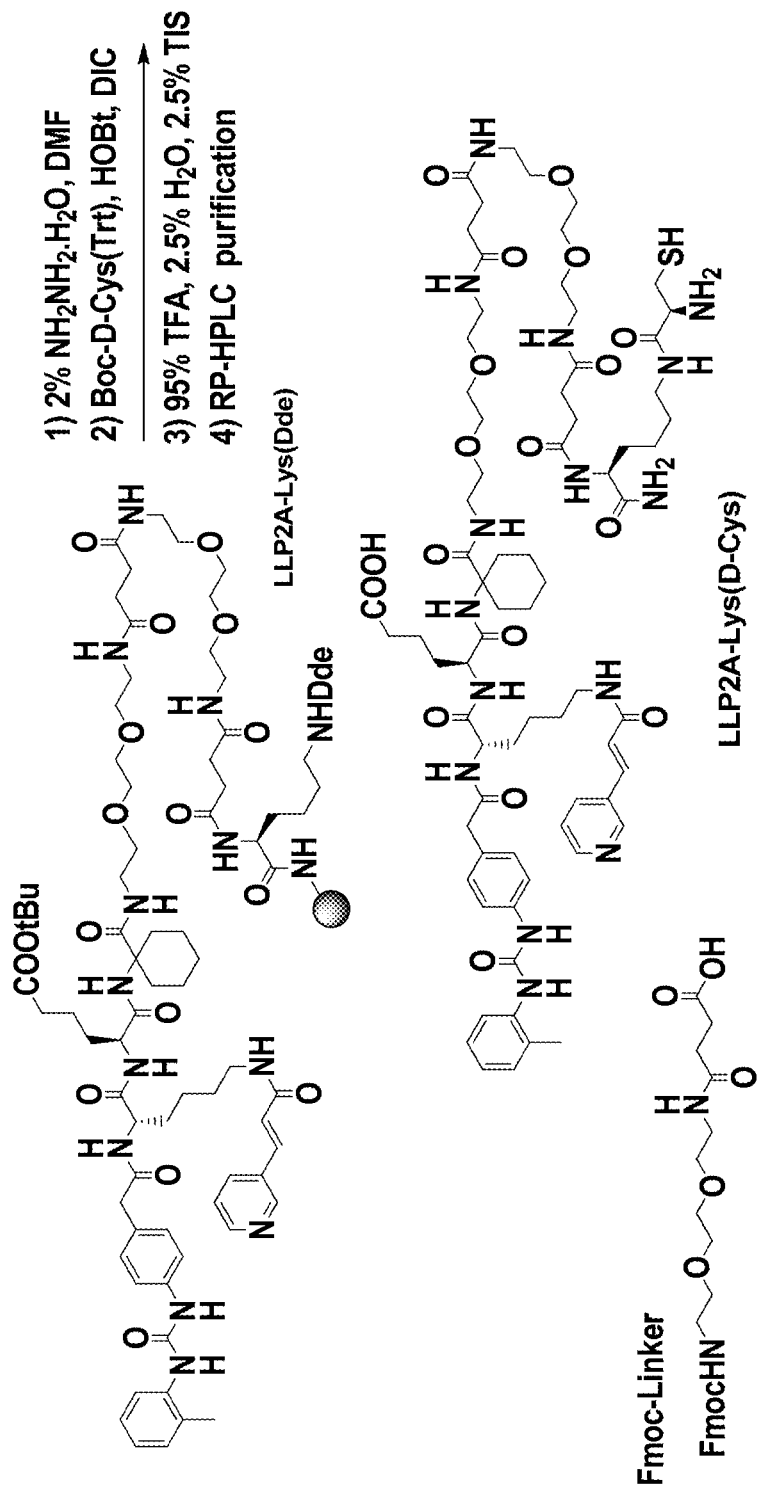

LLP2A-Lys(D-Cys) was synthesized as outlined in FIG. 10B, Solid phase synthesis of LLP2A-Lys(D-Cys).

Rink amide MBHA resin (0.5 g, 0.325 mmol, loading 0.65 mmol/g) was swollen in DMF for 3 hours before Fmoc-deprotection with 20% 4-methylpiperidine in DMF twice (5 and 15 minutes, respectively). The beads were then washed with DMF (3×10 mL), methanol (MeOH) (3×10 mL) and DMF (3×10 mL), respectively. Fmoc-Lys(Dde)-OH (0.519 g, 0.975 mmol) was dissolved in a solution of N-Hydroxybenzotriazole (HOBt) (0.149 g, 0.975 mmol) and N,N'-diisopropylcarbidiimide (DIC) (152 uL, 0.975 mmol) in DMF (8 mL), which was then added to the suspension of the beads. The coupling was carried out at room temperature overnight. After filtration, the beads were washed with DMF (3×10 mL), MeOH (3×10 mL), and DMF (3×10 mL), respectively.

After removal of Fmoc, the beads were then subjected to two cycles of coupling with and deprotection of the Fmoc-linker in the same manner as described above. The beads were washed with DMF (3×10 mL), MeOH (3×10 mL) and DMF (3×10 mL). Fmoc-Ach-OH (0.365 g, 0.975 mmol) was dissolved in a solution of HOBt (0.149 g, 0.975 mmol) and DIC (152 uL, 0.975 mmol) in DMF, and was then added into the beads. The coupling was carried out at room temperature for 2 hours. After filtration, the beads were washed with DMF (3×10 mL), MeOH (3×10 mL), and DMF (3×10 mL), respectively. The Fmoc deprotection group was removed with 20% 4-methylpiperidine twice ((5 and 15 minutes, respectively)).

After washing with DMF, MeOH, and DMF respectively, the beads were then subjected to additional coupling and deprotection cycles stepwise with Fmoc-Aad(OtBu)-OH and Fmoc-Lys(Alloc)-OH in the same manner as described above. After removal of Fmoc, a solution of UPA (0.923 g, 3.25 mmol), HOBt (0.498 g, 3.25 mmol) and DIC (509 µL, 3.25 mmol) in DMF was added to the beads. The reaction was conducted at room temperature until Kaiser test negative (3 hours to overnight). The beads were washed with DMF (3×10 mL), methanol (3×10 mL), and DMF (3×10 mL). The Alloc protecting group was removed by treating with $Pd(PPh_3)_4$ (0.2 eq.) and $PhSiH_3$ (20 eq.) in dichloromethane (DCM), twice (30 minutes, each).

A solution of trans-3-(3-pyridyl)acrylic acid (0.37 g, 1.3 mmol), HOBt (0.176 g, 1.3 mmol) and DIC (201 µL, 1.3 mmol) in DMF (8 mL) was added to the beads. The coupling proceeded at room temperature 4 hours to overnight until Kaiser test was negative. The beads were washed with DMF (5×5 mL), MeOH (3×5 mL) and DCM (3×5 mL). The Dde protecting group was removed with 2% $NH_2NH_2$ in DMF twice (5 and 10 minutes, respectively). The beads were washed with DMF, MeOH and DMF, followed by coupling of (4 eq. to resin, 220 mg, 1.3 mmol) Boc-D-Cys(Trt)-OH, HOBt (0.176 g, 1.3 mmol) and DIC (201 µL, 1.3 mmol) in DMF (8 mL). The coupling reaction was conducted at room temperature until Kaiser test negative (4 hours to overnight). The beads were thoroughly washed with DMF, MeOH and DCM, respectively, and then dried under vacuum for 1 hour before adding a cleavage mixture of 82.5% trifluoroacetic acid (TFA): 5% thioanisole: 5% phenol:5% water: 2.5% triisopropylsilane (TIS) (v/v). The cleavage reaction was conducted at room temperature over 2-3 hours. The off-white crude product was precipitated out and washed with cold ether. The purity was determined by analytical reverse phase high performance liquid chromatography (RP-HPLC) and the crude product was used in the next step without further purification. LLP2A-Lys(D-Cys) MALDI-TOF MS $[M+H]^+$: 1502.88 (calculated: 1502.77); $[M+Na]^+$: 1524.88 (calculated: 1524.75).

Synthesis of LLP2A-Ale

Figure 10C:
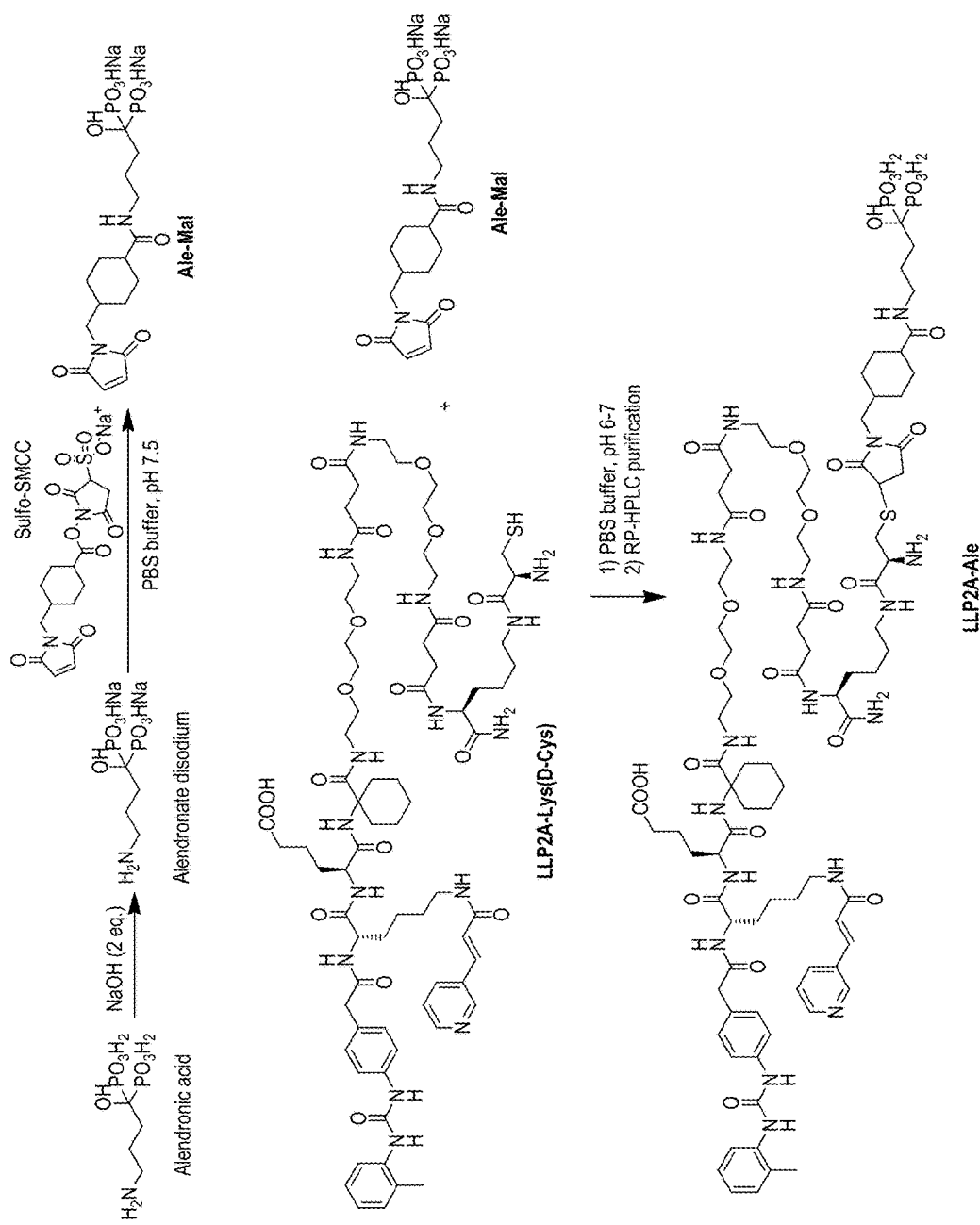

LLP2A-Ale was synthesized through conjugate addition of LLP2A-Lys(D-Cys) to Ale-Mal, formed in situ from alendronate and sulfo-SMCC. The synthetic scheme is shown in FIG. 10C, Preparation of LLP2A-Ale through conjugating LLP2A-Lys(D-Cys) with Ale-Mal.

Alendronate disodium salt (1.0 eq.) (powder from lyophilization of aqueous solution of alendronic acid and 2 eq. NaOH) was dissolved in 0.1 M phosphate buffered saline (PBS) (with 10 mM ethylenediamine tetraacetic acid), pH7.5. The aqueous solution was then cooled in an ice water bath, and a solution of Sulfo-SMCC (1.1 eq.) in water was added dropwise. Following completion of addition, the resulting solution was allowed to warm to room temperature while being stirred for 2 hours. This solution was cooled before the dropwise addition of a solution of LLP2A-Lys (D-Cys) (1.0 eq.) in a small amount of 50% acetonitrile/water. The pH was adjusted to between 6 and 7 with aq. $NaHCO_3$, if needed. The resulting mixture was allowed to warm to room temperature and stirred for 1 hour or until Ellman test negative, and then lyophilized. The resulting powder was redissolved in a small amount of 50% ACN/water and purified by RP-HPLC (C18 column). Buffer A: 0.5% acetic acid/$H_2O$. Buffer B: 0.5% acetic acid/ACN. The collected eluent was lyophilized to give a white powder. The identity of LLP2A-Ale was confirmed with Matrix-assisted laser desorption/ionization time of flight mass spectrometry (MALDI-TOF MS)$[M+H]^+$: 1970.78 (calculated: 1970.88).

Example 2: Synthesis of LLP2A-Alendronate (1)
[LLP2A-Ale (1)]

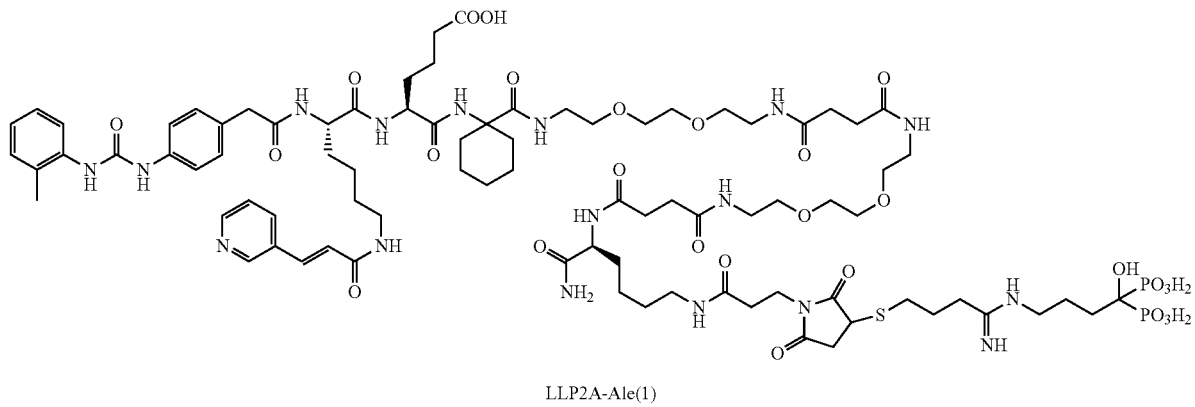

LLP2A-Ale(1)

Figure 11:
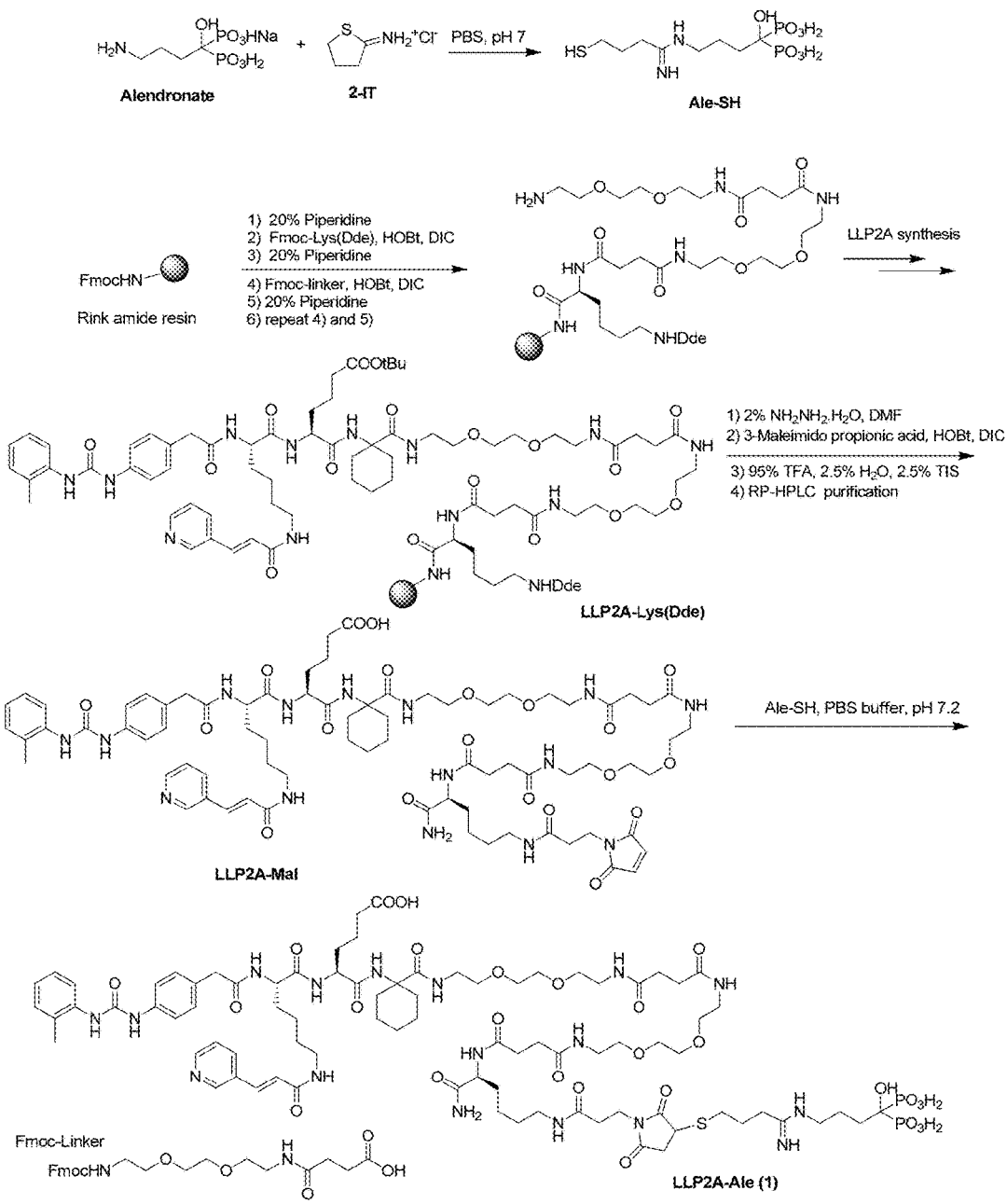
FIG. 11 shows the synthesis of LLP2A-Ale (1).

LLP2A-Ale (1) was synthesized through conjugation of Alendronate-SH (Ale-SH) to LLP2A-Mal via Michael addition. The synthetic scheme is shown in FIG. 11.

Preparation 1a: Synthesis of Ale-SH.

The synthesis of Ale-SH was achieved by reacting alendronate with 2-IT (1 equivalent) in PBS at pH 7.5 for 1 hour followed by precipitation with EtOH. The solid was dissolved in water and precipitated with EtOH, twice.

Preparation 1b: Synthesis of LLP2A-Mal.

LLP2A-Mal was prepared with maleimide attached to the side chain of Lys and two hydrophilic linkers between LLP2A and Lys(Mal) using similar approach described above. The synthesis was performed on rink amide MBHA resin by standard solid-phase peptide synthesis approach using Fmoc/tBu chemistry and HOBt/DIC coupling. The synthetic scheme is shown in FIG. 11. Fmoc-Lys(Dde)-OH was first coupled to the resin, followed by coupling of two linkers. LLP2A was then prepared as previously reported on the N-terminus of the linker using similar approach described above. The Dde protecting group was removed with 2% $NH_2NH_2$ in DMF twice (5 min, 10 min). The beads were washed with DMF, MeOH and DMF, followed by coupling of (3 equivalents to resin) 3-maleimido propionic acid and HOBt, DIC. The coupling reaction was conducted at room temperature overnight. The beads were thoroughly washed with DMF, MeOH and DCM and then dried under vacuum for 1 hour before adding a cleavage mixture of 95% TFA: 2.5% water: 2.5% TIS. Cleavage of compounds from the resin and removal of protecting group were achieved simultaneously over 2 hours at room temperature. The off-white crude products were precipitated with cold ether and purified by semi-preparative reversed-phase high performance liquid chromatography (RP-HPLC) to give LLP2A-Mal. The identity of LLP2A-Mal was confirmed by MALDI-TOF MS [M+Na]+: 1572.76 (calculated: 1549.78).

Preparation 1c: Synthesis of LLP2A-Ale (1).

LLP2A-Ale (1) was prepared by conjugating LLP2A-Mal with Ale-SH. Ale-SH was dissolved in PBS buffer at pH 7.2 containing 5% DMSO. Subsequently, a solution of LLP2A-Mal (1.2 equivalents) in a small amount of DMSO was added to the Ale-SH solution. The resulting mixture was stirred at room temperature for 1 hour and then lyophilized. The powder was re-dissolved in a small amount of water and passed through Varian MEGA BOND ELUT C18 column (60 mL, 40 um particle size) and eluted with water, 5% ACN/water, 10% ACN/water and 50% ACN/water. The eluents were collected and checked by mass spectroscopy. The eluents with pure product were combined and lyophilized to give white powder. MALDI-TOF MS [M+H]+: 1900.78 (calculated: 1899.83).

Example 3: Osteogenic Differentiation of Bone Marrow Stem Cells with a High Affinity to LLP2A A new color-encoding method that facilitates high-throughput screening of OBOC combinatorial libraries was developed. This method differs from the traditional methods used to monitor integrin expressions in the MSCs, i.e., the use of antibody-based fluorescence-activated cell sorting (FACS) or immunoblotting. In the present method, polymer beads displaying chemical compounds or families of compounds were stained with oil-based organic dyes that are used as coding tags. The color dyes did not affect cell binding to the compounds displayed on the surface of the beads. These rainbow beads were prepared in a multiplex manner such that each ligand reacted to one or a series of integrins that were coded one color. See FIG. 7; see also, Luo, J., et al., *J Comb Chem,* 2008, 10(4): p. 599-604. This rainbow bead technique was then applied to determine the integrin profile on the cell surfaces. By incubating the bone marrow cells undergoing osteogenic differentiation with the rainbow beads, we found that $\alpha_4\beta_1$ integrin was highly expressed in these osteoprogenitor cells and had high affinity to LLP2A as shown in FIG. 7.

Figure 7:
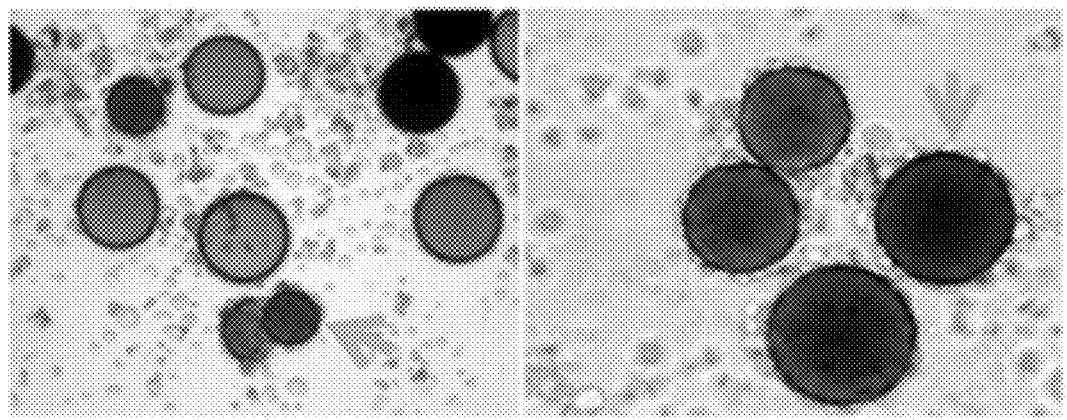
FIG. 7 shows osteogenic cells had high affinity for LLP2A-Ale. Mouse MSCs were purchased from Invitrogen (Cat#S1502-100), cultured in osteogenic medium for 7 days and incubated with rainbow beads for one hour. The purple beads that displayed LLP2A, the ligand with high affinity and specificity against α4β1, were covered with layers of cells (green arrows). Original magnification 10× on the right and 20× on the left of the top panel.
Figure 20:
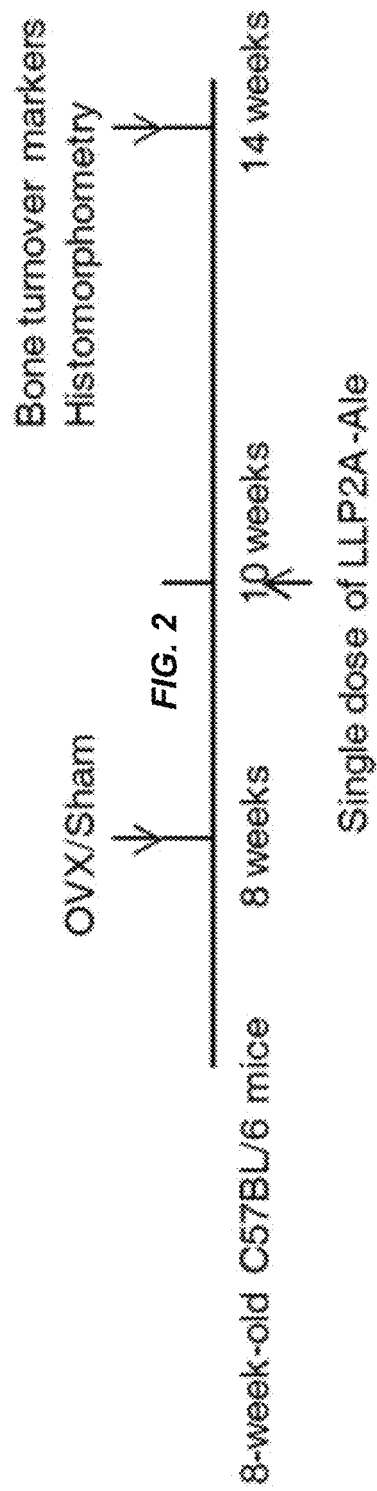
FIG. 20 shows a scheme of 10-week-old ovariectomized (OVX) mice treated with PBS, Ale, LLP2, LLP2A-Ale or PTH 2-weeks after ovariectomy.
Figure 21:
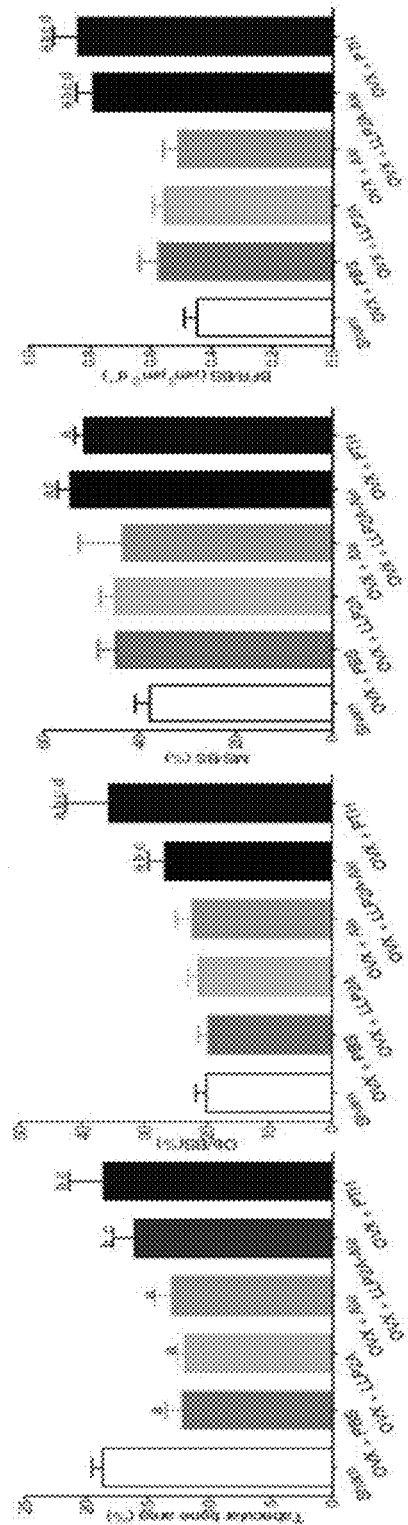
FIG. 21 depicts histomorphometric analyses of the 5th lumbar vertebral bodies after LLP2A-Ale treatment of 10-week-old ovariectomized (OVX) mice, showing increases in osteoblast numbers, activities and bone formation rate/bone surface (BFR/BS) post-treatment. Analyses included trabecular bone area (%), osteoblast surface (Ob/BS), mineralizing surface (MS/BS) activities and BFR/BS (P<0.05).
Figure 22:
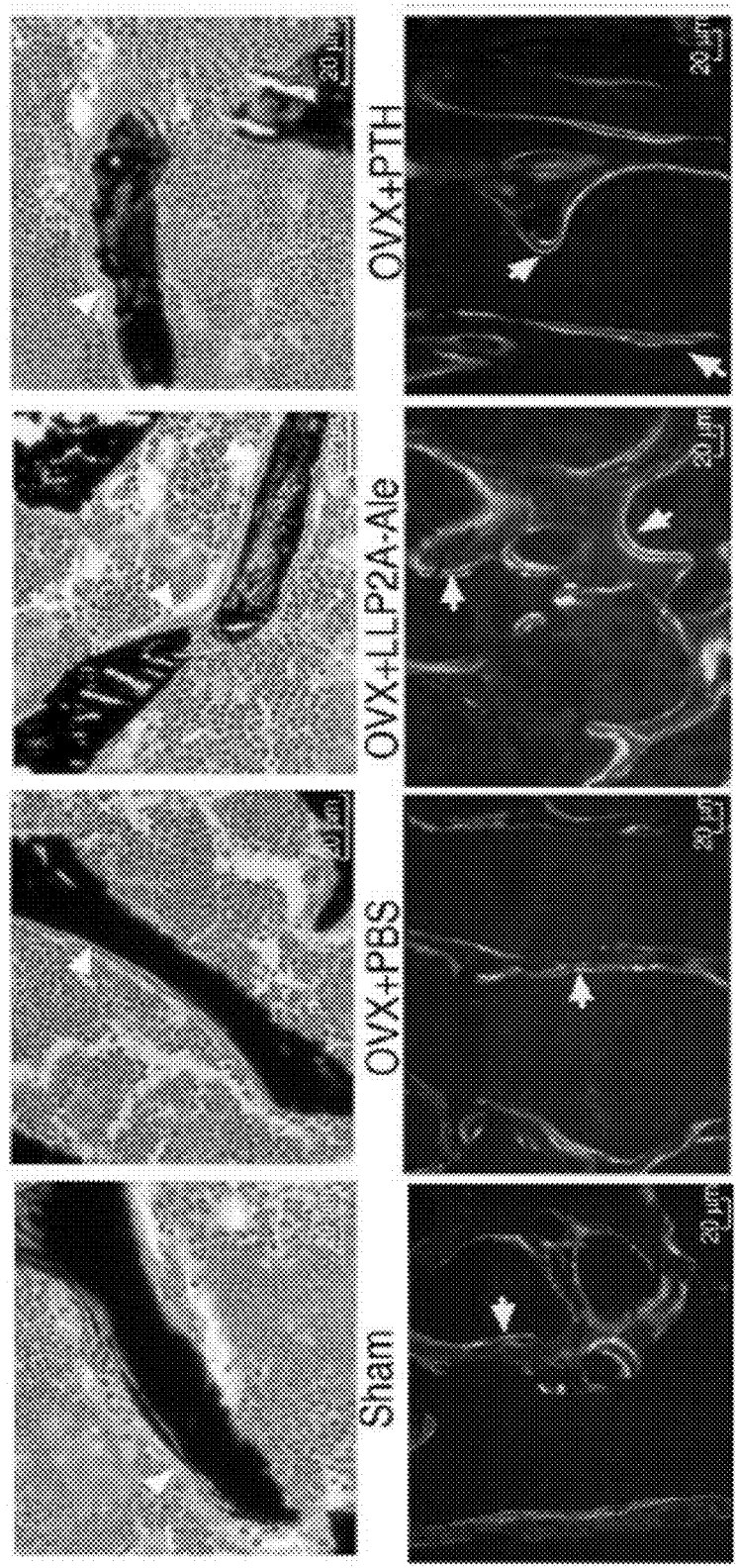
FIG. 22 shows LLP2A-Ale treatment increases osteoblast numbers in the lumbar vertebral bodies (LVB) of 10-week-old ovariectomized (OVX) mice. Representative fluorescent images from the trabecular bone at the 5th LVB (Top panel: white arrowheads illustrate osteoblasts; Bottom panel: yellow arrows illustrate double labeled trabecular bone surfaces).
Figure 23:
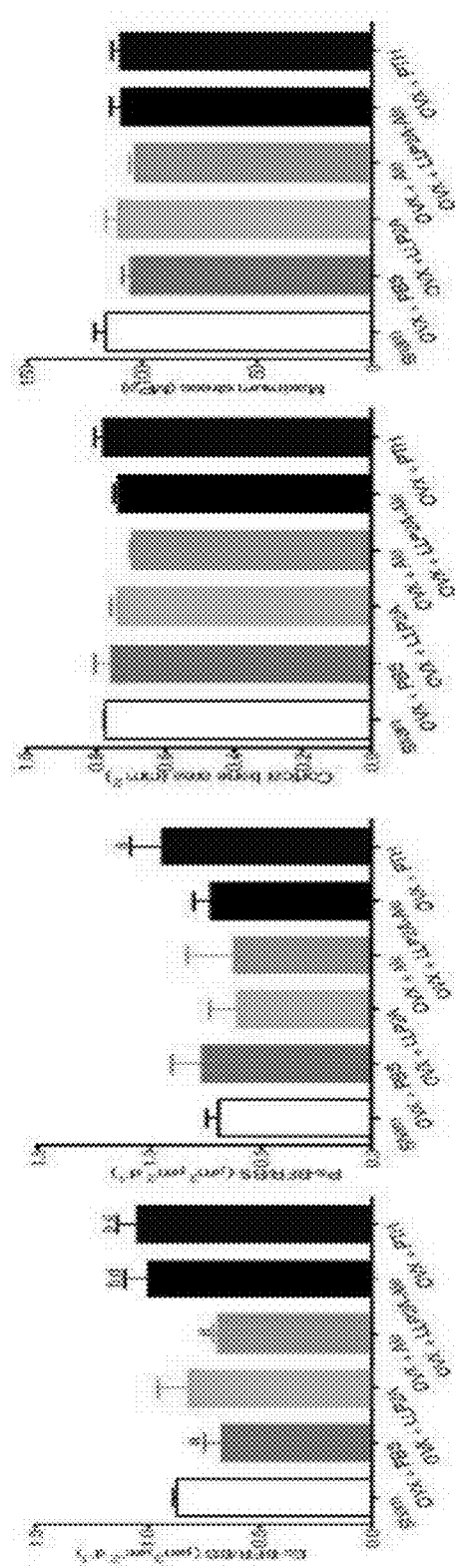
FIG. 23 depicts histomorphometry analyses of the right mid-femurs included bone formation at the endosteal (Ec) or periosteal (Ps.) bone surfaces, and cortical bone thickness of 10-week-old ovariectomized (OVX) mice. Increases in endocortical bone formation from OVX were observed in the LLP2A-Ale and PTH treated mice, however cortical bone thickness and maximum stress were not significantly altered by OVX, Ale, and LLP2A, one single IV injection of LLPAle or four weeks of PTH treatment. Three-point bending was performed on left femurs to obtain maximum stress of the femurs.
Figure 24:
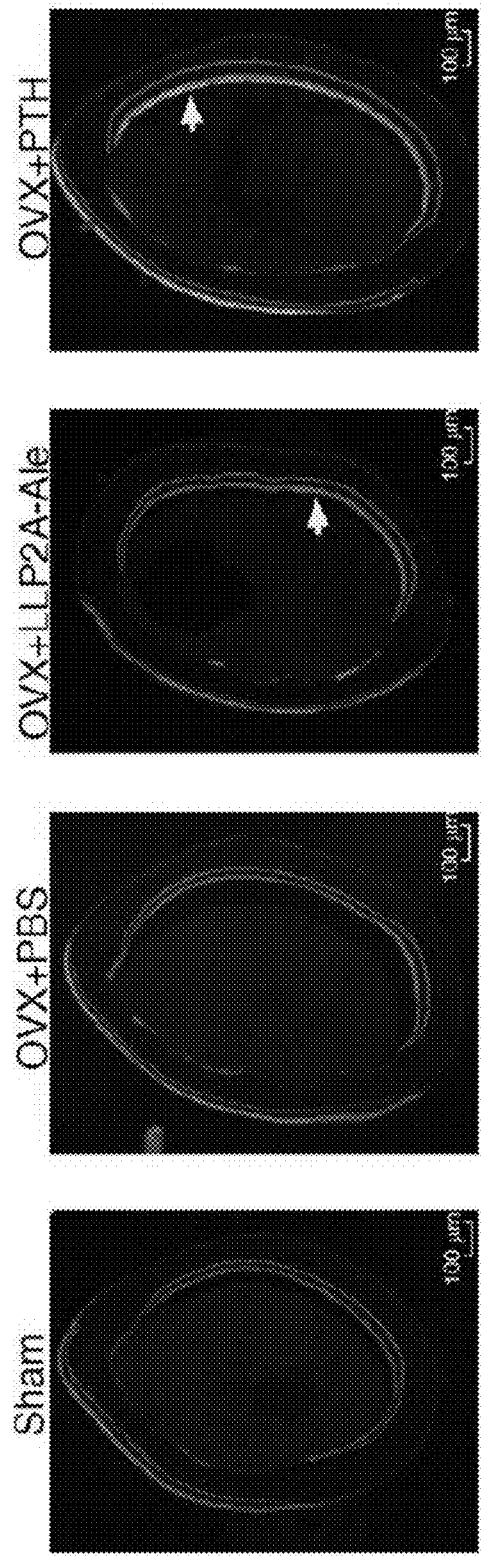
FIG. 24 shows representative fluorescent images from the mid-femur sections of 10-week-old ovariectomized (OVX) mice and increases in endocortical bone formation were observed in the LLP2A-Ale and PTH treatments. Short yellow arrows illustrated double labeled endocortical bone surfaces. (a, p<0.05 versus Sham; b, P<0.05 vs. OVX+PBS, c, P<0.05 vs. OVX+LLP2A; d, P<0.05 vs. OVX+Ale. Data are represented as Mean±SD).
Figure 25:
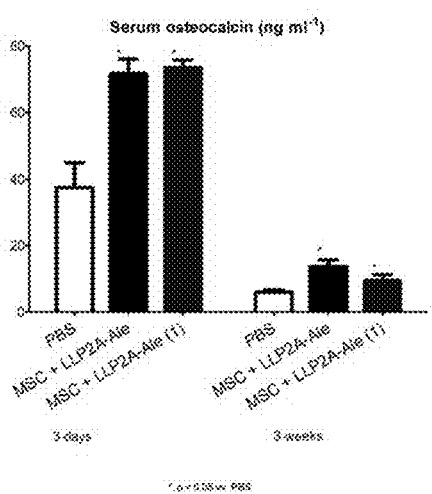
FIG. 25 shows the evaluation of the efficacy of LLP2A-Ale and LLP2A-Ale (1) in their ability in guiding the mesenchymal stem cells (MSC) to bone. We injected 2×10$^5$ mouse green florescence labeled (GFP)-MSCs to 2-month-old (3-day experiment) or to the 5-month-old (3-week experiment) C57BL/6 mice via I.V. tail vein. LLP2A-Ale or LLP2A-Ale (1) were dissolved in 0.9% normal saline and injected I.P. to the mice one hour after MSC at a final solution of 0.9 nmol/mouse. Mice were sacrificed either at 3 days or 3 weeks. Osteocalcin, a bone formation marker, was measured at both 3 days and 3 weeks post-treatments. The lumbar vertebral bodies from the 3-day treatment groups were frozen and sectioned with cryostat. The sections were then stained with anti-GFP antibody. The transplanted MSCs were stained in brown. We found both LLP2A-Ale and LLP2A-Ale (1) significantly increased osteocalcin levels at both three-days and three weeks following the treatments. Transplanted MSCs were observed within bone marrow and adjacent to the trabecular bone surfaces at three-days.
Figure 25:
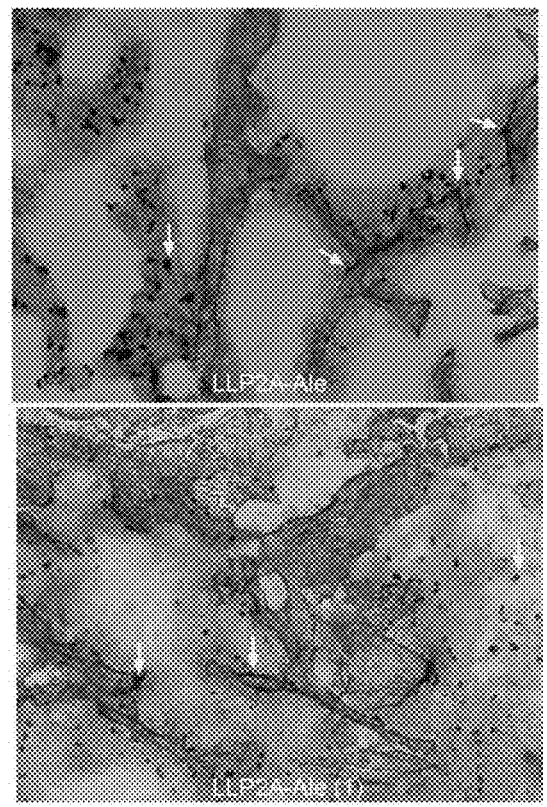

In FIG. 7, bone marrow cells were cultured in osteogenic medium for 7 days and incubated with rainbow beads. The purple beads that coded with LLP2A, the ligand with high affinity and specificity against $\alpha_4\beta_1$, were covered with layers of cells identified by green arrows. Original magnification, 10x, is shown on the right side of FIG. 7, and 20x magnification is shown on the left side. Weak bindings were also seen in the black, purple and green beads, coded RGD1, RGD2 and LYK1 ligands respectively. All of these beads had nonspecific bindings to many other integrins.

Example 4: Human-MSCs Directed to Bone with LLP2A-Ale for Promoting Bone Growth

Human MSCs (huMSCs) were obtained and injected together with LLP2A-Ale to immunodeficienct mice, NOD/

Figure 2A:
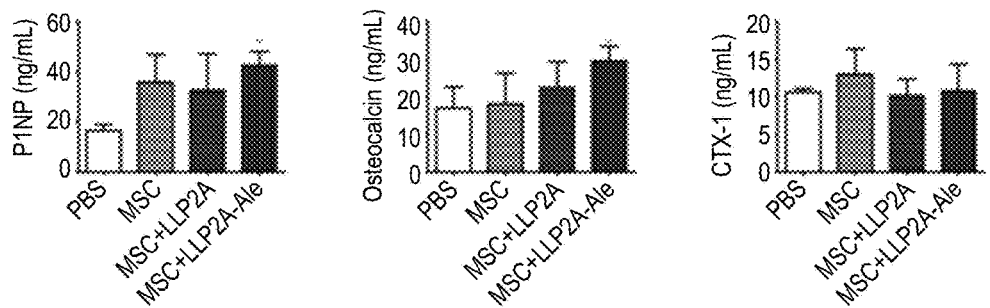
FIG. 2A-C show LLP2A-Ale increases trabecular bone formation three weeks following huMSCs transplantation in NOD/SCID/MSPVII mice.
Figure 2B:
Figure 2C:
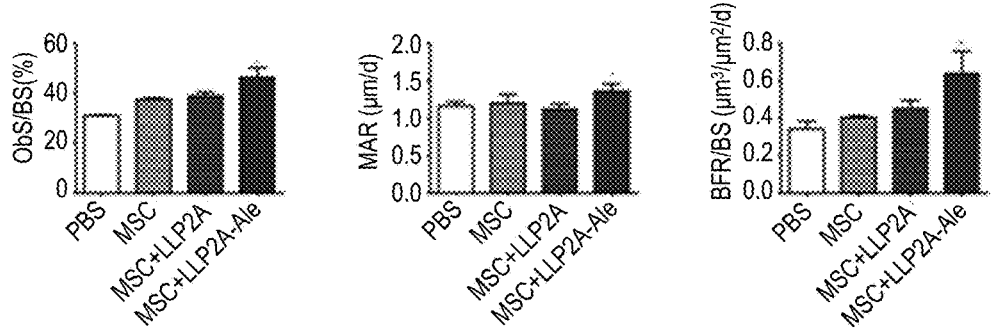
Figure 3A:
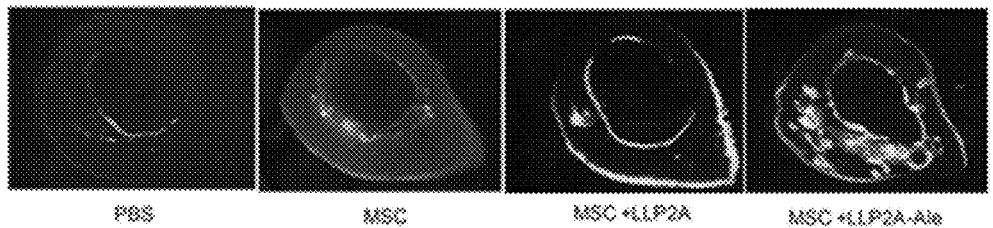
FIG. 3A-B show LLP2A-Ale increases cortical bone formation three weeks following huMSCs transplantation in NOD/SCID/MSPVII mice.
Figure 3B:
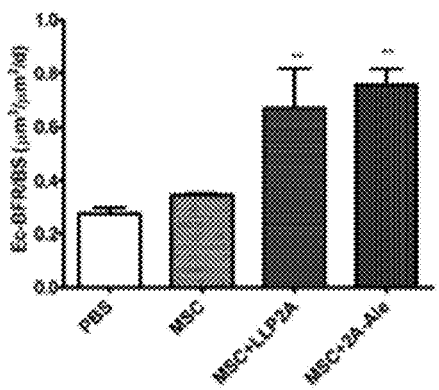
Figure 3B:
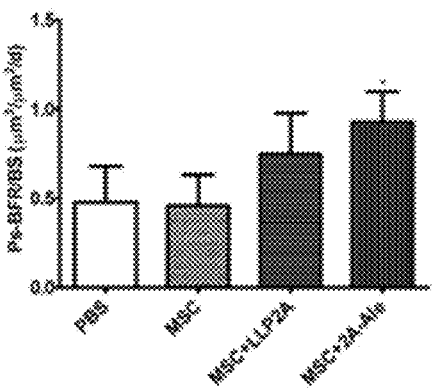
Figure 4A:
FIG. 4A-C show LLP2A-Ale increases cancellous bone mass through increasing the thickness of the trabeculae. In vivo microCT scans were performed on the right distal femurs at baseline (basal) and repeated after 4 weeks.
Figure 4B:
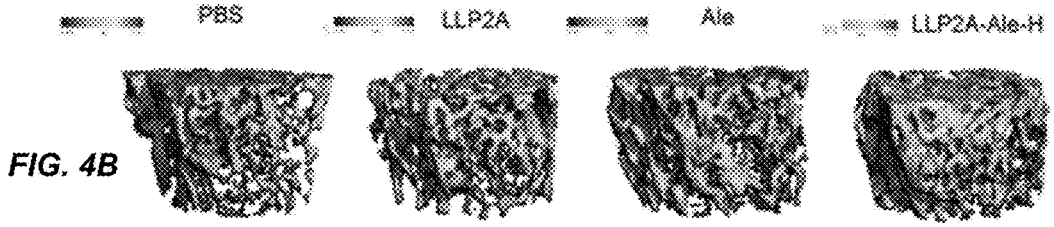
Figure 4C:
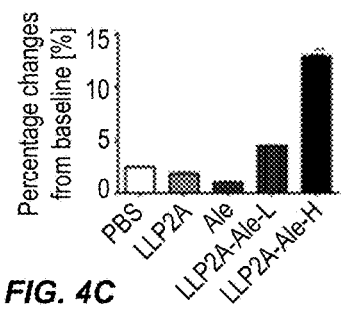
Figure 4C:
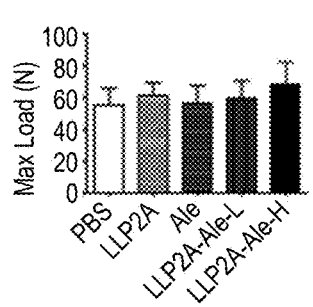
Figure 4C:
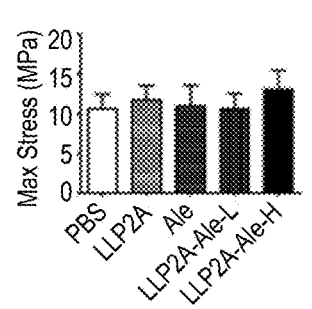
Figure 8:
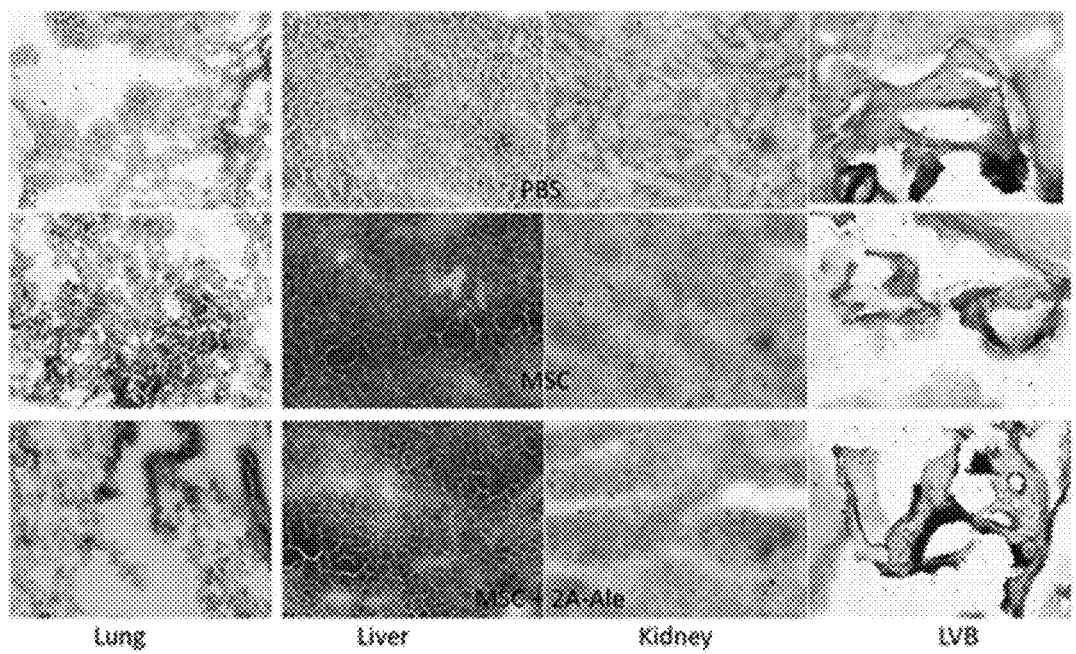
FIG. 8 shows Beta-glucuronidase distribution in various tissues 24-hours following huMSCs transplantation in NOD/SCID/MSPVII mice.

SCID/mucopolysaccharidosis type VII (MPSVII). This mouse strain lacked the β-glucuronidase (GUSB) enzyme. The donor cells could be easily detected using biochemical detection of β-glucuronidase (See Meyerrose, T. E., et al., *Stem Cells*, 2007. 25(1): p. 220-7; Meyerrose, T. E., et al., *Stem Cells*, 2008. 26(7): p. 1713-22). At three-month of age, the mice received a single intravenous (i.v.) injection of either vehicle (100 μl PBS/mouse), huMSCs ($5\times10^5$/100 μl/PBS/mouse), huMSCs+LLP2A (5 nM/mouse) or huM-SCs+LLP2A-Ale (500 ng/mouse; total compound weight 3.5 μg, with alendronate concentration of 500 ng/mouse). The alendronate dose we used for the study was approximately one-fifth of the therapeutic dose for the treatment of osteoporosis (See Colon-Emeric, C. S., *JAMA*, 2006, 296 (24): p. 2968-9; Ma, Y. L., et al., *Endocrinology*, 2003. 144(5): p. 2008-15). As shown in FIG. 8, LLP2A-Ale greatly increased the number of huMSCs on the bone surface of huMSCs to bone as compared to the control groups (PBS and huMSCs) 24 hours after the huMSCs injection. As shown in FIG. 1, three weeks after the transplantation, the huMSCs were only seen adjacent to the bone surface in LLP2A-Ale treated group. HuMSC, as shown by GUSB+red stain, were only present at the trabecular bone surface in the LLP2A-Ale-treated group (lower panel). There was no demonstrable GUSB activity in the lung, liver, kidney and LVB that received PBS (top panels) or huMSCs (middle panel). Cancellous bone mass in the vertebral body was—more than 40% higher in the group treated with MSC+LLP2A-Ale (cancellous bone volume, BV/TV 13.9±2.2%) compared to PBS (BV/TV 9.4±1.7%), MSC (BV/TV 10.2±1.9%) or MSC+LLP2A (BV/TV 10.5±0.5%) controls three weeks after a single injection of huMSC and LLP2A-Ale. This increase in cancellous bone mass was accompanied by significant increases in biochemical bone formation parameters such as bone formation markers, procollagen I N-terminal propeptide (P1NP), and osteocalcin, see FIG. 2A, and surfaced-based bone formation parameters such as osteoblast surface, mineral apposition rate or surface-based bone formation rate (BFR/BS). See FIG. 2B-2C. Osteoclastic resorption did not differ between the groups (CTX-1). See FIG. 2A. As shown in FIG. 3A-B, bone formation rates at both the endocortical and periosteal surfaces of the mid-femur also increased by 50-100%, with markedly increased in intra-cortical bone remodeling in huMSC+LLP2A-Ale treated group. These preliminary data demonstrate that LLP2A-Ale can direct MSCs to bone to enhance both cancellous and cortical bone formation and bone mass.

In FIG. 8, Three-month-old MSPVII mice received a single intravenous injection of either of PBS, huMSC ($5\times10^5$) or huMSC+LLP2A or LLP2A-Ale. The mice were sacrificed 24 hours later. Following sacrifice, small portions of organ including lumbar vertebral bodies (LVB) were harvested and frozen in Optimal Cutting Temperature embedding media. The sections were stained using naphthol-AS-BI-β-Dglucuronide (GUSB) as a substrate. Representative sections from lung, liver, kidney and lumbar vertebral (LVB) trabecular bone regions were presented. Human MSCs, as showed by GUSB+red stains, were seen accumulated in lung, liver and kidney at 24-hours in huMSC, huMSC+LLP2A or huMSC+LLP2A-Ale groups. Significant amount of these cells were also seen adjacent to bone surface only in huMSCs+LLP2A-Ale group (lower panels). Isolated GUSB-positive cells were also observed within bone marrow of the LVB in MSC (middle panel) group.

NOD-SCID MPSVII Mice.

The NOD-SCID MPSVII strain was the result of extensive backcrossing of the mutant GUSB allele from the B6. C-H-$2^{bm1}$/ByBirgus$^{mps/+}$ mouse onto the NOD/LtSz-scid background. Animals were bred and maintained at the Stem Cell Department of the UC Davis Medical Center under approved animal care protocols. Affected animals were generated by breeding mice heterozygous for the MPSVII mutation. Homozygous GUSB-deficient pups were identified at birth by biochemical analysis of toe tissue.

Biochemical Markers of Bone Turnover.

Serum levels of the amino terminal propeptide of type 1 procollagen (P1NP), osteocalcin and C-terminal telopeptides of type I collagen (CTX-I) were measured using mouse sandwich ELISA kits from Biomedical Technologies (Stroughton, Mass.) or Immunodiagnostic System (Fountain Hills, Ariz.). The manufacturer's protocols were followed and all samples were assayed in duplicate. A standard curve was generated from each kit and the absolute concentrations were extrapolated from the standard curve. The coefficients of variations (CVs) for inter-assay and intra-assay measurements were less than 10% for all assays and are similar to the manufacturer's references (Yao, W., et al., *Arthritis Rheum*, 2008, 58(6): p. 1674-86; Yao, W., et al., *Arthritis Rheum*, 2008, 58(11): p. 3485-3497).

Example 5: LLP2A-Ale Augmented Bone Formation and Bone Mass

Figure 5A:
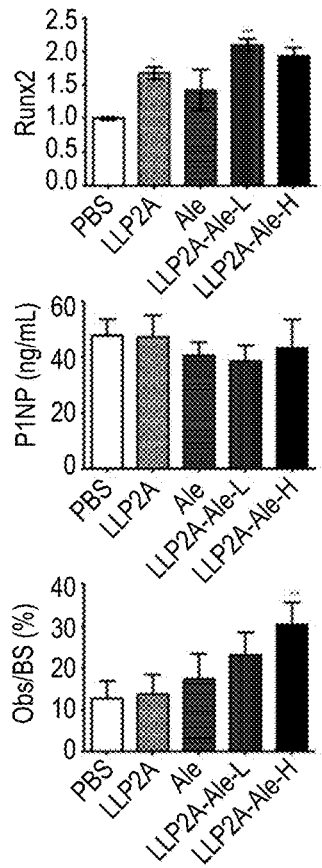
FIG. 5A-C show LLP2A-Ale increases cancellous bone formation in young "normal" mice.
Figure 5A:
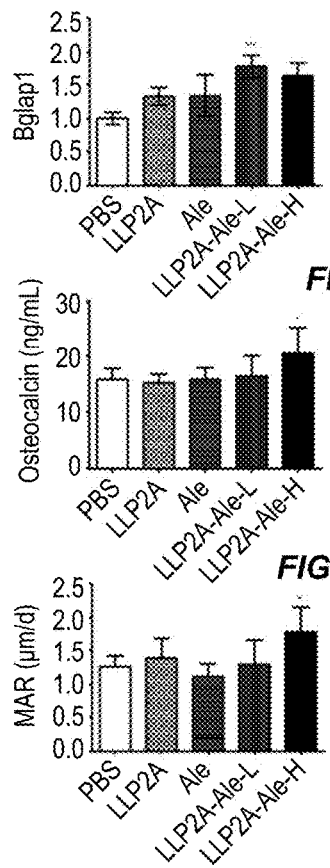
Figure 5B:
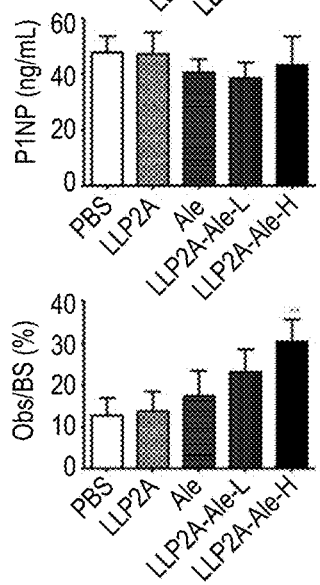
Figure 5B:
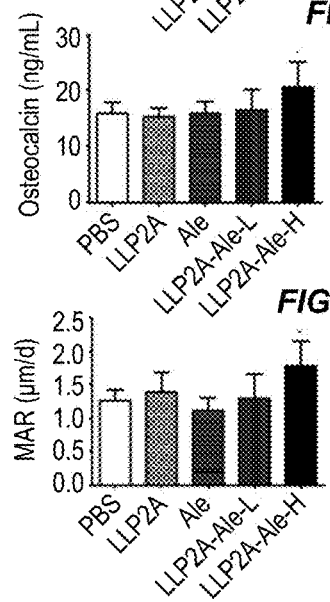
Figure 5B:
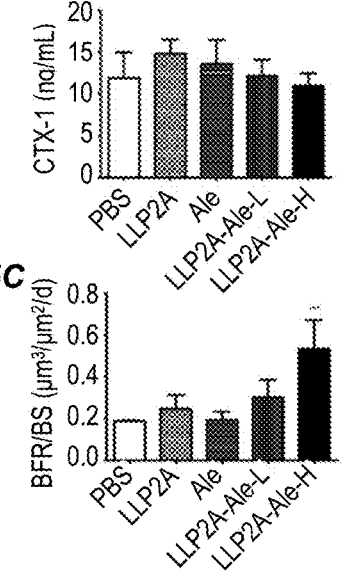
Figure 5C:
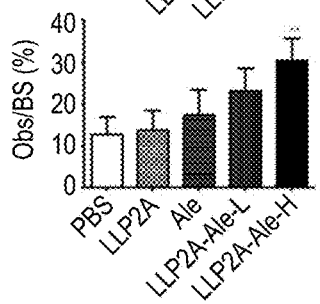
Figure 5C:
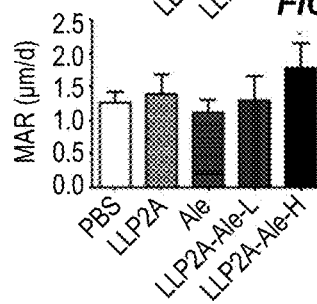
Figure 6A:
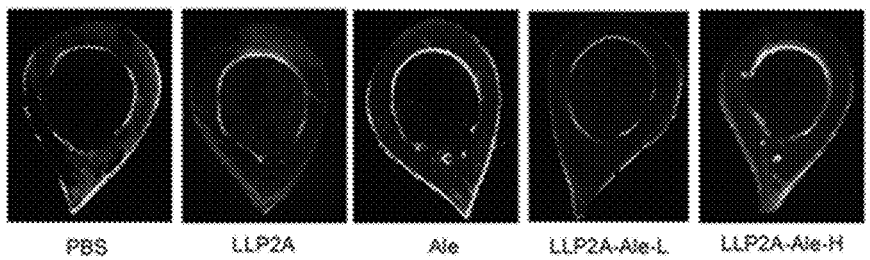
FIG. 6A-B show LLP2A-Ale increases cortical bone formation in young normal mice.
Figure 6B:
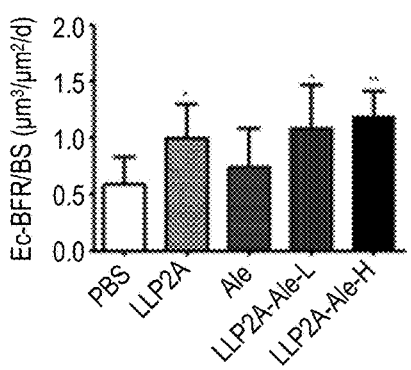
Figure 6B:
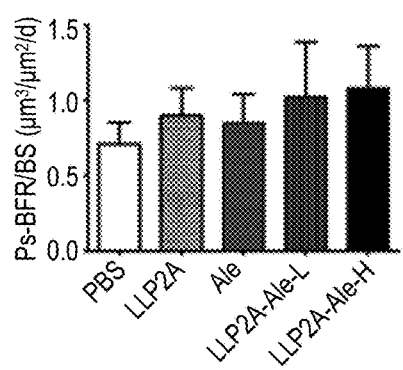
Figure 9:
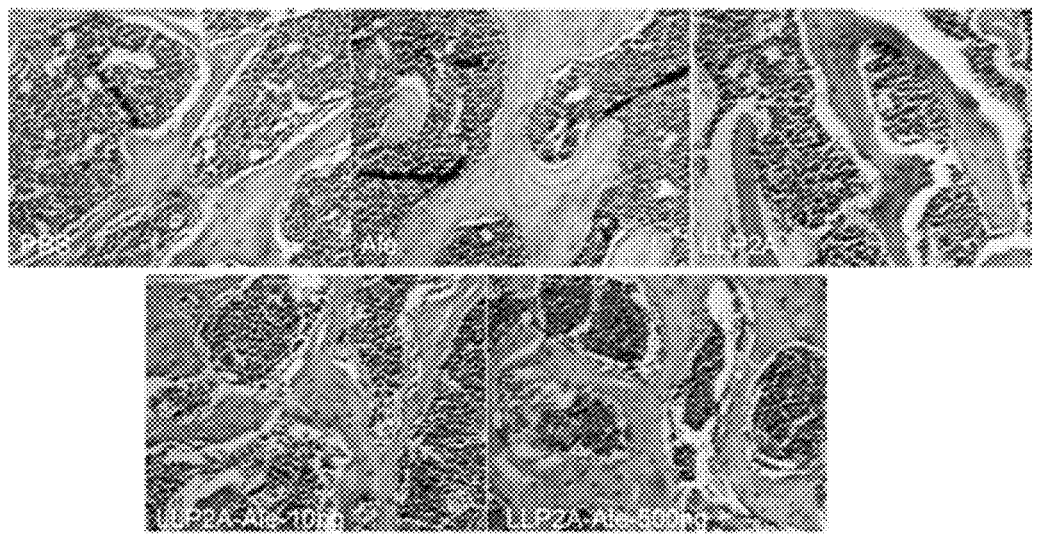
FIG. 9 shows LLP2A-Ale increases proliferating cell populations adjacent to bone surfaces. Decalcified $4^{th}$ lumbar vertebral sections were double-stained with alkaline phosphatase (blue staining) and BrdU (Bromodeoxyuridine) to monitor the proliferating cells (brown staining, yellow arrows).

Two-month-old female 129SvJ mice received intravenous (i.v.) injections of vehicle (PBS), 2A (5 nM), Ale (250 ng/mouse) or LLP2A-Ale [alendronate concentration of 10 ng/mouse (70 ng total compound weight) or alendronate concentration of 250 ng/mouse (1.75 total compound weight)]. The dose of alendronate used for the experiments were at least one-tenth lower than of the therapeutic dose of alendronate for the treatment of osteoporosis (See Colon-Emeric, C. S., *JAMA*, 2006, 296(24): p. 2968-9; Ma, Y. L., et al., *Endocrinology*, 2003, 144(5): p. 2008-15). As shown in FIG. 9, two days after the i.v. injections, LLP2A alone increased the number of proliferating cell populations within the marrow cavity. In contrast and as shown in FIG. 9, LLP2A-Ale increased these proliferating cell populations adjacent to bone surface. In order to monitor bone micro-architectural changes that resulted from the treatments, repeated in vivo microCT of the distal femurs were performed just prior to the first injections and after four weeks when the mice were sacrificed. As shown in FIG. 4, compared to the approximately 2-5% increase in cancellous bone mass in the PBS, LLP2A, and Ale-treated groups, LLP2A-Ale, at higher dose level (250 ng), increased cancellous bone mass by nearly 20%. As shown in FIG. 4, trabecular thickness was increased in two dose levels compared to the PBS-treated group. As shown in FIG. 5A-5C, LLP2A-Ale did not change early osteoblast maturation (P1NP levels) but increased osteoblast function (osteocalcin) with significant increases in surface-based bone formation parameters including osteoblast surface, mineral apposition rate and surface-based bone formation rate at the distal femur metaphysis. As shown in FIG. 6, LLP2A increased bone formation rate at both the endocortical and periosteal surfaces of the mid-femurs ($p>0.05$). As shown in FIG. 6, LLP2A significantly increased bone formation rate at both the endocortical and periosteal surfaces of the mid-femurs ($p<0.05$). There were no dose-responses observed at the cortical bone compartment.

In FIG. 9, two-month-old female 120SvJ mice received a single intravenous injection of PBS, alendronate (500 ng/mouse), LLP2A (5 nm/mouse) or LLP2A-Ale (10 ng or 500 ng/mouse). Mice were sacrificed 48 hours after the treatment.

MicroCT.

The right distal femur from each of the animals was scanned using MicroCT (VivaCT 40, Scanco Medical, Bassersdorf, Switzerland), with an isotropic resolution of 10 μm in all three spatial dimensions. The scan was initiated at the lateral periosteal margin through the medial periosteal margin of the distal femur and 0.1 mm from the highest part of the growth plate continuing proximally for 2 mm. Mineralized bone was separated from the bone marrow with a matching cube 3D segmentation algorithm. A normalized index, trabecular bone volume/total volume (BV/TV), was utilized to compare samples of varying size. Trabecular thickness (Tb. Th), trabecular separation (Tb.Sp) and trabecular number (Tb.N) were also calculated as described previously (Lane, N. E. et al., *J Bone Miner Res*, 2006, 21(3): p. 466-76; Yao, W., et al., *Arthritis Rheum*, 2008, 58(6): p. 1674-86; Yao, W., et al., *Arthritis Rheum*, 2008, 58(11): p. 3485-3497).

Bone Histomorphometry.

After fixation in 4% paraformaldehyde, the right distal femurs, mid-femurs and the 5th lumbar vertebral bodies were dehydrated in graded concentrations of ethanol and xylene and embedded un-decalcified in methyl methacrylate. The frontal sections (8 μm thick) were cut using a vertical bed microtome (Leica/Jung 2265) and affixed to slides coated with a 2% gelatin solution. Unstained 8-μm-thick sections were used for assessing fluorochrome labeling and dynamic changes in bone. Bone histomorphometry was performed using a semi-automatic image analysis (Bioquant Image Analysis Corporation, Nashville, Tenn.) linked to a microscope equipped with transmitted and fluorescent light. Bone turnover measurements included single—(sL.Pm) and double-labeled perimeter (dL.Pm), interlabel width (Ir.L.Wi) and osteoclast surface. These indices were used to calculate Mineralizing Surface (MS/BS) and mineral apposition rate (MAR) and surface-based bone formation rate (BFR/BS) at the trabecular, endocortical and periosteal surfaces (Lane, N. E., et al., *J Bone Miner Res*, 2006, 21(3): p. 466-76; Yao, W., et al., *Arthritis Rheum*, 2008, 58(6): p. 1674-86; Yao, W., et al., *Arthritis Rheum*, 2008, 58(11): p. 3485-3497; Yao, W., et al., *Bone*, 1999. 25(6): p. 697-702).

Immunohistochemistry Staining.

Bone samples were fixed in 4% paraformaldehyde, decalcified in 10% EDTA for 10 days and embedded in paraffin. Four-μm sections were obtained and incubated in 3% $H_2O_2$ in water to block endogenous peroxidases. Then the slides were incubated with 1% normal donkey serum in PBS Tween 20 in PBS. Then the sections were incubated with the primary antibodies. After blocking with peroxidase, the sections are incubated with the secondary antibody for detection. Negative control was included where primary antibody was omitted to differentiate unspecific staining.

Histochemical Analyses of Enzyme Activity.

Following sacrifice, small portions of organs were harvested and frozen in Optimal Cutting Temperature embedding media (Sakura, Torrance, Calif.) and sectioned in 12 μm thick slices. GUSB-specific histochemical analysis was performed using naphthol-AS-BI-β-D-glucuronide (Sigma-Aldrich) as a substrate, followed by counterstaining with methyl green.

Statistics.

Statistical significance was assessed by analysis of variance followed by Dunnett's post-hoc test for comparisons between the treatment groups to the PBS vehicle control group. $P<0.05$ was considered significant. All values are expressed as means±standard deviation.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the formula:

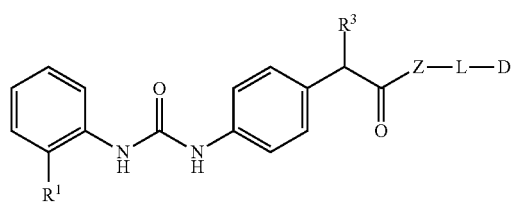

wherein $R^1$ is selected from the group consisting of halogen, $C_{1-6}$ alkyl, $C_{1-6}$ alkoxy, and $C_{1-6}$ haloalkyl;

$R^3$ is selected from the group consisting of H, $C_{1-6}$ alkyl and $C_{3-8}$ cycloalkyl;

Z is a peptide having 3-20 independently selected amino acids, wherein at least one amino acid is selected from the group consisting of an unnatural amino acid and a D-amino acid;

L is a linker; and

D is a bisphosphonate drug.

2. The compound of claim 1, wherein $R^1$ is methyl and $R^3$ is H.

3. The compound of claim 1, wherein peptide Z has the formula:

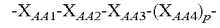

wherein $X_{AA1}$ is selected from the group consisting of a hydrophobic amino acid and derivatives of lysine, homolysine (Hly), ornithine (Orn) and α,γ-diaminobutyric acid (Dbu);

$X_{AA2}$ is a negatively charged amino acid;

$X_{AA3}$ is a hydrophobic amino acid;

X$_{AA4}$ is selected from the group consisting of a naturally-occurring amino acid, an unnatural amino acid, and a D-amino acid; and subscript p is 0 or 1.

4. The compound of claim 3, wherein

X$_{AA1}$ is lysine-A38 (Lys38);

X$_{AA2}$ is α-aminohexanedioic acid (Aad);

X$_{AA3}$ is a hydrophobic amino acid; and subscript p is 0.

5. The compound of claim 1, wherein peptide Z is selected from the group consisting of Lys38-Aad-D-Phe, -Lys38-Aad-Ach, -Lys38-Aad-D-Nal-2, -Lys38-Aad-Ile, -Lys38-Aad-Val, and Lys38-Aad-Leu.

6. The compound of claim 1, wherein peptide Z is -Lys38-Aad-Ach.

7. The compound of claim 1, wherein linker L comprises at least one of N-(8-amino-3,6-dioxa-octyl)succinamic acid (EBES) and polyethylene glycol (PEG).

8. The compound of claim 1, wherein linker L is selected from the group consisting of:

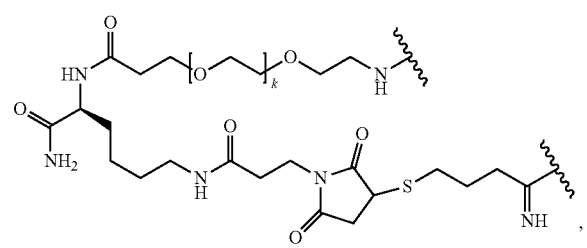

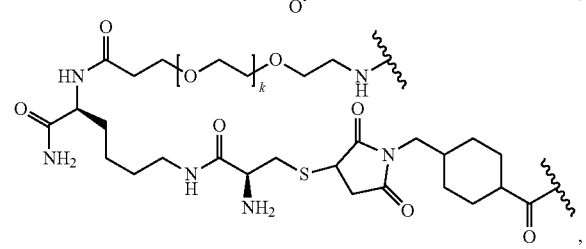

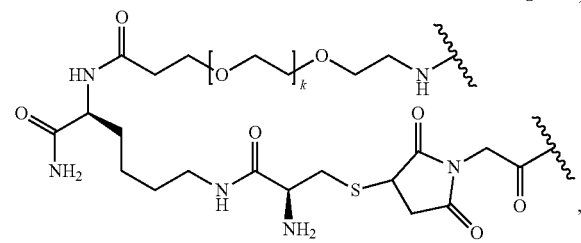

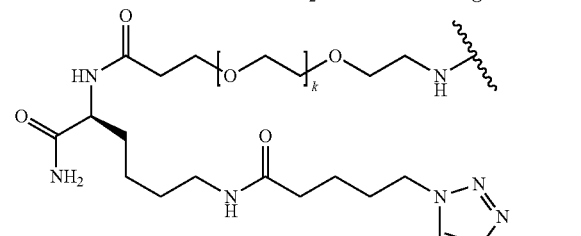

-continued

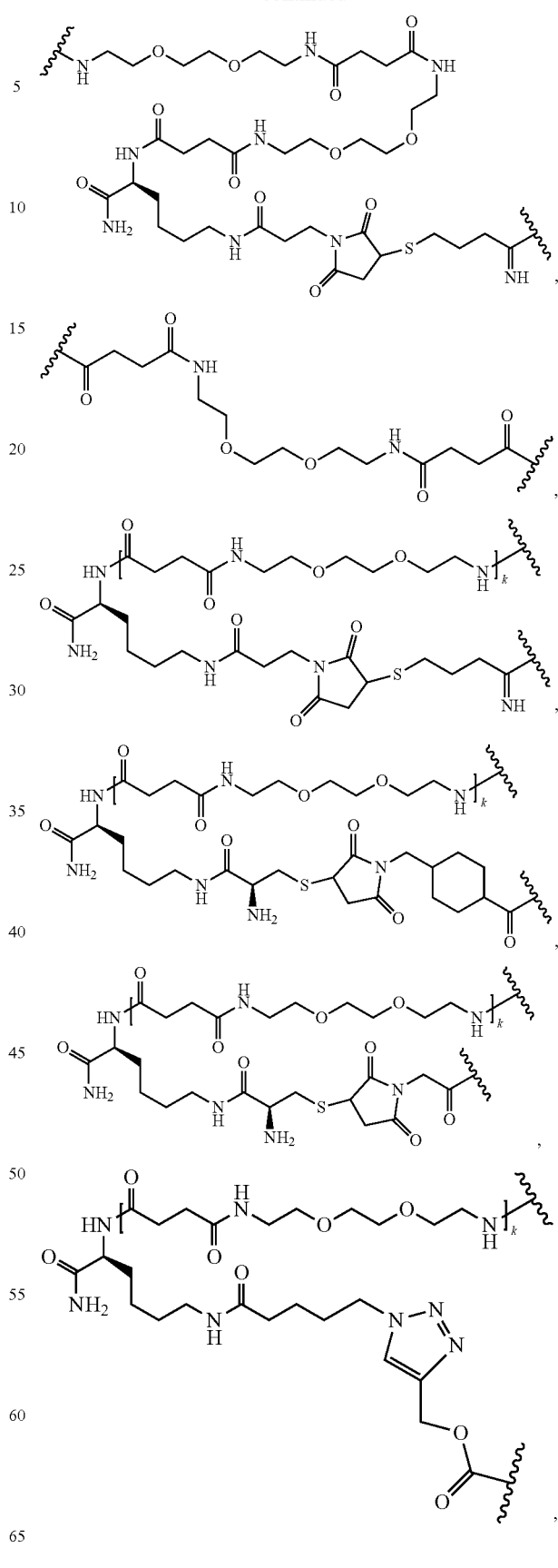

-continued

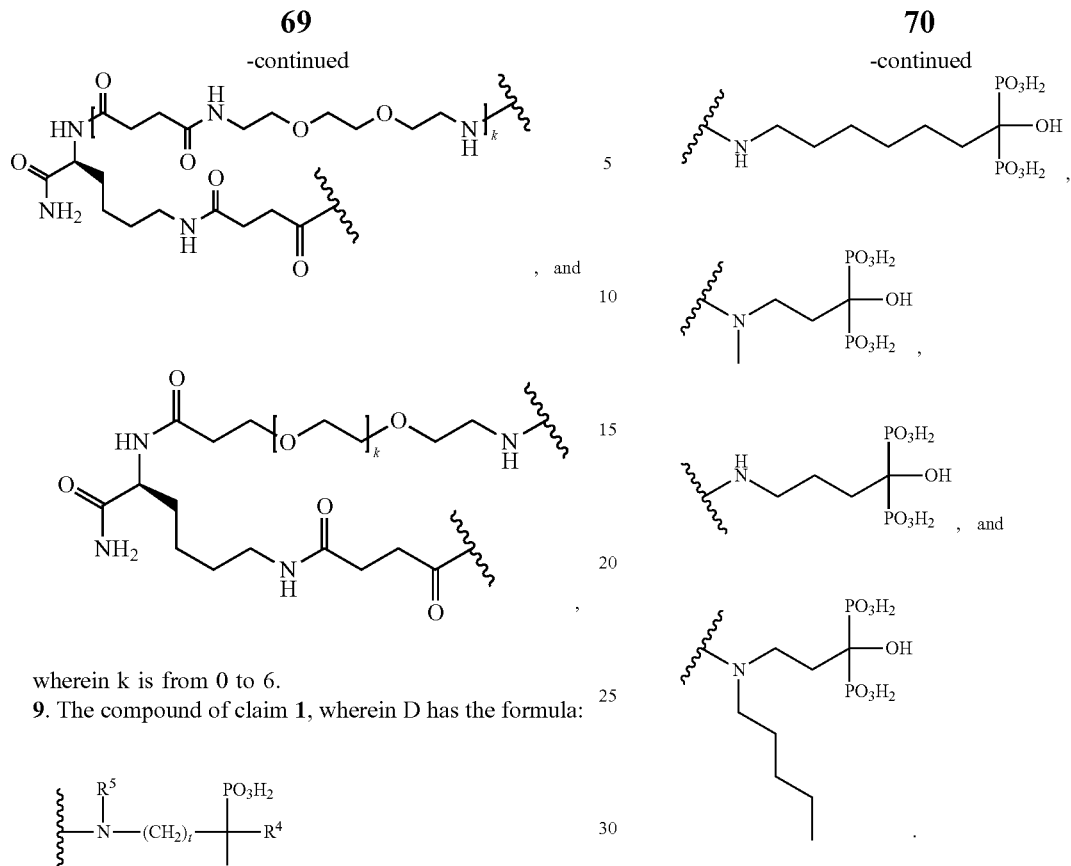

wherein k is from 0 to 6.

9. The compound of claim 1, wherein D has the formula:

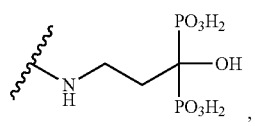

wherein
R⁴ is selected from the group consisting of H, OH and halogen;
R⁵ is selected from the group consisting of H and $C_{1-6}$ alkyl; and
subscript t is from 1 to 6.

10. The compound of claim 1, wherein D has the formula selected from the group consisting of:

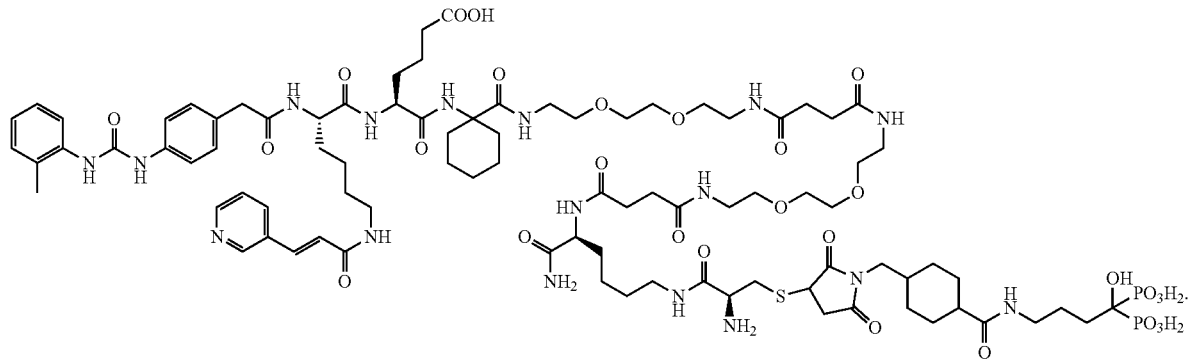

11. A pharmaceutical composition comprising the compound of claim 1 and a pharmaceutically acceptable excipient.

12. A compound having the formula:

13. A pharmaceutical composition comprising the compound of claim 12 and a pharmaceutically acceptable excipient.

14. A method of treating osteoporosis, comprising administering the compound of claim 1 to a subject having osteoporosis.

15. A method of promoting bone growth in a subject, comprising administering to the subject the compound of claim 1.

16. A method of treating low bone mass in a subject, comprising administering to the subject the compound of claim 1.

17. A method of treating osteoporosis, comprising administering the compound of claim 12 to a subject having osteoporosis.

18. A method of treating a bone injury in a subject, comprising administering to the subject the compound of claim 12.

19. The method of claim 18, wherein the bone injury is a bone fracture.

* * * * *

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (4)..(4)
<223> OTHER INFORMATION: hydroxyproline

<400> SEQUENCE: 1

Leu Xaa Val Xaa
1

<210> SEQ ID NO 2
<211> LENGTH: 4
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: homoleucine
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (4)..(4)
<223> OTHER INFORMATION: alpha cyclohexylglycine

<400> SEQUENCE: 2

Xaa Xaa Phe Xaa
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (3)..(3)
<223> OTHER INFORMATION: propargyl glycine
<220> FEATURE:
<221> NAME/KEY: MISC_FEATURE
<222> LOCATION: (5)..(5)
<223> OTHER INFORMATION: hydroxyproline

<400> SEQUENCE: 3

Xaa Asp Xaa Gly Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: cyclopropylalanine
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (3)..(3)
<223> OTHER INFORMATION: 1-aminocyclopropane-1-carboxylic acid
<220> FEATURE:
<221> NAME/KEY: MISC_FEATURE
<222> LOCATION: (4)..(4)
<223> OTHER INFORMATION: hydroxyproline

<400> SEQUENCE: 4

Xaa Xaa Xaa Xaa
1

<210> SEQ ID NO 5
<211> LENGTH: 5
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (4)..(4)
<223> OTHER INFORMATION: alpha aminohexanedioic acid
<220> FEATURE:
<221> NAME/KEY: MISC_FEATURE
<222> LOCATION: (5)..(5)
<223> OTHER INFORMATION: 2-aminoindane-2-carboxylic acid

<400> SEQUENCE: 5

Xaa Asp Ala Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (3)..(3)
<223> OTHER INFORMATION: alpha cyclohexylglycine
<220> FEATURE:
<221> NAME/KEY: MISC_FEATURE
<222> LOCATION: (4)..(4)
<223> OTHER INFORMATION: hydroxyproline
<220> FEATURE:
<221> NAME/KEY: MISC_FEATURE
<222> LOCATION: (5)..(5)
<223> OTHER INFORMATION: alpha aminohexanedioic acid

<400> SEQUENCE: 6

Xaa Xaa Xaa Xaa Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: cyclopropylalanine
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (3)..(3)
<223> OTHER INFORMATION: alpha cyclohexylglycine
<220> FEATURE:
<221> NAME/KEY: MISC_FEATURE
<222> LOCATION: (5)..(5)
<223> OTHER INFORMATION: alpha aminohexanedioic acid
<220> FEATURE:
<221> NAME/KEY: MISC_FEATURE
<222> LOCATION: (6)..(6)
```

```
<223> OTHER INFORMATION: 3-chlorophenylalanine
<220> FEATURE:
<221> NAME/KEY: MISC_FEATURE
<222> LOCATION: (7)..(7)
<223> OTHER INFORMATION: alpha aminohexanedioic acid

<400> SEQUENCE: 7

Xaa Xaa Xaa Pro Xaa Xaa Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: homoleucine
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (4)..(4)
<223> OTHER INFORMATION: hydroxyproline
<220> FEATURE:
<221> NAME/KEY: MISC_FEATURE
<222> LOCATION: (5)..(5)
<223> OTHER INFORMATION: alpha cyclohexylglycine

<400> SEQUENCE: 8

Xaa Xaa Val Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (3)..(3)
<223> OTHER INFORMATION: phenylglycine
<220> FEATURE:
<221> NAME/KEY: MISC_FEATURE
<222> LOCATION: (4)..(4)
<223> OTHER INFORMATION: 1-aminocyclopentane-1-carboxylic acid
<220> FEATURE:
<221> NAME/KEY: MISC_FEATURE
<222> LOCATION: (5)..(5)
<223> OTHER INFORMATION: alpha aminohexanedioic acid

<400> SEQUENCE: 9

Xaa Glu Xaa Xaa Xaa
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
```

```
<223> OTHER INFORMATION: 1-aminocyclopentane-1-carboxylic acid
<220> FEATURE:
<221> NAME/KEY: MISC_FEATURE
<222> LOCATION: (2)..(2)
<223> OTHER INFORMATION: alpha aminohexanedioic acid
<220> FEATURE:
<221> NAME/KEY: MISC_FEATURE
<222> LOCATION: (3)..(3)
<223> OTHER INFORMATION: norleucine
<220> FEATURE:
<221> NAME/KEY: MISC_FEATURE
<222> LOCATION: (4)..(4)
<223> OTHER INFORMATION: alpha aminohexanedioic acid

<400> SEQUENCE: 10

Xaa Xaa Xaa Xaa
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: cyclopropylalanine
<220> FEATURE:
<221> NAME/KEY: MISC_FEATURE
<222> LOCATION: (2)..(2)
<223> OTHER INFORMATION: alpha-aminohexanedioic acid
<220> FEATURE:
<221> NAME/KEY: MISC_FEATURE
<222> LOCATION: (3)..(3)
<223> OTHER INFORMATION: 1-aminocyclopropane-1-carboxylic acid
<220> FEATURE:
<221> NAME/KEY: MISC_FEATURE
<222> LOCATION: (4)..(4)
<223> OTHER INFORMATION: alpha-aminohexanedioic acid

<400> SEQUENCE: 11

Xaa Xaa Xaa Xaa
1

<210> SEQ ID NO 12
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: alpha-aminohexanedioic acid
<220> FEATURE:
<221> NAME/KEY: MISC_FEATURE
<222> LOCATION: (3)..(3)
<223> OTHER INFORMATION: 1-aminocyclopropane-1-carboxylic acid
<220> FEATURE:
<221> NAME/KEY: MISC_FEATURE
```

```
<222> LOCATION: (4)..(4)
<223> OTHER INFORMATION: alpha-aminohexanedioic acid

<400> SEQUENCE: 12

Leu Xaa Xaa Xaa
1

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: homoleucine
<220> FEATURE:
<221> NAME/KEY: MISC_FEATURE
<222> LOCATION: (5)..(5)
<223> OTHER INFORMATION: alpha-cyclohexylglycine

<400> SEQUENCE: 13

Xaa Asp Ile Pro Xaa
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: cyclohexylalanine
<220> FEATURE:
<221> NAME/KEY: MISC_FEATURE
<222> LOCATION: (4)..(4)
<223> OTHER INFORMATION: hydroxyproline
<220> FEATURE:
<221> NAME/KEY: MISC_FEATURE
<222> LOCATION: (5)..(6)
<223> OTHER INFORMATION: homocitrulline

<400> SEQUENCE: 14

Xaa Asp Leu Xaa Xaa Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: lysine 3-pyridine propionate amide
<220> FEATURE:
<221> NAME/KEY: MISC_FEATURE
<222> LOCATION: (2)..(2)
<223> OTHER INFORMATION: alpha-aminohexanedioic acid
<220> FEATURE:
<221> NAME/KEY: MISC_FEATURE
<222> LOCATION: (3)..(3)
<223> OTHER INFORMATION: norvaline
<220> FEATURE:
<221> NAME/KEY: MISC_FEATURE
<222> LOCATION: (4)..(5)
<223> OTHER INFORMATION: hydroxyproline

<400> SEQUENCE: 15
```

```
Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (4)..(5)
<223> OTHER INFORMATION: hydroxyproline

<400> SEQUENCE: 16

Xaa Asp Ile Xaa Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: homoleucine
<220> FEATURE:
<221> NAME/KEY: MISC_FEATURE
<222> LOCATION: (3)..(3)
<223> OTHER INFORMATION: alpha-aminobutyric acid
<220> FEATURE:
<221> NAME/KEY: MISC_FEATURE
<222> LOCATION: (4)..(4)
<223> OTHER INFORMATION: hydroxyproline
<220> FEATURE:
<221> NAME/KEY: MISC_FEATURE
<222> LOCATION: (5)..(6)
<223> OTHER INFORMATION: homocitrulline

<400> SEQUENCE: 17

Xaa Glu Xaa Xaa Xaa Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: norleucine
<220> FEATURE:
<221> NAME/KEY: MISC_FEATURE
<222> LOCATION: (5)..(5)
<223> OTHER INFORMATION: homocitrulline
```

```
<400> SEQUENCE: 18

Xaa Asp Val Pro Xaa Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: cyclohexylalanine
<220> FEATURE:
<221> NAME/KEY: MISC_FEATURE
<222> LOCATION: (2)..(2)
<223> OTHER INFORMATION: alpha-aminohexanedioic acid
<220> FEATURE:
<221> NAME/KEY: MISC_FEATURE
<222> LOCATION: (4)..(4)
<223> OTHER INFORMATION: 2-amino-2-naphthylacetic acid
<220> FEATURE:
<221> NAME/KEY: MISC_FEATURE
<222> LOCATION: (5)..(5)
<223> OTHER INFORMATION: 1-amino-1-(4-hydroxycyclohexyl) carboxylic acid

<400> SEQUENCE: 19

Xaa Xaa Val Xaa Xaa
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: homophenylalanine
<220> FEATURE:
<221> NAME/KEY: MISC_FEATURE
<222> LOCATION: (4)..(4)
<223> OTHER INFORMATION: hydroxyproline

<400> SEQUENCE: 20

Xaa Asp Ala Xaa
1
```